(12) United States Patent
Hubbell et al.

(10) Patent No.: US 12,365,714 B2
(45) Date of Patent: Jul. 22, 2025

(54) METHODS AND COMPOSITIONS FOR TREATING CANCER WITH ECM-AFFINITY PEPTIDES LINKED TO CYTOKINES

(71) Applicant: The University of Chicago, Chicago, IL (US)

(72) Inventors: Jeffrey A. Hubbell, Chicago, IL (US); Jun Ishihara, Chicago, IL (US); Ako Ishihara, Chicago, IL (US); Koichi Sasaki, Chicago, IL (US); Melody Swartz, Chicago, IL (US); Aslan Mansurov, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1160 days.

(21) Appl. No.: 15/733,582

(22) PCT Filed: Mar. 5, 2019

(86) PCT No.: PCT/US2019/020685
§ 371 (c)(1),
(2) Date: Sep. 3, 2020

(87) PCT Pub. No.: WO2019/173289
PCT Pub. Date: Sep. 12, 2019

(65) Prior Publication Data
US 2021/0094995 A1     Apr. 1, 2021

Related U.S. Application Data

(60) Provisional application No. 62/727,156, filed on Sep. 5, 2018, provisional application No. 62/638,520, filed on Mar. 5, 2018.

(51) Int. Cl.
| | | |
|---|---|---|
| A61K 38/20 | (2006.01) | |
| A61K 9/00 | (2006.01) | |
| A61K 45/06 | (2006.01) | |
| A61P 35/00 | (2006.01) | |
| C07K 14/55 | (2006.01) | |
| C07K 14/755 | (2006.01) | |

(52) U.S. Cl.
CPC ............ *C07K 14/55* (2013.01); *A61K 9/0019* (2013.01); *A61K 38/2013* (2013.01); *A61K 45/06* (2013.01); *A61P 35/00* (2018.01); *C07K 14/755* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,589,330 A | 5/1986 | Teron |
| 4,818,542 A | 4/1989 | DeLuca et al. |
| 4,879,236 A | 11/1989 | Smith et al. |
| 5,871,986 A | 2/1999 | Boyce |
| 5,925,565 A | 7/1999 | Berlioz et al. |
| 5,935,819 A | 8/1999 | Eichner et al. |
| 6,087,329 A | 7/2000 | Armitage et al. |
| 6,103,379 A | 8/2000 | Margel et al. |
| 6,130,082 A | 10/2000 | Majarian et al. |
| 6,277,812 B1 | 8/2001 | Ruoslahti et al. |
| 6,329,381 B1 | 12/2001 | Kurimoto et al. |
| 6,387,498 B1 | 5/2002 | Coulter et al. |
| 6,585,980 B1 | 7/2003 | Chan et al. |
| 6,617,135 B1 | 9/2003 | Gillies et al. |
| 6,712,997 B2 | 3/2004 | Won et al. |
| 7,192,725 B2 | 3/2007 | Chan et al. |
| 7,550,263 B2 | 6/2009 | Meade et al. |
| 8,273,357 B2 | 9/2012 | Hacohen et al. |
| 8,734,774 B2 | 5/2014 | Frelinger et al. |
| 10,300,016 B2 | 5/2019 | Markovic et al. |
| 2003/0099644 A1 | 5/2003 | Ahuja et al. |
| 2006/0241076 A1 | 10/2006 | Uhlmann et al. |
| 2009/0005298 A1 | 1/2009 | Goldberg et al. |
| 2009/0093407 A1 | 4/2009 | Hall et al. |
| 2010/0075995 A1 | 3/2010 | Biggadike et al. |
| 2011/0086030 A1 | 4/2011 | Ware |
| 2012/0052043 A1 | 3/2012 | Kungl |
| 2012/0289468 A1 | 11/2012 | Barnett et al. |
| 2014/0010832 A1 | 1/2014 | Hubbeil et al. |
| 2014/0315253 A1 | 10/2014 | Dai et al. |

(Continued)

FOREIGN PATENT DOCUMENTS

| | | |
|---|---|---|
| JP | 5639039 | 2/2016 |
| WO | WO 2003/086280 | 10/2003 |
| WO | WO 2005/097993 | 10/2005 |

(Continued)

OTHER PUBLICATIONS

Office Communication issued in corresponding European Application No. 19764476.8, dated Jun. 29, 2023.

Schwartz, et al. "Managing toxicities of high-dose interleukin-2", *Oncology*, vol. 16, No. 11, pp. 11-20, 2002.

Stagg et al. "Granulocyte-macrophage colony-stimulating factor and interleukin-2 fusion cDNA for cancer gene immunotherapy", *Cancer Research*, American Association for Cancer Research, vol. 64, No. 24, pp. 8795-8799, 2004.

(Continued)

*Primary Examiner* — Michael D Pak
(74) *Attorney, Agent, or Firm* — Norton Rose Fulbright US LLP

(57) ABSTRACT

The methods and compositions described herein address the need in the art by providing compositions and methods for a therapy with a cytokine that is specifically targeted to and/or retained intra- or peri-tumorally, limiting systemic exposure and reducing side-effects. Accordingly, aspects of the disclosure relate to a composition comprising an immunotherapeutic antibody operatively linked to an extracellular matrix (ECM)-affinity peptide. An ECM-affinity peptide is one that has affinity for an extracellular matrix protein.

5 Claims, 14 Drawing Sheets

Specification includes a Sequence Listing.

(56) References Cited

U.S. PATENT DOCUMENTS

2016/0106858 A1 4/2016 Hall et al.

FOREIGN PATENT DOCUMENTS

| WO | WO 2007/062107 | 5/2007 |
|---|---|---|
| WO | WO 2008/033432 | 3/2008 |
| WO | WO 2010/018132 | 2/2010 |
| WO | WO 2012/112690 | 8/2012 |
| WO | WO 2014/006082 | 1/2014 |
| WO | WO 2015/124297 | 8/2015 |
| WO | WO 2018/184003 | 10/2018 |
| WO | WO 2018/195386 | 10/2018 |
| WO | WO 2019/222294 | 11/2019 |
| WO | WO 2020/041758 | 2/2020 |

OTHER PUBLICATIONS

Bienkowska, et al. "The von Willebrand factor A3 domain does not contain a metal ion-dependent adhesion site motif", *The Journal of Biological Chemistry*, vol. 272, No. 40, pp. 25162-25167, 1997.

Addi et al., "Design and Use of Chimeric Proteins Containing a Collagen-Binding Domain for Wound Healing and Bone Regeneration" *Tissue Engineering Part B: Reviews*, 2016, 23(2), 163-182.

Akdis et al., "Interleukins, from 1 to 37, and interferon-γ: Receptors, functions, and roles in diseases" *The Journal of allergy and clinical immunology* 2011, 127, 701-21.

Angel et al., "12-O-Tetradecanoyl-Phorbol-13-Acetate Induction of the Human Collagenase Gene Is Mediated by an Inducible Enhancer Element Located in the 5'- Flanking Region" *Molecular and Cellular Biology* 1987, 7(6), 2256-2266.

Angel et al., "Phorbol ester-inducible genes contain a common cis element recognized by a TPA-modulated trans-acting factor" *Cell* 1987, 49(6), 729-739.

Asher et al., "Murine tumor cells transduced with the gene for tumor necrosis factor- alpha. Evidence for paracrine immune effects of tumor necrosis factor against tumors." *J. Immunol.* 1991, 146, 3227-3234.

Atchinson et al., "The role of the K enhancer and its binding factor NF-κB in the developmental regulation of K gene transcription" *Cell* 1987, 48(1), 121-128.

Banerji et al., "A lymphocyte-specific cellular enhancer is located downstream of the joining region in immunoglobulin heavy chain genes" *Cell* 1983, 33(3), 729-740.

Banerji et al., "Expression of a β-globin gene is enhanced by remote SV40 DNA sequences" *Cell* 1981, 27(2), 299-308.

Beatty, et al., "CD40 Agonists Alter Tumor Stroma and Show Efficacy Against Pancreatic Carcinoma in Mice and Humans," *Science*, 331(6024):1612-1616, 2011.

Bergmeier, Wolfgang and Richard O. Hynes, "Extracellular Matrix Proteins in Hemostasis and Thrombosis" *Cold Spring Harb Perspect Biol.* 2012, 4:a005132, 17 pages.

Berkhout et al., "trans Activation of Human Immunodeficiency Virus Type 1 Is Sequence Specific for Both the Single-Stranded Bulge and Loop of the trans-Acting-Responsive Hairpin: a Quantitative Analysis" *Journal of Virology* 1989, 63(12), 5501- 5504.

Blanar et al., "A gamma-interferon-induced factor that binds the interferon response sequence of the MHC class I gene, H-2K$^b$" *The EMBO Journal* 1989, 8(4), 1139-1144.

Bodine et al., "An enhancer element lies 3' to the human $^A\gamma$ globin gene" *The EMBO Journal* 1987, 6(10), 2997-3004.

Boshart et al., "A very strong enhancer is located upstream of an immediate early gene of human cytomegalovirus" *Cell* 1985, 41(2), 521-530.

Bosze et al., "A transcriptional enhancer with specificity for erythroid cells is located in the long terminal repeat of the Friend murine leukemia virus." *EMBO J* 1986, 5, 1615-1623.

Boyman, Onur and Jonathan Sprent., "The role of interleukin-2 during homeostasis and activation of the immune system" *Nature reviews Immunology* 2012, 12, 180-190.

Braddock et al., "HIV-1 Tat "activates" presynthesized RNA in the nucleus" *Cell* 1989, 58(2), 269-279.

Brinker, Jeffrey C., and George W. Scherer. Sol-Gel Science: *The Physics and Chemistry of Sol-Gel Processing*. Academic Press, 1990.

Briquez, et al., "Extracellular Matrix-Inspired Growth Factor Delivery Systems for Skin Wound Healing," *Advances in Wound Care*, 4(8): 479-489, 2015.

Campbell et al., "Functional Analysis of the Individual Enhancer Core Sequences of Polyomavirus: Cell-Specific Uncoupling of DNA Replication from Transcription" *Molecular and Cellular Biology* 1988, 8(5), 1993-2004.

Camper et al., "The Developmental Regulation of Albumin and a-Fetoprotein Gene Expression" *Progress in Nucleic Acid Research and Molecular Biology* 1989, 36, 131-143.

Campo et al., "Transcriptional control signals in the genome of bovine papillomavirus type 1" *Nature* 1983, 303, 77-80.

Carnemolla et al., "Enhancement of the antitumor properties of interleukin-2 by its targeted delivery to the tumor blood vessel extracellular matrix" *Blood* 2002, 99, 1659-65.

Caruso et al., "Characterization of Polyelectrolyte-Protein Multilayer Films by Atomic Force Microscopy, Scanning Electron Microscopy, and Fourier Transform Infrared Reflection-Absorption Spectroscopy" *Langmuir* 1998, 14(16), 4559-4565.

Caruso et al., "Protein Multilayer Formation on Colloids through a Stepwise Self-Assembly Technique" *J. Am. Chem. Soc.* 1999, 121(25), 6039-6046.

Celander et al., "Glucocorticoid Regulation of Murine Leukemia Virus Transcription Elements Is Specified by Determinants within the Viral Enhancer Region" *Journal of Virology* 1987, 61(2), 269-275.

Celander et al., "Regulatory elements within the murine leukemia virus enhancer regions mediate glucocorticoid responsiveness." *Journal of Virology* 1988, 62(4), 1314-1322.

Chandler et al., "DNA sequences bound specifically by glucocorticoid receptor in vitro render a heterologous promoter hormone responsive in vivo" *Cell* 1983, 33(2), 489-499.

Chang et al., "Glucose-Regulated Protein (GRP94 and GRP78) Genes Share Common Regulatory Domains and Are Coordinately Regulated by Common trans-Acting Factors" *Molecular and Cellular Biology* 1989, 9(5), 2153-2162.

Chari et al., "Antibody-Drug Conjugates: An Emerging Concept in Cancer Therapy" *Angew Chem Int Ed Engl* 2014, 53(3), 796-827.

Chatterjee et al., "Negative regulation of the thyroid-stimulating hormone a gene by thyroid hormone: Receptor interaction adjacent to the TATA box" *Proc. Natl. Acad. Sci. USA* 1989, 86, 9114-9118.

Choi et al., "Requirement for the Simian Virus 40 Small Tumor Antigen in Tumorigenesis in Transgenic Mice" *Molecular and Cellular Biology* 1988, 8(8), 3382-3390.

Cohen et al., "A repetitive sequence element 3' of the human c-Ha-ras1 gene has enhancer activity" *Journal of Cellular Physiology* 1987, 133, 75-81.

Collin, M., "Immune checkpoint inhibitors: a patent review (2010-2015)" *Expert Opin Ther Pat.* 2016, 26(5), 555-64.

Costa et al., "The Cell-Specific Enhancer of the Mouse Transthyretin (Prealbumin) Gene Binds a Common Factor at One Site and a Liver-Specific Factor(s) at Two Other Sites" *Molecular and Cellular Biology* 1988, 8(1), 81-90.

Cripe et al., "Transcriptional regulation of the human papillomavirus-16 E6-E7 promoter by a keratinocyte-dependent enhancer, and by viral E2 trans-activator and repressor gene products: implications for cervical carcinogenesis." *EMBO J* 1987, 6, 3745-3753.

Culotta et al., "Fine Mapping of a Mouse Metallothionein Gene Metal Response Element" *Molecular and Cellular Biology* 1989, 9(3), 1376-1380.

Dandolo et al., "Regulation of Polyoma Virus Transcription in Murine Embryonal Carcinoma Cells" *Journal of Virology* 1983, 47(1), 55-64.

Danhier et al., "To exploit the tumor microenvironment: Passive and active tumor targeting of nanocarriers for anti-cancer drug delivery" *J Control Release* 2010, 148, 135-46.

Davies et al., "Engineered Particle Surfaces" *Advanced Materials* 1998, 10(15).

(56) References Cited

OTHER PUBLICATIONS

De Villiers et al., "Polyoma virus DNA replication requires an enhancer" *Nature* 1984, 312, 242-246.
Deschamps et al., "Cellulase Production by Trichoderma harzianum in Static and Mixed Solid-state Fermentation Reactors Under Nonaseptic Conditions" *Biotechnology and Bioengineering* 1985, 27(9), 1385-1388.
Di Lullo et al., "Mapping the Ligand-binding Sites and Disease associated Mutations on the Most Abundant Protein in the Human, Type I Collagen" *Journal of Biological Chemistry* 2002, 277, 4223-31.
Dubois et al., "Glycoprotein VI—dependent and -independent pathways of thrombus formation in vivo" *Blood* 2006, 107, 3902-06.
Edbrooke et al., "Identification of cis-Acting Sequences Responsible for Phorbol Ester Induction of Human Serum Amyloid A Gene Expression via a Nuclear Factor κB-Like Transcription Factor" *Molecular and Cellular Biology* 1989, 9(5), 1908-1916.
Edlund et al., "Cell-specific expression of the rat insulin gene: evidence for role of two distinct 5' flanking elements" *Science* 1985, 230(4728), 912-916.
Eigentler et al., "A Dose-Escalation and Signal-Generating Study of the Immunocytokine L19-IL2 in Combination with Dacarbazine for the Therapy of Patients with Metastatic Melanoma" *Clinical Cancer Research* 2011, 17, 7732-42.
Ellmark, et al., "Tumor-Directed Immunotherapy Can Generate Tumor-Specific T Cell Responses Through Localized Co-stimulation," *Cancer Immunology Immunotherapy* 2017, 66: 1-7.
European Search Report issued in Corresponding European Application No. 18787963.0, dated Nov. 20, 2020.
Fankhauser et al., "Tumor lymphangiogenesis promotes T cell infiltration and potentiates immunotherapy in melanoma" *Science Translational Medicine* 2017, 9(407), eaal4712.
Feng et al., "HIV-1 tat trans-activation requires the loop sequence within tar" *Nature* 1988, 334, 165-167.
Firak et al., "Minimal Transcriptional Enhancer of Simian Virus 40 is a 74-Base- Pair Sequence That Has Interacting Domains" *Molecular and Cellular Biology* 1986, 6(11), 3667-3676.
Foecking et al., "Powerful and versatile enhancer- promoter unit for mammalian expression vectors" *Gene* 1986, 45(1), 101-105.
Fransen, et al., "Controlled Local Delivery of CTLA-4 Blocking Antibody Induces CD8+ T-Cell-Dependent Tumor Eradication and Decreases Risk of Toxic Side Effects," *Clinical Cancer Research* 2013, 19(19), 5381-5389.
Fujita et al., "Interferon-β gene regulation: Tandemly repeated sequences of a synthetic 6 bp oligomer function as a virus-inducible enhancer" *Cell* 1987, 49(3), 357-367.
Gilles et al., "A tissue-specific transcription enhancer element is located in the major intron of a rearranged immunoglobulin heavy chain gene" *Cell* 1983, 33(3), 717-728.
Gloss et al., "The upstream regulatory region of the human papilloma virus-16 contains an E2 protein- independent enhancer which is specific for cervical carcinoma cells and regulated by glucocorticoid hormones." *EMBO J* 1987, 6, 3735-3743.
Godbout et al., "Fine-Structure Mapping of the Three Mouse α-Fetoprotein Gene Enhancers" *Molecular and Cellular Biology* 1988, 8(3), 1169-1178.
Golman et al., "Fine Particle Coating by Chemical Vapor Deposition for Functional Materials" *Trends in Chemical Engineering* 2000, 6, 1-16.
Goodbourn et al., "The human β-interferon gene enhancer is under negative control" *Cell* 1986, 45(4), 601-610.
Goodbourn, Stephen and Tom Maniatis, "Overlapping positive and negative regulatory domains of the human , B-interferon gene" *Proc. Natl. Acad. Sci. USA* 1988, 85, 1447-1451.
Green et al., "trans Activation of Granulocyte-Macrophage Colony-Stimulating Factor and the Interleukin-2 Receptor in Transgenic Mice Carrying the Human T-Lymphotropic Virus Type 1 tax Gene" *Molecular and Cellular Biology* 1989, 9(11), 4731-4737.

Grosschedl et al., "Cell-type specificity of iminunoglobulin gene expression is regulated by at least three DNA sequence elements" *Cell* 1985, 41(3), 885-897.
Hanprasopwattana et al., "Titania coatings on monodisperse silica spheres: characterization using 2-propanol dehydration and TEM" *Langmuir* 1996, 12, 3173-3179.
Haslinger et al., "Upstream promoter element of the human metallothionein-II$_A$ gene can act like an enhancer element" *Proc. Natl. Acad. Sci. USA* 1985, 82, 8572-8576.
Hauber et al., "Mutational analysis of the trans-activation-responsive region of the human immunodeficiency virus type I long terminal repeat." *Journal of Virology* 1988, 62(3), 673-679.
Havell et al., "The antitumor function of tumor necrosis factor (TNF), I. Therapeutic action of TNF against an established murine sarcoma is indirect, immunologically dependent, and limited by severe toxicity." *J. Exp. Med.* 1988, 167, 1067-1085.
Heil et al., "Species-Specific Recognition of Single- Stranded RNA via Toll-like Receptor 7 and 8" *Science* 2004, 303(5663), 1526-1529.
Hen et al., "A mutated polyoma virus enhancer which is active in undifferentiated embryonal carcinoma cells is not repressed by adenovirus-2 E1A products" *Nature* 1986, 321, 249-251.
Hensel et al., "PMA-responsive 5' flanking sequences of the human TNF gene." *Lymphokine Research* 1988, 8(3), 347-351.
Herr et al., "The SV40 enhancer is composed of multiple functional elements that can compensate for one another" *Cell* 1986, 45(3), 461-470.
Hirochika et al., "Enhancers and trans-acting E2 transcriptional factors of papillomaviruses." *Journal of Virology* 1987, 61(8), 2599-2606.
Hirsh et al., "Identification of Positive and Negative Regulatory Elements Governing Cell-Type-Specific Expression of the Neural Cell Adhesion Molecule Gene" *Molecular and Cellular Biology* 1990, 10(5), 1959-1968.
Holbrook et al., "cis-Acting transcriptional regulatory sequences in the gibbon ape leukemia virus (GALV) long terminal repeat" *Virology* 1987, 157(1), 211-219.
Horlick et al. "The Upstream Muscle-Specific Enhancer of the Rat Muscle Creatine Kinase Gene Is Composed of Multiple Elements" *Molecular and Cellular Biology* 1989, 9(6), 2396-2413.
Huang et al., "Glucocorticoid regulation of the Ha-MuSV p21 gene conferred by sequences from mouse mammary tumor virus" *Cell* 1981, 27(2), 245-255.
Hug et al., "Organization of the Murine Mx Gene and Characterization of Its Interferon- and Virus-Inducible Promoter" *Molecular and Cellular Biology* 1988, 8(8), 3065-3079.
Hummel et al. "Synthetic Deletion of the Interleukin 23 Receptor (IL-23R) Stalk Region Led to Autonomous IL-23R Homodimerization and Activation," *Molecular and Cellular Biology* 2017, vol. 37, Iss. 17, pp. 1-19.
Hwang et al., "Characterization of the S-Phase-Specific Transcription Regulatory Elements in a DNA Replication-Independent Testis-Specific H2B (TH2B) Histone Gene" *Molecular and Cellular Biology* 1990, 10(2), 585-592.
Iler, K.R., *The Chemistry of Silica: Solubility, Polymerization, Colloid and Surface Properties, and Biochemistry.* John Wiley & Sons, New York, 1979.
Imagawa et al., "Transcription factor AP-2 mediates induction by two different signal-transduction pathways: Protein kinase C and cAMP" *Cell* 1987, 51(2), 251-260.
Imbra et al., "Phorbol ester induces the transcriptional stimulatory activity of the SV40 enhancer" *Nature* 1986, 323, 555-558.
Imler et al., "Negative Regulation Contributes to Tissue Specificity of the Immunoglobulin Heavy-Chain Enhancer" *Molecular and Cellular Biology* 1987, 7(7), 2558-2567.
Imperiale et al., "Common Control of the Heat Shock Gene and Early Adenovirus Genes: Evidence for a Cellular E1A-like Activity" *Molecular and Cellular Biology* 1984, 4(5), 867-874.
International Search Report and Written Opinion issued in Corresponding PCT Application No. PCT/US2019/020685, dated Jun. 11, 2019.

(56) References Cited

OTHER PUBLICATIONS

International Search Report and Written Opinion issued in Corresponding PCT Application No. PCT/US2020/070113, dated Sep. 10, 2020.
International Search Report and Written Opinion issued in Corresponding PCT Application No. PCT/US2020/070308, dated Nov. 5, 2020.
International Search Report and Written Opinion Issued in Corresponding PCT Patent Application No. PCT/US2018/028505, mailed Jul. 24, 2018.
Ishihara et al., "Matrix-binding checkpoint immunotherapies enhance antitumor efficacy and reduce adverse events" Sci Transl Med 2017, 9(415), eaan0401, 16 pages.
Jakobovits et al., "A discrete element 3' of human immunodeficiency virus 1 (HIV-1) and HIV-2 mRNA initiation sites mediates transcriptional activation by an HIV trans activator." *Molecular and Cellular Biology* 1988, 8(6), 2555-2561.
Jameel et al., "The Human Hepatitis B Virus Enhancer Requires trans-Acting Cellular Factor(s) for Activity" *Molecular and Cellular Biology* 1986, 6(2), 710-715.
Jaynes et al., "The Muscle Creatine Kinase Gene Is Regulated by Multiple Upstream Elements, Including a Muscle-Specific Enhancer" *Molecular and Cellular Biology* 1988, 8(1), 62-70.
Jiang et al., "Role of IL-2 in cancer immunotherapy" *Oncoimmunology* 2016, 5(6), e1163462, 10 pages.
Johnson et al., "Muscle Creatine Kinase Sequence Elements Regulating Skeletal and Cardiac Muscle Expression in Transgenic Mice" *Molecular and Cellular Biology* 1989, 9(8), 3393-3399.
Kadesch et al., "Effects of the position of the simian virus 40 enhancer on expression of multiple transcription units in a single plasmid." *Molecular and Cellular Biology* 1986, 6(7), 2593-2601.
Karin et al., "Metal-Responsive Elements Act as Positive Modulators of Human Metallothionein-II$_A$ Enhancer Activity" *Molecular and Cellular Biology* 1987, 7(2), 606-613.
Katinka et al., "Expression of polyoma early functions in mouse embryonal carcinoma cells depends on sequence rearrangements in the beginning of the late region" *Cell* 1980, 20(2), 393-399.
Katinka et al., "Polyoma DNA sequences involved in control of viral gene expression in murine embryonal carcinoma cells" *Nature* 1981, 290, 720-722.
Kawamoto et al., "DNA bending and binding factors of the human ß-actin promoter" *Nucleic Acids Research* 1989, 17(2), 523-537.
Kiledjian et al., "Identification and Characterization of Two Functional Domains within the Murine Heavy-Chain Enhancer" *Molecular and Cellular Biology* 1988, 8(1), 145-152.
Klamut et al., "Molecular and Functional Analysis of the Muscle-Specific Promoter Region of the Duchenne Muscular Dystrophy Gene" *Molecular and Cellular Biology* 1990, 10(1), 193-205.
Koch et al., "Anatomy of a New B-Cell-Specific Enhancer" *Molecular and Cellular Biology* 1989, 9(1), 303-311.
Kratz et al., "Probing the Cysteine-34 Position of Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound" *J. Med. Chem.* 2002, 45, 5523-5533.
Kriegler et al., "A novel form of TNF/cachectin is a cell surface cytotoxic transmembrane protein: ramifications for the complex physiology of TNF" *Cell* 1988, 53, 45-53.
Kriegler et al., "Enhanced Transformation by a Simian Virus 40 Recombinant Virus Containing a Harvey Murine Sarcoma Virus Long Terminal Repeat" *Molecular and Cellular Biology* 1983, 3(3), 325-339.
Kriegler et al., "Partial purification and characterization of a growth factor for macrophage progenitor cells with high proliferative potential in mouse bone marrow" *Blood* 1982, 60, 503-508.
Kriegler et al., "Transformation mediated by the SV40 T antigens: Separation of the overlapping SV40 early genes with a retroviral vector" *Cell* 1984, 38(2), 483-491.
Kuhl et al., "Reversible silencing of enhancers by sequences derived from the human IFN-α promoter" *Cell* 1987, 50(7), 1057-1069.

Kunz et al., "Identification of the promoter sequences involved in the interleukin-6 dependent expression of the rat $\alpha_2$-macroglobulin gene" *Nucleic Acids Research* 1989, 17(3), 1121-1138.
Larsen et al., "Sequences Required for Cell-type Specific Thyroid Hormone Regulation of Rat Growth Hormone Promoter Activity" *The Journal of Biological Chemistry* 1986, 261(31), 14373-14376.
Laspia et al., "HIV-1 Tat protein increases transcriptional initiation and stabilizes elongation" *Cell* 1989, 50(2), 283-92.
Latimer et al., "Highly Conserved Upstream Regions of the $\alpha_1$-Antitrypsin Gene in Two Mouse Species Govern Liver-Specific Expression by Different Mechanisms" *Molecular and Cellular Biology* 1990, 10(2), 760-769.
Lee et al., "Functional analysis of the steroid hormone control region of mouse mammary tumor virus" *Nucleic Acids Research* 1984, 12(10), 4191-4206.
Lee et al., "Glucocorticoids regulate expression of dihydrofolate reductase cDNA in mouse mammary tumour virus chimaeric plasmids" *Nature* 1981, 294, 228-232.
Lenting et al., "von Willebrand factor: the old, the new and the unknown" *Journal of Thrombosis and Haemostasis: JTH* 2012, 1,: 2428-2437.
Levinson et al., "Activation of SV40 genome by 72-base pair tandem repeats of Moloney sarcoma virus" *Nature* 1982, 295, 568-572.
Liang et al., "A collagen-binding EGFR antibody fragment targeting tumors with a collagen-rich extracellular matrix" *Scientific Reports* 2016, 6:18205, 14 pages.
Liang et al., "A collagen-binding EGFR single- chain Fv antibody fragment for the targeted cancer therapy" *Journal of controlled release* 2015, 209, 101-109.
Lin et al., "CCL21 Cancer Immunotherapy" *Cancers* 2014, 6, 1098-110.
Lin et al., "Delineation of an Enhancerlike Positive Regulatory Element in the Interleukin-2 Receptor α-Chain Gene" *Molecular and Cellular Biology* 1990, 10(2), 850-853.
Lu et al., "The extracellular matrix: A dynamic niche in cancer progression" *The Journal of Cell Biology* 2012, 196(4), 395-406.
Luheshi, et al., "Transformation of the Tumour Microenvironment by a CD40 Agonist Antibody Correlates with Improved Responses to DL-L 1 Blockade in a Mouse Orthotopic Pancreativ Tumour Model," *Oncotarget*, 7(14): 18508-18520, 2016.
Lund et al., "VEGF-C Promotes Immune Tolerance in B16 Melanomas and Cross-Presentation of Tumor Antigen by Lymph Node Lymphatics" *Cell Rep* 2012, 1, 191-99.
Luria et al., "Promoter and enhancer elements in the rearranged alpha chain gene of the human T cell receptor." *The EMBO Journal* 1987, 6(11), 3307-3312.
Lusky et al., "Bovine Papilloma Virus Contains an Activator of Gene Expression at the Distal End of the Early Transcription Unit" *Molecular and Cellular Biology* 1983, 3(6), 1108-1122.
Lusky et al., "Transient replication of bovine papilloma virus type 1 plasmids: cis and trans requirements" *Proc. Nadl. Acad. Sci. USA* 1986, 83, 3609-3613.
Maeda et al., "Tumor vascular permeability and the EPR effect in macromolecular therapeutics: a review" *Journal of Controlled Release* 2000, 65, 271-284.
Majors et al., "A small region of the mouse mammary tumor virus long terminal repeat confers glucocorticoid hormone regulation on a linked heterologous gene" *Proc. Natl. Acad. Sci. USA* 1983, 80, 5866-5870.
Martinelli et al., "Anti-epidermal growth factor receptor monoclonal antibodies in cancer therapy" *Clin Exp Immunol* 2009, 158, 1-9.
Martino et al., "Growth Factors Engineered for Super-Affinity to the Extracellular Matrix Enhance Tissue Healing" *Science* 2014, 343, 885-888.
Matsui et al. "Interaction of von Willebrand Factor with the Extracellular Matrix and Glycocalicin under Static Conditions," *Journal of Biochemistry* 1997, 121(2), 376-381.
Matsumura, Y. & Maeda, H., "A new concept for macromolecular therapeutics in cancer chemotherapy: mechanism of tumoritropic accumulation of proteins and the antitumor agent smancs." *Cancer Res.* 1986, 46, 6387-6392.

(56) References Cited

OTHER PUBLICATIONS

McNeall et al., "Hyperinducible gene expression from a metallothionein promoter containing additional metal-responsive elements" *Gene* 1989, 76(1), 81-88.
Miksicek et al., "Glucocorticoid responsiveness of the transcriptional enhancer of Moloney Murine Sarcoma Virus" *Cell* 1986, 46(2), 283-290.
Mordacq et al., "Co-localization of elements required for phorbol ester stimulation and glucocorticoid repression of proliferin gene expression" *Genes & Development* 1989, 3, 760-769.
Moreau et al., "The SV40 72 base repair repeat has a striking effect on gene expression both in SV40 and other chimeric recombinants" *Nucleic Acids Research* 1981, 9(22), 6047-6068.
Muesing et al., "Regulation of mRNA accumulation by a human immunodeficiency virus trans-activator protein" *Cell* 1987, 48(4), 691-701.
Nagy et al., "Why are tumour blood vessels abnormal and why is it important to know?" *British Journal of Cancer* 2009, 100, 865-869.
Ng et al., "Regulation of the human β-actin promoter by upstream and intron domains" *Nucleic Acids Research* 1989, 17(2), 601-615.
Ondek et al., "Discrete elements within the SV40 enhancer region display different cell-specific enhancer activities." *EMBO J* 1987, 6, 1017-1025.
Ornitz et al., "Promoter and Enhancer Elements from the Rat Elastase I Gene Function Independently of Each Other and of Heterologous Enhancers" *Molecular and Cellular Biology* 1987, 7(10), 3466-3472.
Palmiter et al., "Dramatic growth of mice that develop from eggs microinjected with metallothionein-growth hormone fusion genes" *Nature* 1982, 300, 611-615.
Partch et al., "Aerosol and Solution Modification of Particle-Polymer Interfaces" *The Journal of Adhesion* 1998, 67, 259-276.
Pech et al., "Functional Identification of Regulatory Elements within the Promoter Region of Platelet-Derived Growth Factor 2" *Molecular and Cellular Biology* 1989, 9(2), 396-405.
Pekarek et al., "One-step preparation of double-walled microsphere" *Advanced Materials* 1994, 6(9).
Perez-Stable et al., "Roles of Fetal $^{G}$γ-Globin Promoter Elements and the Adult β- Globin 3' Enhancer in the Stage-Specific Expression of Globin Genes" *Molecular and Cellular Biology* 1990, 10(3), 1116-1125.
Picard et al., "A lymphocyte-specific enhancer in the mouse immunoglobulin κ gene" *Nature* 1984, 307, 80-82.
Pinkert et al., "An albumin enhancer located 10 kb upstream functions along with its promoter to direct efficient, liver-specific expression in transgenic mice" *Genes & Development* 1987, 1, 268-276.
Ponta et al., "Hormonal response region in the mouse mammary tumor virus long terminal repeat can be dissociated from the proviral promoter and has enhancer properties" *Proc. Natl. Acad. Sci. USA* 1985, 82, 1020-1024.
Porton et al., "Immunoglobulin Heavy-Chain Enhancer Is Required To Maintain Transfected y2A Gene Expression in a Pre-B-Cell Line" *Molecular and Cellular Biology* 1990, 10(3), 1076-1083.
Provenzano et al., "Collagen density promotes mammary tumor initiation and progression" *BMC Med* 2008, 6(11), 15 pages.
Puskas et al. "Development of an Attenuated Interleukin-2 Fusion Protein that can be Activated by Tumour-Expressed Proteases," *Immunology* 2011, vol. 133 No. 2, pp. 206-220.
Queen et al., "Immunoglobulin gene transcription is activated by downstream sequence elements" *Cell* 1983, 33(3), 741-748.
Quinn et al., "Distinct Factors Bind the AP-1 Consensus Sites in Gibbon Ape Leukemia Virus and Simian Virus 40 Enhancers" *Journal of Virology* 1989, 63(4), 1737-1742.
Redondo et al., "A T cell-specific transcriptional enhancer within the human T cell receptor delta locus" *Science* 1990, 247(4947), 1225-1229.
Reisman et al., "Induced Expression from the Moloney Murine Leukemia Virus Long Terminal Repeat during Differentiation of Human Myeloid Cells Is Mediated through Its Transcriptional Enhancer" *Molecular and Cellular Biology* 1989, 9(8), 3571-3575.
Resendez et al., "Identification of Highly Conserved Regulatory Domains and Protein-Binding Sites in the Promoters of the Rat and Human Genes Encoding the Stress- Inducible 78-Kilodalton Glucose-Regulated Protein" *Molecular and Cellular Biology* 1988, 8(10), 4579-4584.
Ribba et al., "Ser968Thr Mutation within the A3 Domain of Von Willebrand Factor (VWF) in Two Related Patients Leads to a Defective Binding of VWF to Collagen" *Thrombosis and haemostasis* 2001, 86, 848-54.
Rittling et al., "AP-1/jun binding sites mediate serum inducibility of the human vimentin promoter" *Nucleic Acids Research* 1989, 17(4), 1619-1633.
Rosen et al., "Intragenic cis-acting art gene-responsive sequences of the human immunodeficiency virus" *Proc. Natl. Acad. Sci. USA* 1988, 85, 2071-2075.
Rosenberg et al., "Observations on the Systemic Administration of Autologous Lymphokine-Activated Killer Cells and Recombinant Interleukin-2 to Patients with Metastatic Cancer" *N Engl J Med* 1985, 313, 1485-1492.
Rybak et al., "The extra-domain A of fibronectin is a vascular marker of solid tumors and metastases" *Cancer Res.* 2007, 67, 10948-957.
Sakai et al., "Hormone-mediated repression: a negative glucocorticoid response element from the bovine prolactin gene" *Genes & Development* 1988, 2, 1144-115.
Satake et al., "Modulation of polyomavirus enhancer binding proteins by Ha-ras oncogene" *Oncogene* 1988, 3(1), 69-78.
Schaffner et al., "Redundancy of information in enhancers as a principle of mammalian transcription control" *Journal of Molecular Biology* 1988, 201(1), 81-90.
Searle et al., "Building a Metal-Responsive Promoter with Synthetic Regulatory Elements" *Molecular and Cellular Biology* 1985, 5(6), 1480-1489.
Shahidi, M., "Thrombosis and von Willebrand Factor" *Advances in experimental medicine and biology* 2017, 906, 285-306.
Shaul et al., "Multiple nuclear proteins in liver cells are bound to hepatitis B virus enhancer element and its upstream sequences." *EMBO J* 1987, 6, 1913-1920.
Sherman et al., "The octamer motif is a B-lymphocyte-specific regulatory element of the HLA-DRα gene promoter" *Proc. Natl. Acad. Sci. USA* 1989, 86, 6739-6743.
Skrombolas et al. "Development of an Interleukin-12 Fusion Protein That Is Activated by Cleavage with Matrix Metalloproteinase 9," *Journal of Interferon and Cytokine Research*, 2019, vol. 39, Iss. 4, pp. 233-245.
Sleigh et al., "SV40 enhancer activation during retinoic acid-induced differentiation of F9 embryonal carcinoma cells" *EMBO J* 1985, 4, 3831-3837.
Spalholz et al., "Transactivation of a bovine papilloma virus transcriptional regulatory element by the E2 gene product" *Cell* 1985, 42(1), 183-191.
Spandau et al., "trans-Activation of Viral Enhancers by the Hepatitis B Virus X Protein" *Journal of Virology* 1988, 62(2), 427-434.
Spandidos and Wilkie, "Host-specificities of papillomavirus, Moloney murine sarcoma virus and simian virus 40 enhancer sequences." *EMBO J* 1983, 2, 1193-1199.
Spranger, et al., "Melanoma-Intrinsic Beta-Catenin Signalling Prevents Anti-Tumour Immunity," *Nature*, 523(7559): 231-235, 2015.
Stephens et al., "The bovine papillomavirus genome and its uses as a eukaryotic vector" *Biochem J* 1987, 248(1), 1-11.
Storz, U., "Intellectual property issues of immune checkpoint inhibitors" *mAbs* 2016, 8(1), 10-26.
Stuart et al., "Identification of multiple metal regulatory elements in mouse metallothionein-I promoter by assaying synthetic sequences" *Nature* 1985, 317, 828-831.
Sukhorukov et al. "Layer-by-layer self-assembly of polyelectrolytes on colloidal particles" *Colloids and Surfaces A: Physicochemical and Engineering Aspects* 1998, 137, 253-266.
Sullivan, Kate E. and B. Matija Peterlin, "Transcriptional Enhancers in the HLA-DQ Subregion" *Molecular and Cellular Biology* 1987, 7(9), 3315-3319.

(56) References Cited

OTHER PUBLICATIONS

Swartz et al., "Interstitial Flow and Its Effects in Soft Tissues" *Annu Rev Biomed Eng* 2007, 9, 229-56.

Swartz et al., "Lymphatic and interstitial flow in the tumour microenvironment: linking mechanobiology with immunity." *Nat Rev Cancer* 2012, 12, 210-19.

Swartzendruber et al., "Neoplastic differentiation: Interaction of simian virus 40 and polyoma virus with murine teratocarcinoma cells in vitro" *Journal of Cellular Physiology* 1975, 85(2), 179-187.

Takebe et al., "SR alpha promoter: an efficient and versatile mammalian cDNA expression system composed of the simian virus 40 early promoter and the R-U5 segment of human T-cell leukemia virus type 1 long terminal repeat." *Molecular and Cellular Biology* 1988, 8(1), 466-472.

Tavernier et al., "Deletion mapping of the inducible promoter of human IFN-β gene" *Nature* 1983, 301, 634-636.

Taylor et al., "E1a Transactivation of Human HSP70 Gene Promoter Substitution Mutants Is Independent of the Composition of Upstream and TATA Elements" *Molecular and Cellular Biology* 1990, 10(1), 176-183.

Taylor et al., "Factor Substitution in a Human HSP70 Gene Promoter: TATA Dependent and TATA-Independent Interactions" *Molecular and Cellular Biology* 1990, 10(1), 165-175.

Taylor et al., "Stimulation of the Human Heat Shock Protein 70 Promoter in Vitro by Simian Virus 40 Large T Antigen" *The Journal of Biological Chemistry* 1989, 264(27), 16160-16164.

Thiesen et al., "A Dna Element Responsible for the Different Tissue Specificities of Friend and Moloney Retroviral Enhancers" *Journal of Virology* 1988, 62(2), 614-618.

Tokunaga et al., "CXCL9, CXCL10, CXCL11/CXCR3 axis for immune activation—A target for novel cancer therapy" *Cancer Treatment Reviews* 2017, 63, 40-47.

Treisman, Richard, "Identification of a protein-binding site that mediates transcriptional response of the c-fos gene to serum factors" *Cell* 1986, 46(4), 567-574.

Tronche et al., "The Rat Albumin Promoter: Cooperation with Upstream Elements Is Required when Binding of APF/HNF1 to the Proximal Element Is Partially Impaired by Mutation or Bacterial Methylation" *Molecular and Cellular Biology* 1989, 9(11), 4759-4766.

Trudel et al., "A 3' enhancer contributes to the stage-specific expression of the human β-globin gene" *Genes & Development* 1987, 1, 954-961.

Tyndall et al., "A region of the polyoma virus genome between the replication origin and late protein coding sequences is required in cis for both early gene expression and viral DNA replication" *Nucleic Acids Research* 1981, 9(23), 6231-6250.

Vannice et al., "Properties of the Human Hepatitis B Virus Enhancer: Position Effects and Cell-Type Nonspecificity" *Journal of Virology* 1988, 62(4), 1305-1313.

Vasseur et al., "Isolation and characterization of polyoma virus mutants able to develop in embryonal carcinoma cells" *Proc. Natl. Acad. Sci. USA* 1980, 77(2), 1068-1072.

Villa et al., "A high-affinity human monoclonal antibody specific to the alternatively spliced EDA domain of fibronectin efficiently targets tumor neo-vasculature in vivo" *Int. J Cancer* 2008, 122, 2405-13.

Waldmann, Thomas A., "The biology of interleukin-2 and interleukin-15: implications for cancer therapy and vaccine design" *Nature Reviews Immunology* 2006, 6, 595-601.

Wang et al., "SV40 enhancer-binding factors are required at the establishment but not the maintenance step of enhancer-dependent transcriptional activation" *Cell* 1986 47(2), 241-247.

Weber et al., "An SV40 "enhancer trap" incorporates exogenous enhancers or generates enhancers from its own sequences" *Cell* 1984, 36(4), 983-992.

Weinberger et al., "Distinct factors bind to apparently homolgous sequences in the immunoglobulin heavy-chain enhancer" *Nature* 1986.

Wilson, D. S. et al., "Antigens reversibly conjugated to a polymeric glyco-adjuvant induce protective humoral and cellular immunity" *Nat. Mater.* 2019, 18, 175-185.

Winoto, Astar and David Baltimore, "A novel, inducible and Tcell-specific enhancer located at the 3' end of the T cell receptor a locus" *The EMBO Journal* 1989, 8(3), 729-733.

Wu et al., "Inhibition of the von Willebrand (VWF)-collagen interaction by an antihuman VWF monoclonal antibody results in abolition of in vivo arterial platelet thrombus formation in baboons" *Blood* 2002, 99(10), 3623-28.

Xiong et al. "Function of cancer cell-derived extracellular matrix in tumor progression" *Journal of Cancer Metastasis and Treatment* 2016, 2, 357-64.

Xu et al., "Proteolytic exposure of a cryptic site within collagen type IV is required for angiogenesis and tumor growth in vivo" *The Journal of Cell Biology* 2001, 154, 1069-80.

Yasunaga et al., "Cancer-Stroma Targeting Therapy by Cytotoxic Immunoconjugate Bound to the Collagen 4 Network in the Tumor Tissue" *Bioconjugate Chem.* 2011, 22, 1776-83.

Yin et al., "Antitumor potential of a synthetic interferon-alpha/PLGF-2 positive charge peptide hybrid molecule in pancreatic cancer cells" *Scientific Reports* 2015, 5:16975, 13 pages.

Yonezawa et al., "Boosting Cancer Immunotherapy with Anti-CD137 Antibody Therapy" *Clinical Cancer Research* 2015, 21 (14), 3113-3120.

Yutzey et al., "An Internal Regulatory Element Controls Troponin I Gene Expression" *Molecular and Cellular Biology* 1989, 9(4), 1397-1405.

Zhou et al., "Reorganized Collagen in the Tumor Microenvironment of Gastric Cancer and Its Association with Prognosis" *J Cancer* 2017, 8, 1466-76.

Zhu et al., "Synergistic Innate and Adaptive Immune Response to Combination Immunotherapy with Anti-Tumor Antigen Antibodies and Extended Serum Half-Life IL-2" *Cancer Cell* 2015, 27, 489-501.

Bhatia et al., "Targeting advanced prostate cancer with STEAP1 chimeric antigen receptor T cell and tumor-localized IL-12 immunotherapy," *Nature Communications,* 14(1):2041, pp. 1-23, 2023.

Mansurov et al., "Collagen-binding II-12 enhances tumour inflammation and drives the complete remission of established 'immunologically cold' murine tumours," *Nat. Biomed. Eng.,* 4(5):531-543, 2020.

Williford et al., "Recruitment of CD103+ DCs via tumor stroma-targeted chemokine delivery enhances efficacy of checkpoint inhibitor immunotherapy," Journal for Immunotherapy of Cancer, Abstract No. P261, vol. 7, No. S1:282; Nov. 2019. pp. 139-140.

Halin et al., "Enhancement of the antitumor activity of interleukin-12 by targeted delivery to neovasculature", Nature Biotechnology, 20(3):264-269, 2002.

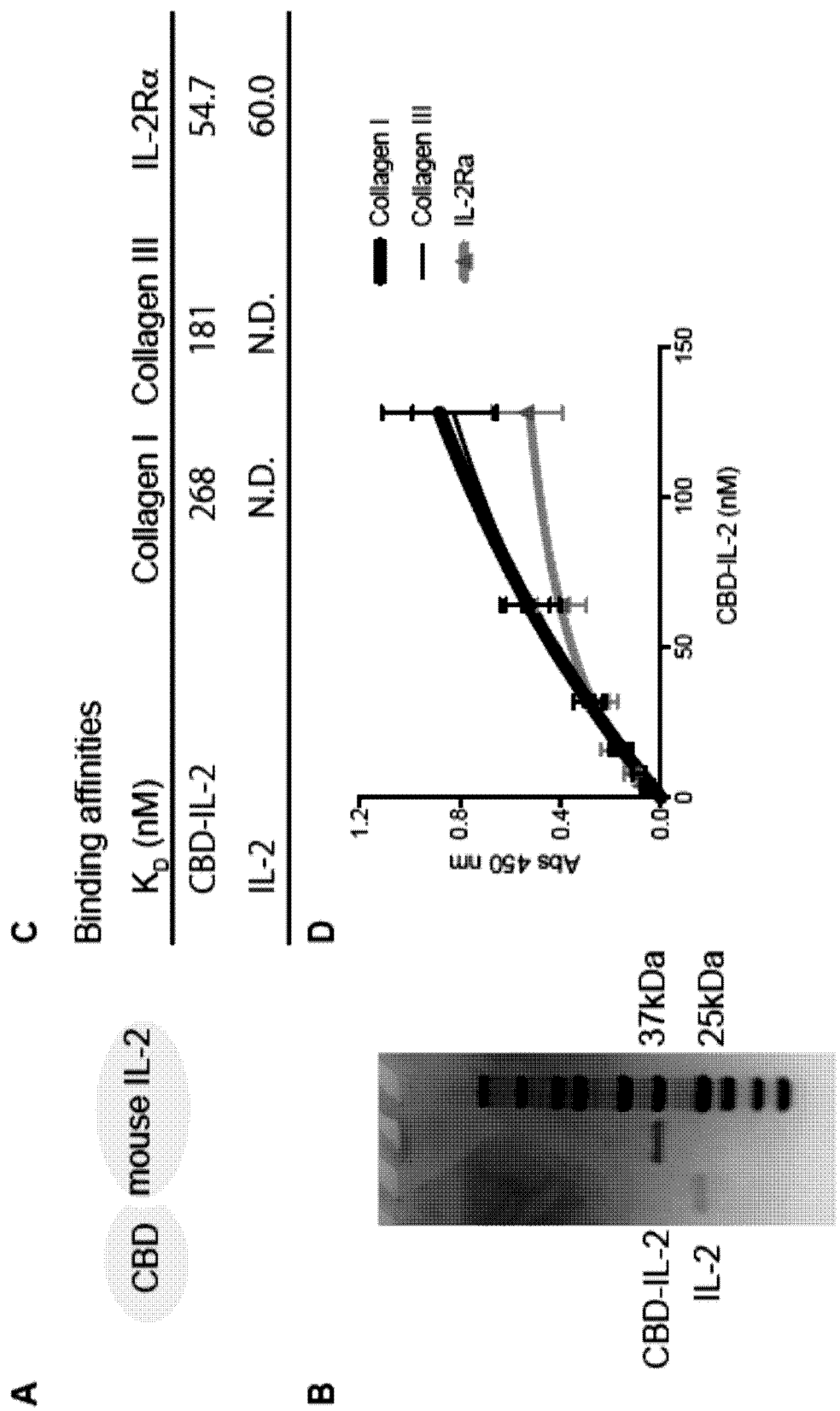
FIG. 1A-D

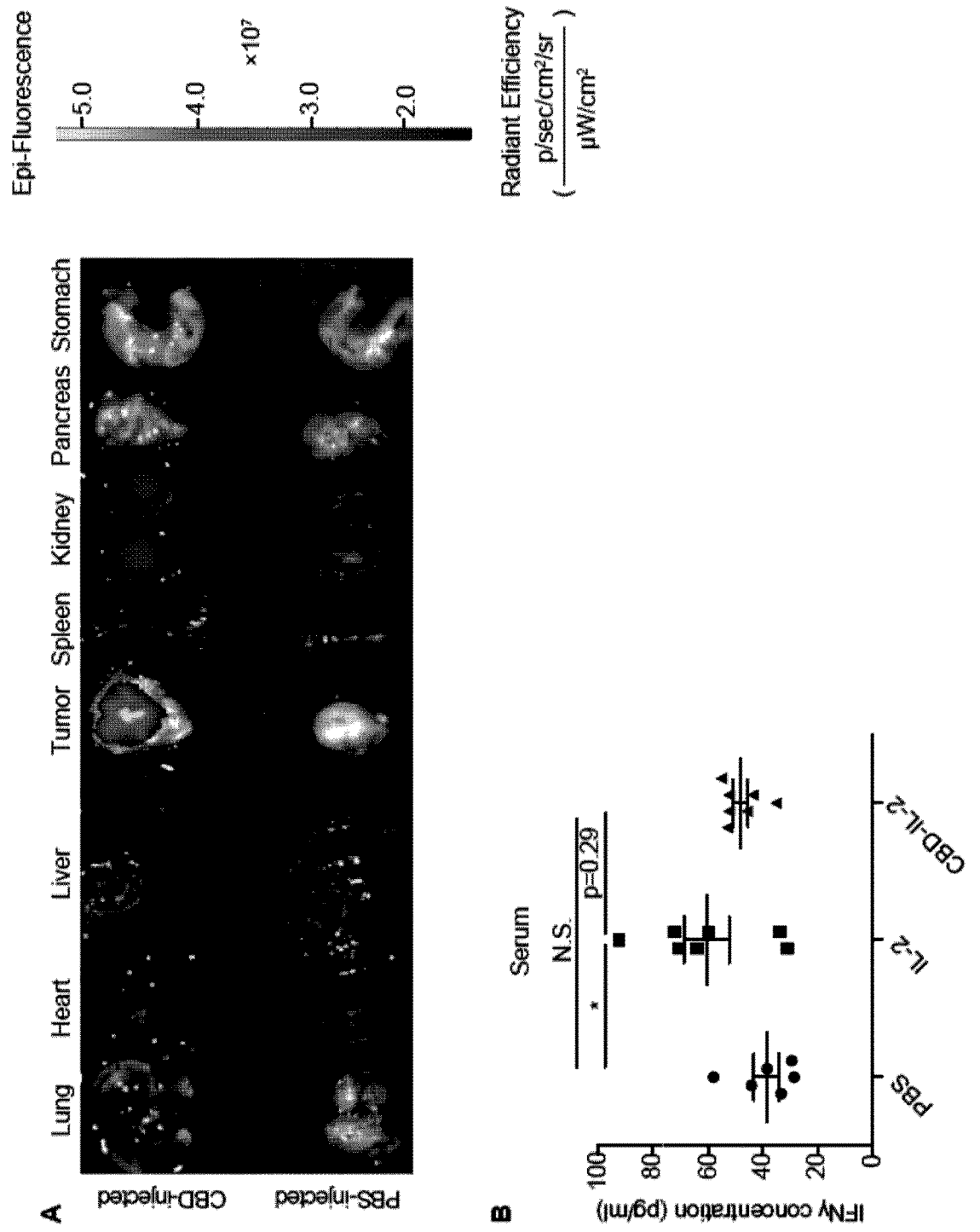
FIG. 2A-B

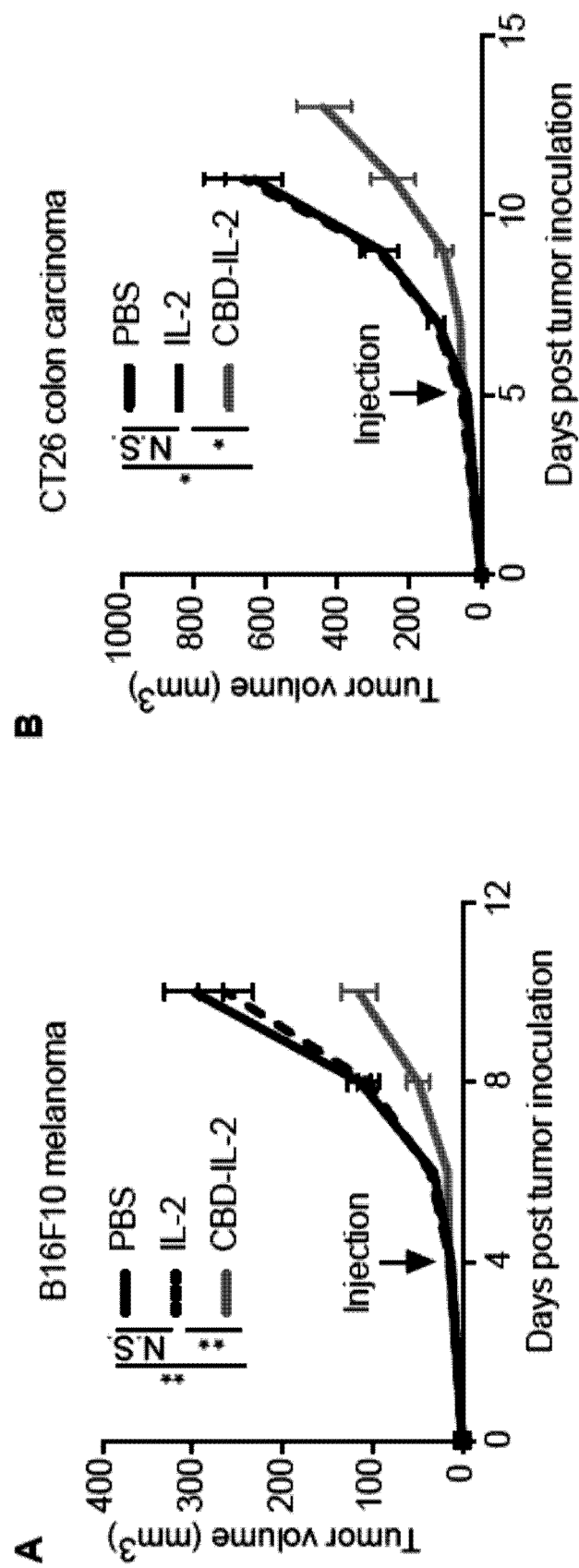
FIG. 3A-B

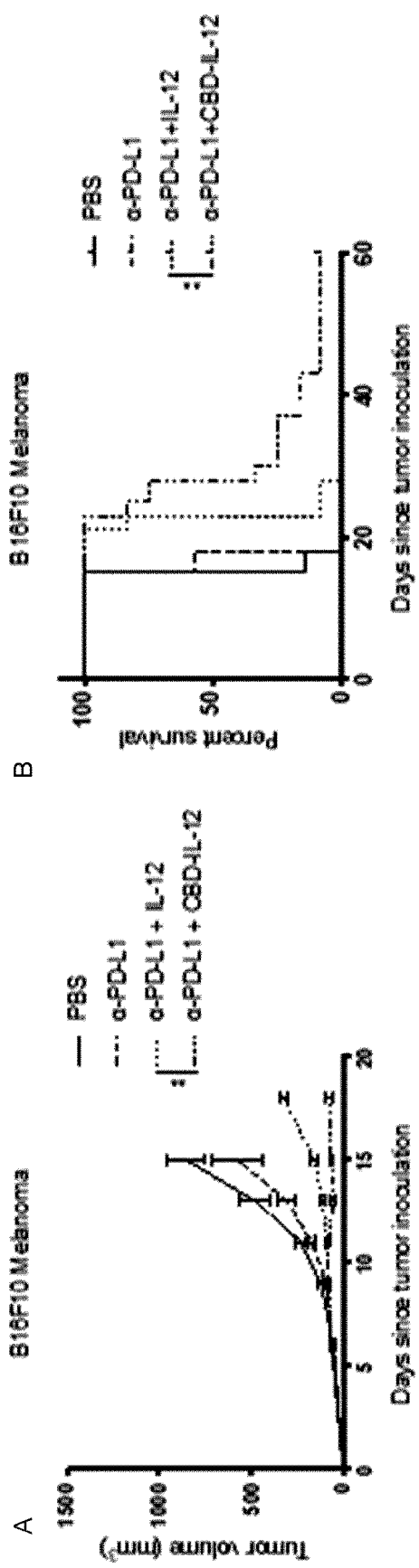
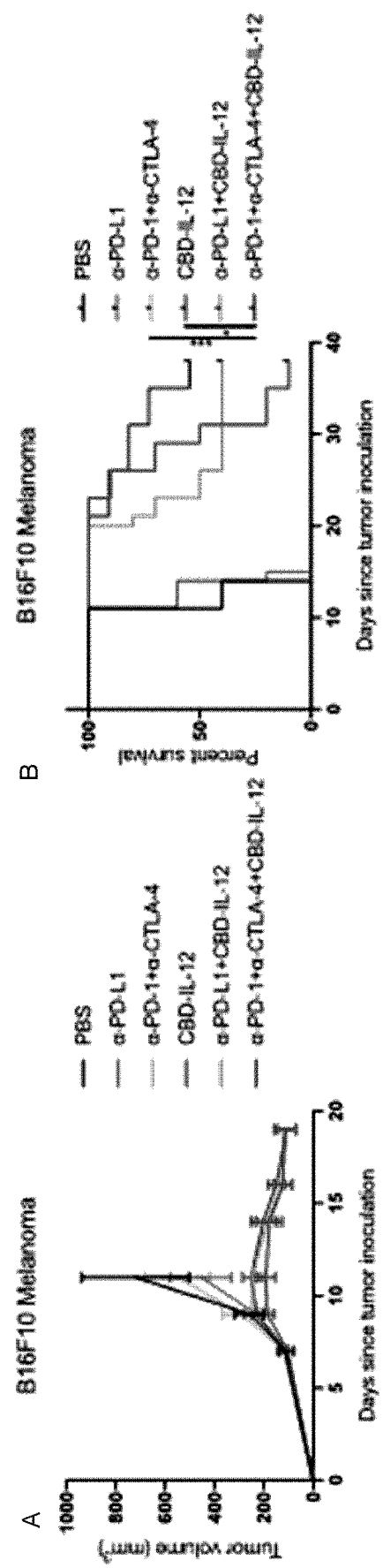
FIG. 4A-B
FIG. 5A-B

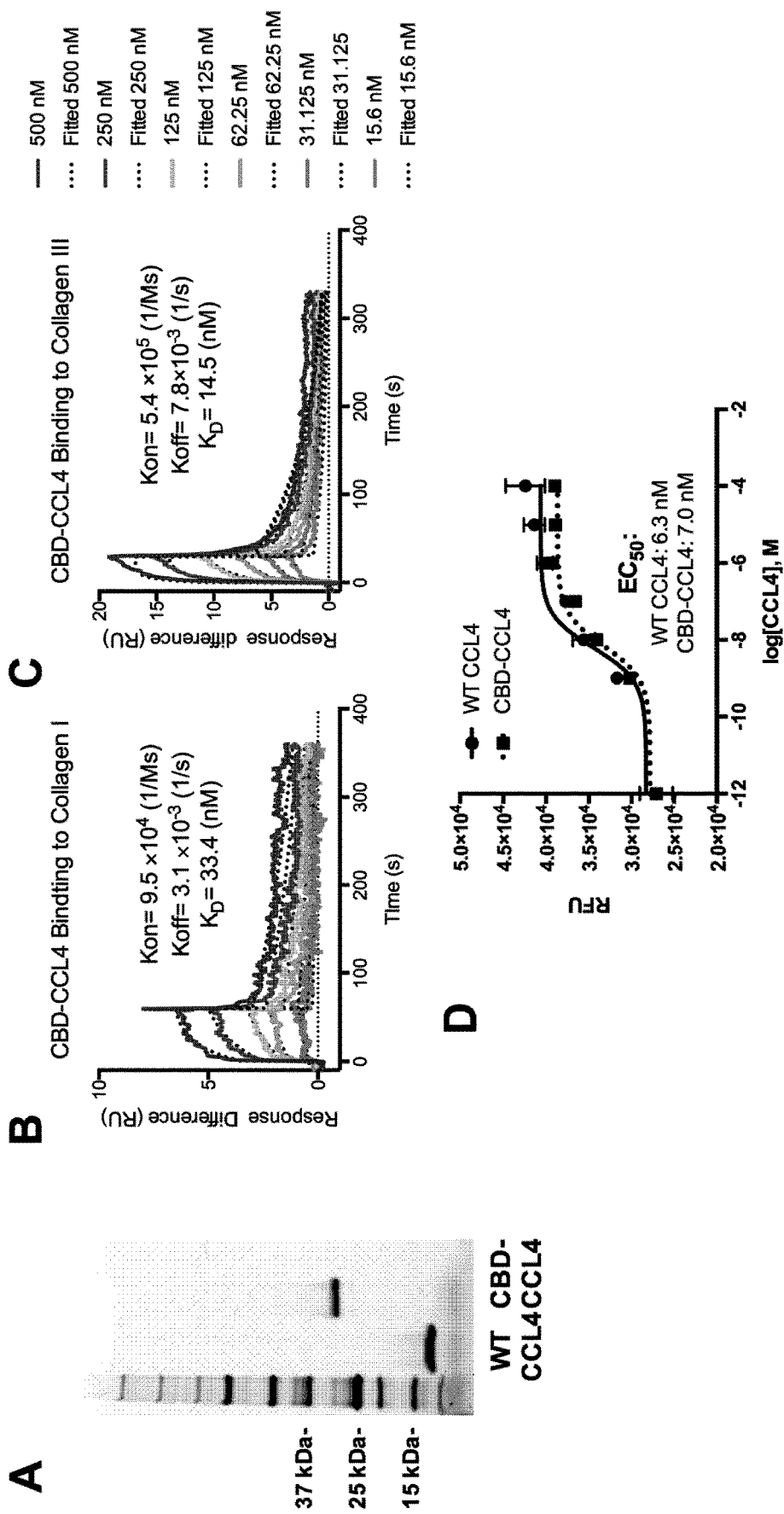
FIG. 6A-D

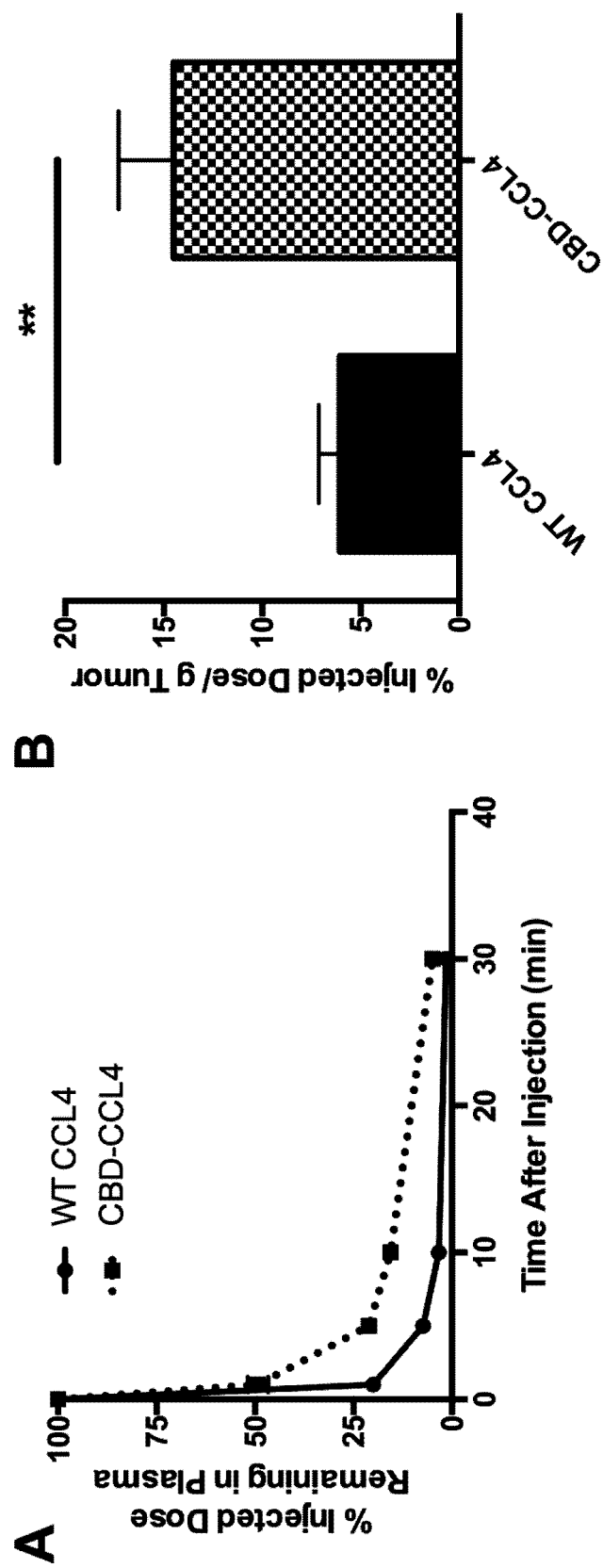
FIG. 7A-B

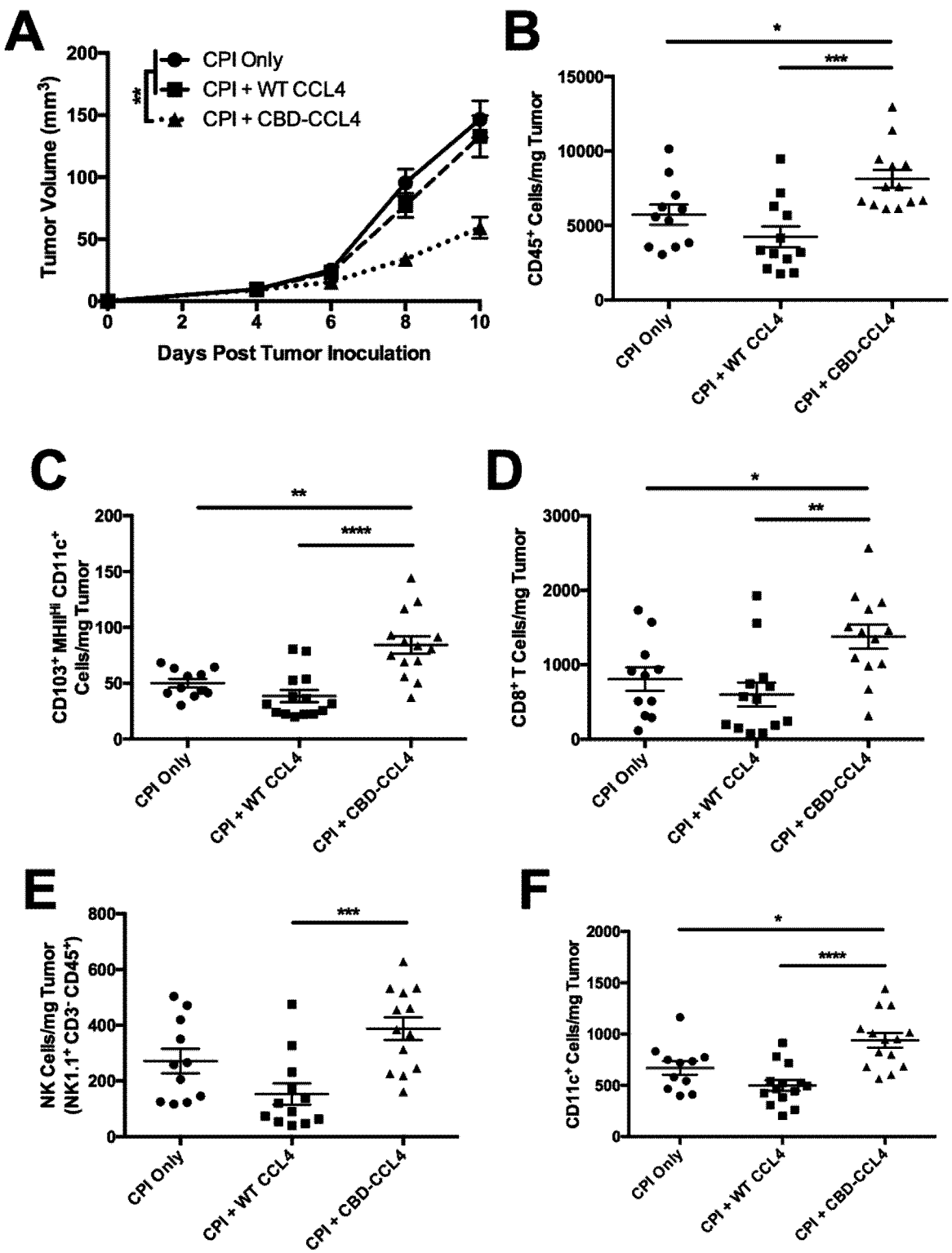
FIG. 8A-F

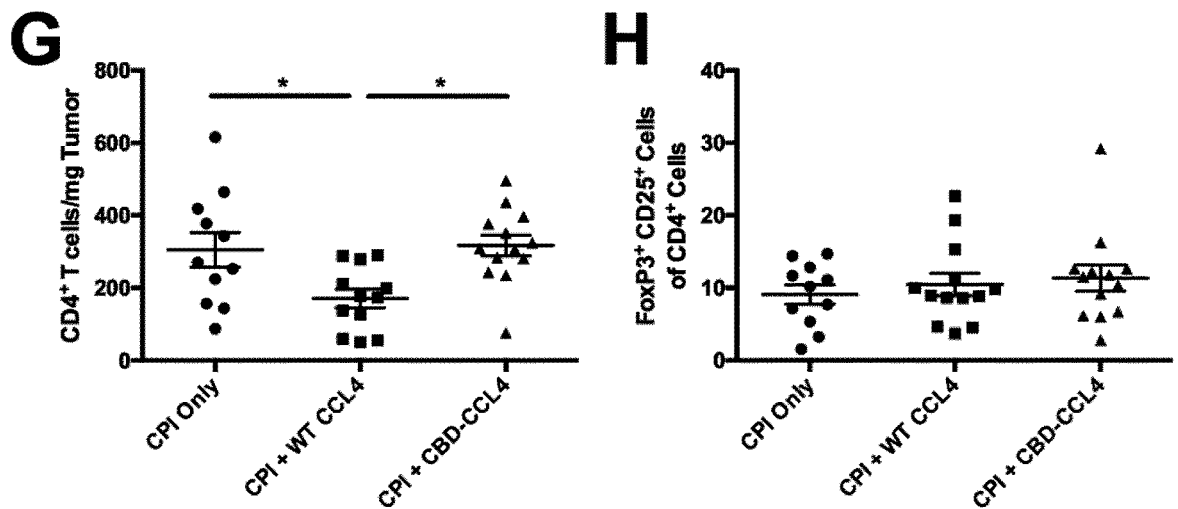
FIG. 8G-H
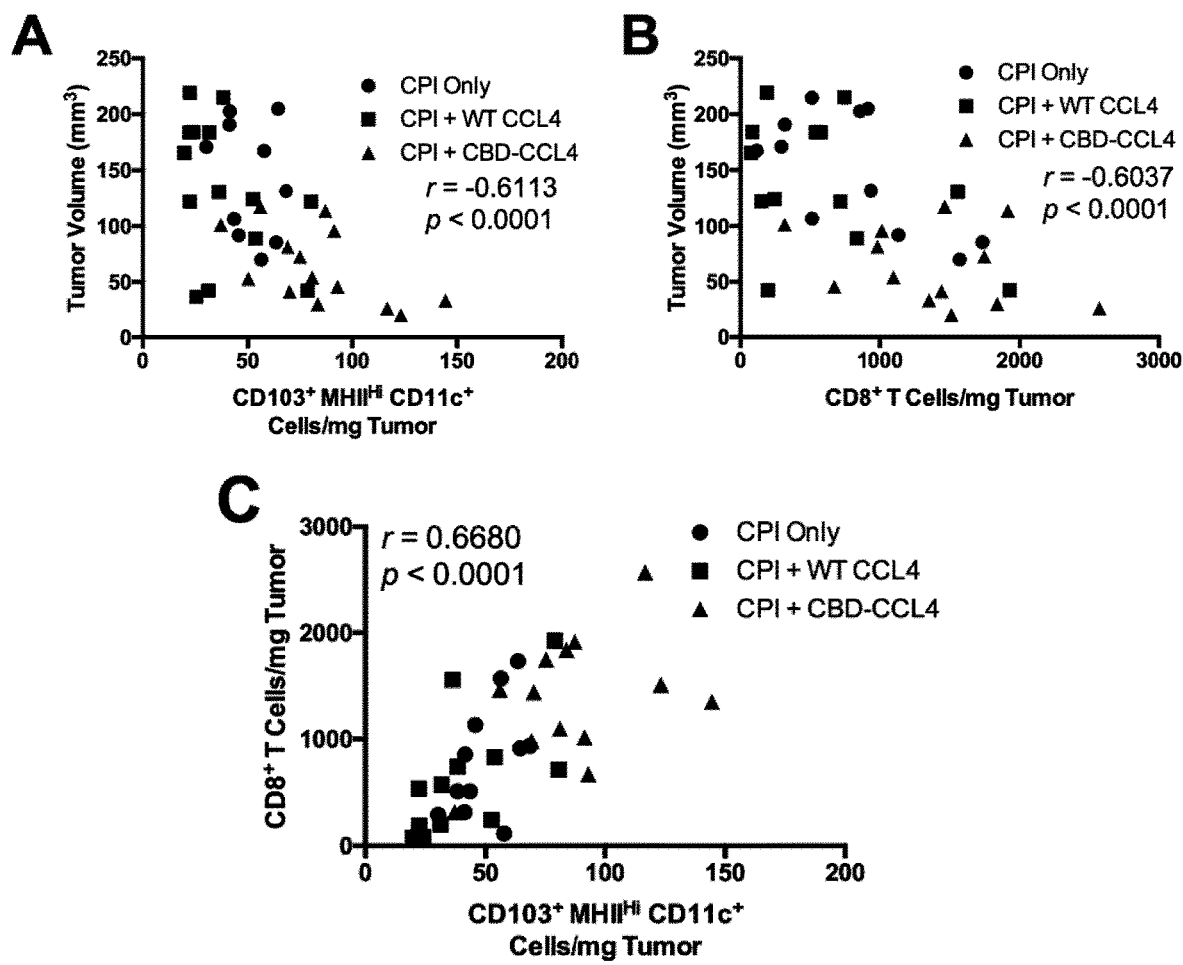
FIG. 9A-C

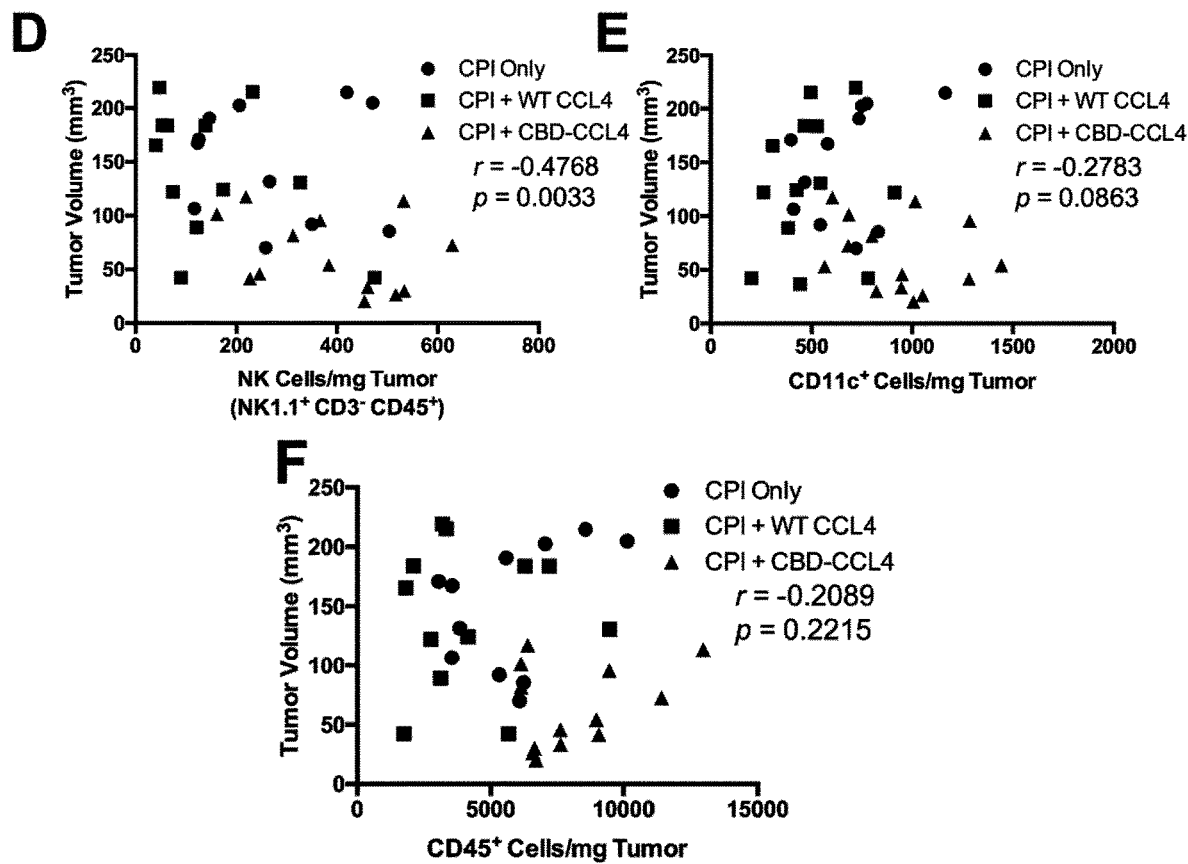
FIG. 9D-F
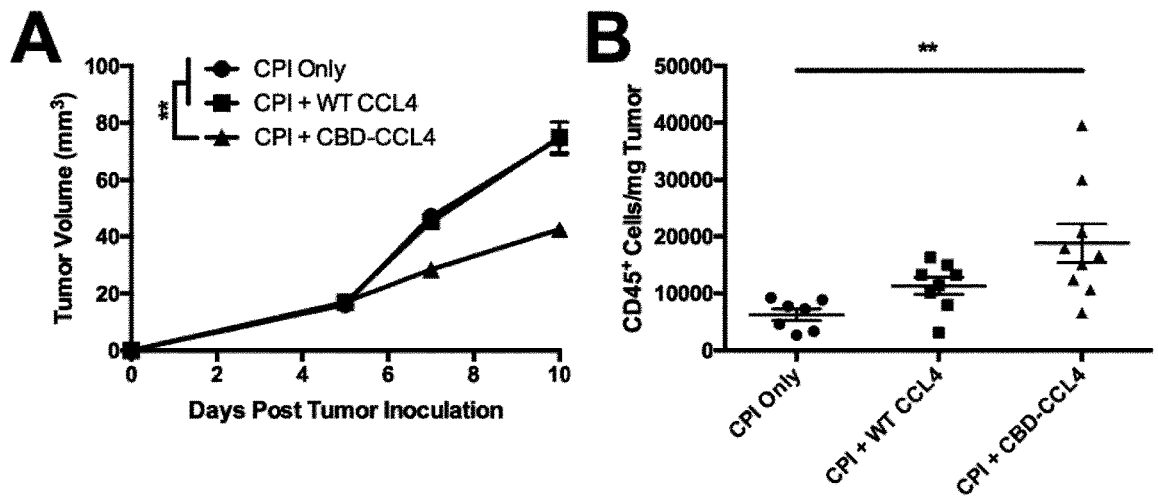
FIG. 10A-B

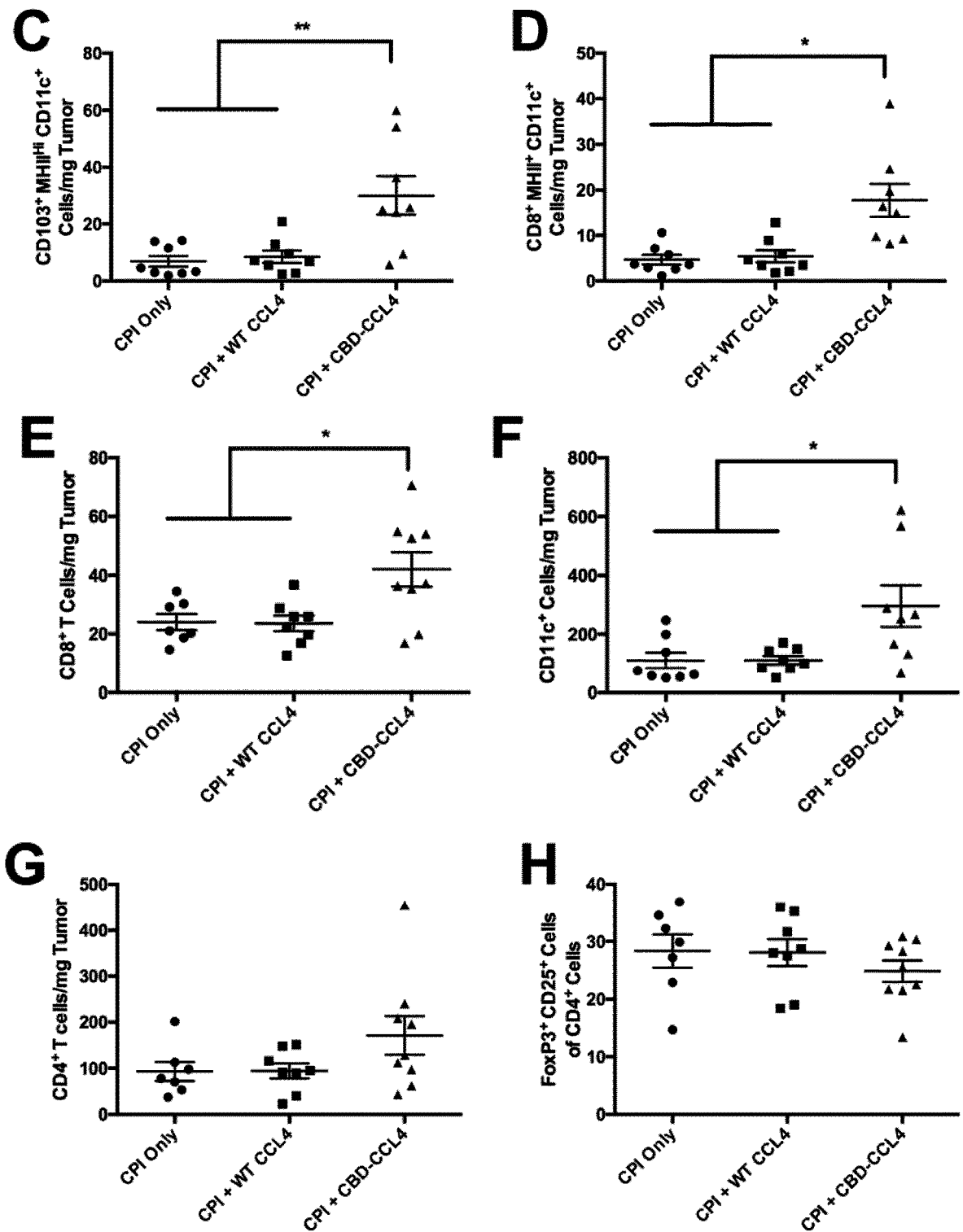
FIG. 10C-H

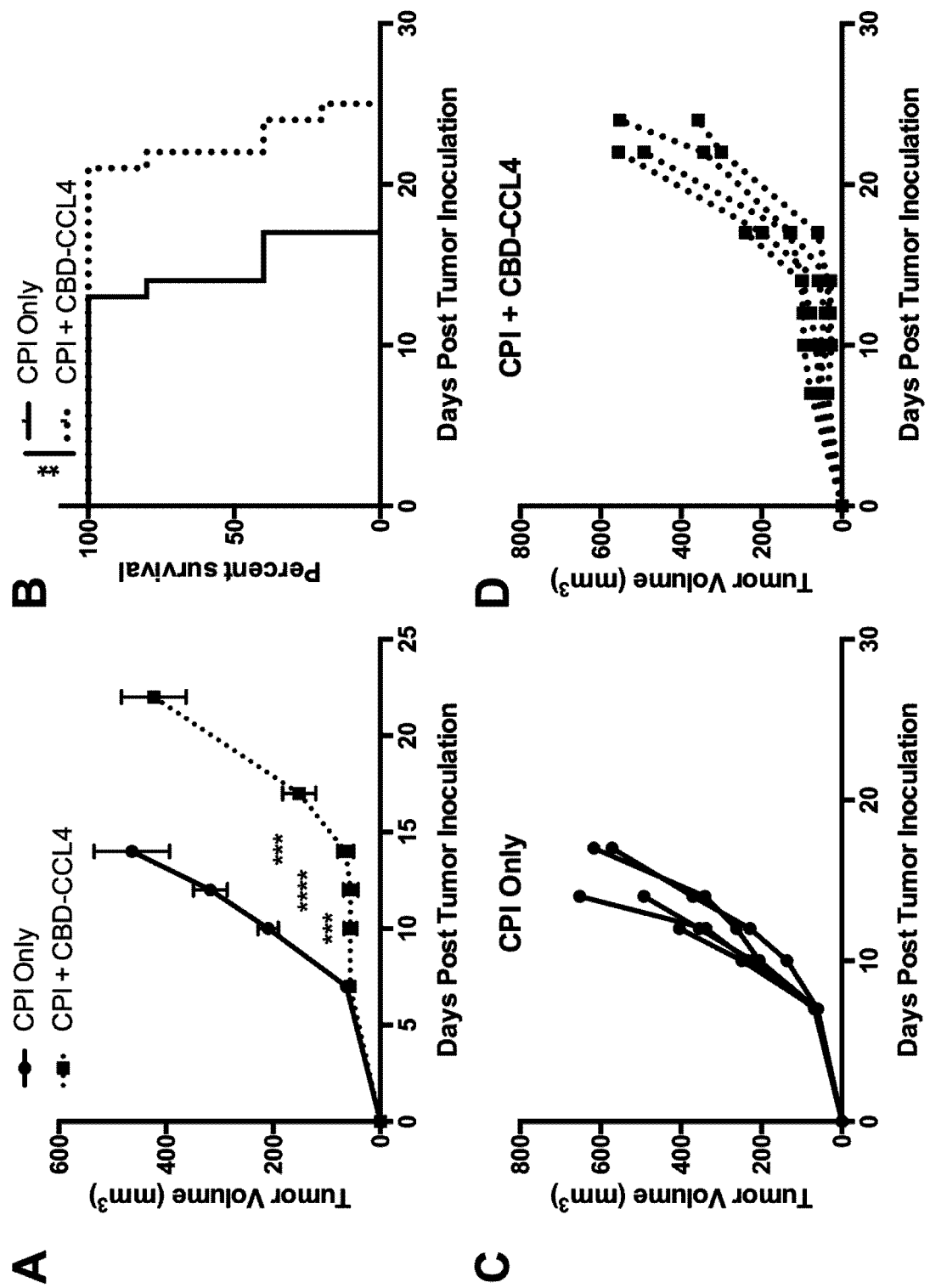
FIG. 11A-D

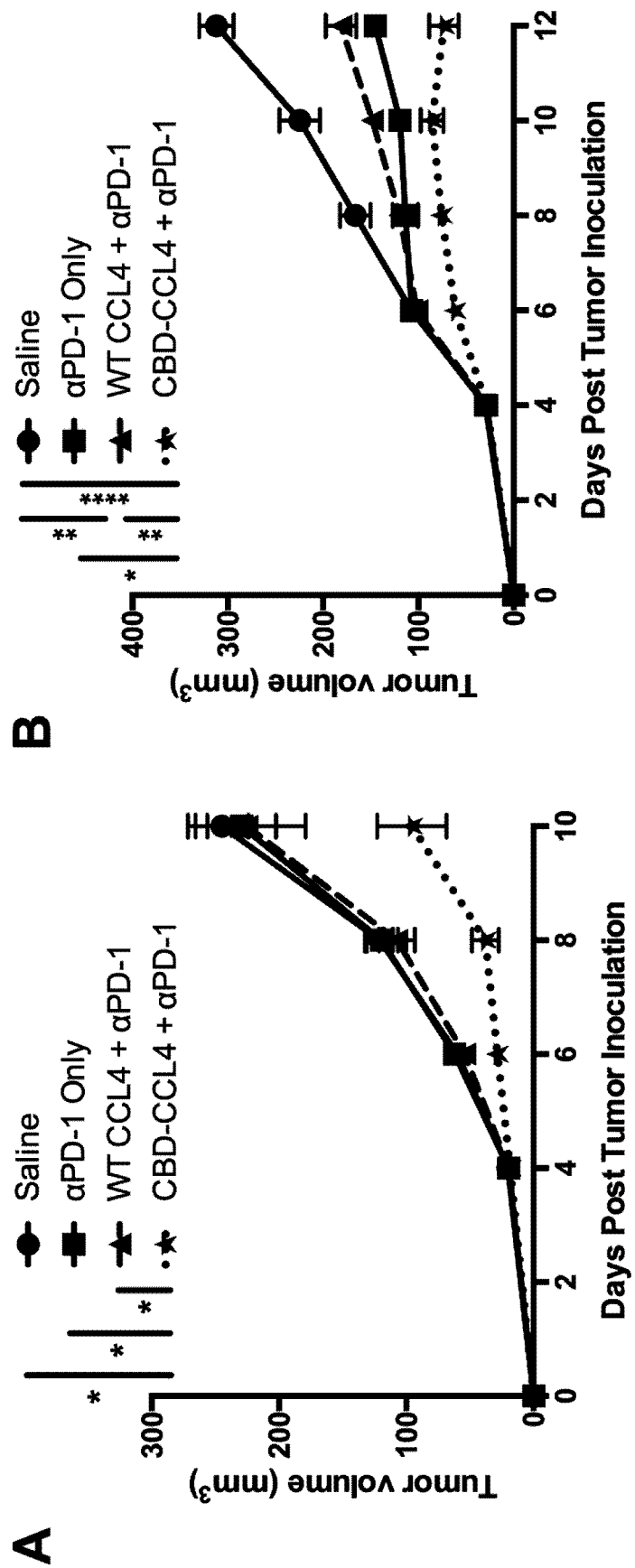
FIG. 12A-B

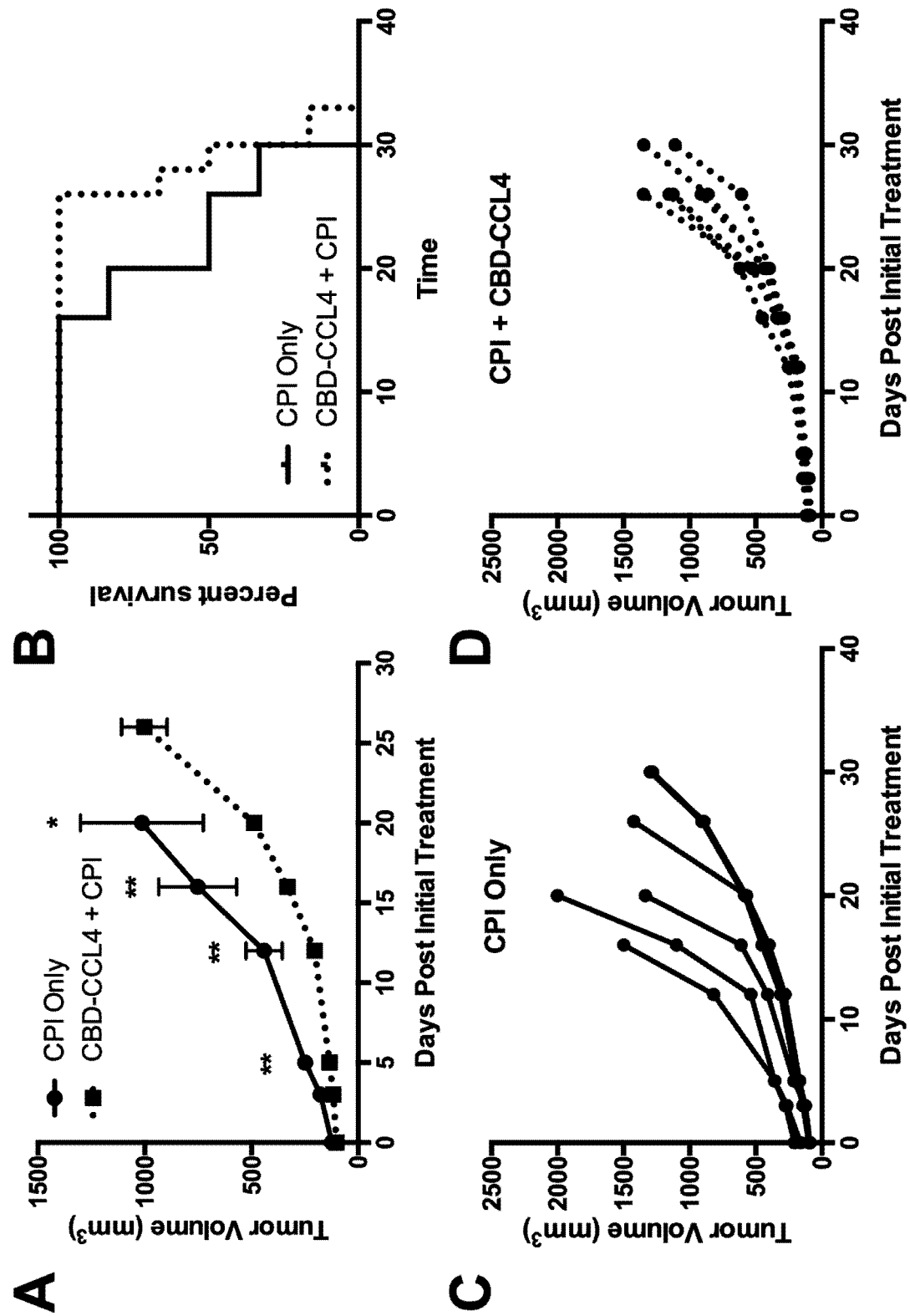
FIG. 13A-D

SEQUENCE LISTING

```
<160> NUMBER OF SEQ ID NOS: 47

<210> SEQ ID NO 1
<211> LENGTH: 22
<212> TYPE: PRT
<213> ORGANISM: Homo sapiens

<400> SEQUENCE: 1

Arg Arg Arg Pro Lys Gly Arg Gly Lys Arg Arg Arg Glu Lys Gln Arg
1               5                   10                  15

Pro Thr Asp Cys His Leu
            20

<210> SEQ ID NO 2
<211> LENGTH: 30
<212> TYPE: PRT
<213> ORGANISM: Homo sapiens

<400> SEQUENCE: 2

Gly Arg Arg Glu Glu Lys Val Gly Lys Lys Glu Lys Ile Gly Lys Lys
1               5                   10                  15

Lys Arg Gln Lys Lys Arg Lys Ala Ala Gln Lys Arg Lys Asn
            20                  25                  30

<210> SEQ ID NO 3
<211> LENGTH: 205
<212> TYPE: PRT
<213> ORGANISM: Homo sapiens

<400> SEQUENCE: 3
```

-continued

Cys Ser Gly Glu Gly Leu Gln Ile Pro Thr Leu Ser Pro Ala Pro Asp
1               5                   10                  15

Cys Ser Gln Pro Leu Asp Val Ile Leu Leu Asp Gly Ser Ser Ser
            20                  25                  30

Phe Pro Ala Ser Tyr Phe Asp Glu Met Lys Ser Phe Ala Lys Ala Phe
            35                  40                  45

Ile Ser Lys Ala Asn Ile Gly Pro Arg Leu Thr Gln Val Ser Val Leu
    50                  55                  60

Gln Tyr Gly Ser Ile Thr Thr Ile Asp Val Pro Trp Asn Val Val Pro
65                  70                  75                  80

Glu Lys Ala His Leu Leu Ser Leu Val Asp Val Met Gln Arg Glu Gly
                85                  90                  95

Gly Pro Ser Gln Ile Gly Asp Ala Leu Gly Phe Ala Val Arg Tyr Leu
            100                 105                 110

Thr Ser Glu Met His Gly Ala Arg Pro Gly Ala Ser Lys Ala Val Val
            115                 120                 125

Ile Leu Val Thr Asp Val Ser Val Asp Ser Val Asp Ala Ala Ala Asp
    130                 135                 140

Ala Ala Arg Ser Asn Arg Val Thr Val Phe Pro Ile Gly Ile Gly Asp
145                 150                 155                 160

Arg Tyr Asp Ala Ala Gln Leu Arg Ile Leu Ala Gly Pro Ala Gly Asp
                165                 170                 175

Ser Asn Val Val Lys Leu Gln Arg Ile Glu Asp Leu Pro Thr Met Val
            180                 185                 190

Thr Leu Gly Asn Ser Phe Leu His Lys Leu Cys Ser Gly
            195                 200                 205

<210> SEQ ID NO 4
<211> LENGTH: 170
<212> TYPE: PRT
<213> ORGANISM: Homo sapiens

<400> SEQUENCE: 4

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
            35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Arg Pro
130                 135                 140

Lys Gly Arg Gly Lys Arg Arg Glu Lys Gln Arg Pro Thr Asp Cys
145                 150                 155                 160

His Leu Cys Gly Asp Ala Val Pro Arg Arg
                165                 170

<210> SEQ ID NO 5
<211> LENGTH: 30
<212> TYPE: PRT
<213> ORGANISM: Homo sapiens

<400> SEQUENCE: 5

Arg Arg Arg Pro Lys Gly Arg Gly Lys Arg Arg Glu Lys Gln Arg
1               5                   10                  15

Pro Thr Asp Cys His Leu Cys Gly Asp Ala Val Pro Arg Arg
            20                  25                  30

<210> SEQ ID NO 6
<211> LENGTH: 18
<212> TYPE: PRT
<213> ORGANISM: Homo sapiens

<400> SEQUENCE: 6

Arg Arg Pro Lys Gly Arg Gly Lys Arg Arg Glu Lys Gln Arg Pro
1               5                   10                  15

Thr Asp

<210> SEQ ID NO 7
<211> LENGTH: 15
<212> TYPE: PRT
<213> ORGANISM: Homo sapiens

<400> SEQUENCE: 7

Arg Arg Arg Pro Lys Gly Arg Gly Lys Arg Arg Glu Lys Gln Gln
1               5                   10                  15

<210> SEQ ID NO 8
<211> LENGTH: 8
<212> TYPE: PRT
<213> ORGANISM: Homo sapiens

<400> SEQUENCE: 8

Gly Lys Arg Arg Arg Glu Lys Gln
1               5

<210> SEQ ID NO 9
<211> LENGTH: 8
<212> TYPE: PRT
<213> ORGANISM: Homo sapiens

<400> SEQUENCE: 9

Arg Arg Arg Pro Lys Gly Arg Gly
1               5

<210> SEQ ID NO 10
<211> LENGTH: 21
<212> TYPE: PRT
<213> ORGANISM: Homo sapiens

<400> SEQUENCE: 10

Arg Arg Lys Thr Lys Gly Lys Arg Lys Arg Ser Arg Asn Ser Gln Thr
1               5                   10                  15

Glu Glu Pro His Pro
            20

<210> SEQ ID NO 11
<211> LENGTH: 222
<212> TYPE: PRT

<213> ORGANISM: Homo sapiens

<400> SEQUENCE: 11

Cys Gln Glu Pro Gly Leu Val Val Pro Thr Asp Ala Pro Val
1               5                   10                  15

Ser Pro Thr Thr Leu Tyr Val Glu Asp Ile Ser Glu Pro Pro Leu His
            20                  25                  30

Asp Phe Tyr Cys Ser Arg Leu Leu Asp Leu Val Phe Leu Leu Asp Gly
        35                  40                  45

Ser Ser Arg Leu Ser Glu Ala Glu Phe Glu Val Leu Lys Ala Phe Val
    50                  55                  60

Val Asp Met Met Glu Arg Leu Arg Ile Ser Gln Lys Trp Val Arg Val
65                  70                  75                  80

Ala Val Val Glu Tyr His Asp Gly Ser His Ala Tyr Ile Gly Leu Lys
                85                  90                  95

Asp Arg Lys Arg Pro Ser Glu Leu Arg Arg Ile Ala Ser Gln Val Lys
            100                 105                 110

Tyr Ala Gly Ser Gln Val Ala Ser Thr Ser Glu Val Leu Lys Tyr Thr
        115                 120                 125

Leu Phe Gln Ile Phe Ser Lys Ile Asp Arg Pro Glu Ala Ser Arg Ile
130                 135                 140

Thr Leu Leu Leu Met Ala Ser Gln Glu Pro Gln Arg Met Ser Arg Asn
145                 150                 155                 160

Phe Val Arg Tyr Val Gln Gly Leu Lys Lys Lys Val Ile Val Ile
                165                 170                 175

Pro Val Gly Ile Gly Pro His Ala Asn Leu Lys Gln Ile Arg Leu Ile
            180                 185                 190

Glu Lys Gln Ala Pro Glu Asn Lys Ala Phe Val Leu Ser Ser Val Asp
        195                 200                 205

Glu Leu Glu Gln Gln Arg Asp Glu Ile Val Ser Tyr Leu Cys
210                 215                 220

<210> SEQ ID NO 12
<211> LENGTH: 98
<212> TYPE: PRT
<213> ORGANISM: Homo sapiens

<400> SEQUENCE: 12

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Gly Arg Arg Glu Glu Lys Val Gly Lys Lys Glu Lys
65                  70                  75                  80

Ile Gly Lys Lys Lys Arg Gln Lys Lys Arg Lys Ala Ala Gln Lys Arg
                85                  90                  95

Lys Asn

<210> SEQ ID NO 13
<211> LENGTH: 2813
<212> TYPE: PRT
<213> ORGANISM: Homo sapiens

<400> SEQUENCE: 13

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
```

-continued

```
                405                 410                 415
Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
                515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
    675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830
```

-continued

```
Gly Lys Glu Tyr Ala Pro Gly Glu Thr Val Lys Ile Gly Cys Asn Thr
    835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Arg Val Thr Ile Leu
                915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
            995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230
```

-continued

Cys Glu Ala Cys Gln Glu Pro Gly Gly Leu Val Val Pro Pro Thr
1235                 1240                 1245

Asp Ala Pro Val Ser Pro Thr Thr Leu Tyr Val Glu Asp Ile Ser
1250                 1255                 1260

Glu Pro Pro Leu His Asp Phe Tyr Cys Ser Arg Leu Leu Asp Leu
1265                 1270                 1275

Val Phe Leu Leu Asp Gly Ser Ser Arg Leu Ser Glu Ala Glu Phe
1280                 1285                 1290

Glu Val Leu Lys Ala Phe Val Val Asp Met Met Glu Arg Leu Arg
1295                 1300                 1305

Ile Ser Gln Lys Trp Val Arg Val Ala Val Val Glu Tyr His Asp
1310                 1315                 1320

Gly Ser His Ala Tyr Ile Gly Leu Lys Asp Arg Lys Arg Pro Ser
1325                 1330                 1335

Glu Leu Arg Arg Ile Ala Ser Gln Val Lys Tyr Ala Gly Ser Gln
1340                 1345                 1350

Val Ala Ser Thr Ser Glu Val Leu Lys Tyr Thr Leu Phe Gln Ile
1355                 1360                 1365

Phe Ser Lys Ile Asp Arg Pro Glu Ala Ser Arg Ile Thr Leu Leu
1370                 1375                 1380

Leu Met Ala Ser Gln Glu Pro Gln Arg Met Ser Arg Asn Phe Val
1385                 1390                 1395

Arg Tyr Val Gln Gly Leu Lys Lys Lys Val Ile Val Ile Pro
1400                 1405                 1410

Val Gly Ile Gly Pro His Ala Asn Leu Lys Gln Ile Arg Leu Ile
1415                 1420                 1425

Glu Lys Gln Ala Pro Glu Asn Lys Ala Phe Val Leu Ser Ser Val
1430                 1435                 1440

Asp Glu Leu Glu Gln Gln Arg Asp Glu Ile Val Ser Tyr Leu Cys
1445                 1450                 1455

Asp Leu Ala Pro Glu Ala Pro Pro Pro Thr Leu Pro Pro Asp Met
1460                 1465                 1470

Ala Gln Val Thr Val Gly Pro Gly Leu Leu Gly Val Ser Thr Leu
1475                 1480                 1485

Gly Pro Lys Arg Asn Ser Met Val Leu Asp Val Ala Phe Val Leu
1490                 1495                 1500

Glu Gly Ser Asp Lys Ile Gly Glu Ala Asp Phe Asn Arg Ser Lys
1505                 1510                 1515

Glu Phe Met Glu Glu Val Ile Gln Arg Met Asp Val Gly Gln Asp
1520                 1525                 1530

Ser Ile His Val Thr Val Leu Gln Tyr Ser Tyr Met Val Thr Val
1535                 1540                 1545

Glu Tyr Pro Phe Ser Glu Ala Gln Ser Lys Gly Asp Ile Leu Gln
1550                 1555                 1560

Arg Val Arg Glu Ile Arg Tyr Gln Gly Gly Asn Arg Thr Asn Thr
1565                 1570                 1575

Gly Leu Ala Leu Arg Tyr Leu Ser Asp His Ser Phe Leu Val Ser
1580                 1585                 1590

Gln Gly Asp Arg Glu Gln Ala Pro Asn Leu Val Tyr Met Val Thr
1595                 1600                 1605

Gly Asn Pro Ala Ser Asp Glu Ile Lys Arg Leu Pro Gly Asp Ile
1610                 1615                 1620

Gln Val Val Pro Ile Gly Val Gly Pro Asn Ala Asn Val Gln Glu

```
            1625                1630                1635

Leu Glu Arg Ile Gly Trp Pro Asn Ala Pro Ile Leu Ile Gln Asp
        1640                1645                1650

Phe Glu Thr Leu Pro Arg Glu Ala Pro Asp Leu Val Leu Gln Arg
        1655                1660                1665

Cys Cys Ser Gly Glu Gly Leu Gln Ile Pro Thr Leu Ser Pro Ala
        1670                1675                1680

Pro Asp Cys Ser Gln Pro Leu Asp Val Ile Leu Leu Leu Asp Gly
        1685                1690                1695

Ser Ser Ser Phe Pro Ala Ser Tyr Phe Asp Glu Met Lys Ser Phe
        1700                1705                1710

Ala Lys Ala Phe Ile Ser Lys Ala Asn Ile Gly Pro Arg Leu Thr
        1715                1720                1725

Gln Val Ser Val Leu Gln Tyr Gly Ser Ile Thr Thr Ile Asp Val
        1730                1735                1740

Pro Trp Asn Val Val Pro Glu Lys Ala His Leu Leu Ser Leu Val
        1745                1750                1755

Asp Val Met Gln Arg Glu Gly Gly Pro Ser Gln Ile Gly Asp Ala
        1760                1765                1770

Leu Gly Phe Ala Val Arg Tyr Leu Thr Ser Glu Met His Gly Ala
        1775                1780                1785

Arg Pro Gly Ala Ser Lys Ala Val Val Ile Leu Val Thr Asp Val
        1790                1795                1800

Ser Val Asp Ser Val Asp Ala Ala Asp Ala Ala Arg Ser Asn
        1805                1810                1815

Arg Val Thr Val Phe Pro Ile Gly Ile Gly Asp Arg Tyr Asp Ala
        1820                1825                1830

Ala Gln Leu Arg Ile Leu Ala Gly Pro Ala Gly Asp Ser Asn Val
        1835                1840                1845

Val Lys Leu Gln Arg Ile Glu Asp Leu Pro Thr Met Val Thr Leu
        1850                1855                1860

Gly Asn Ser Phe Leu His Lys Leu Cys Ser Gly Phe Val Arg Ile
        1865                1870                1875

Cys Met Asp Glu Asp Gly Asn Glu Lys Arg Pro Gly Asp Val Trp
        1880                1885                1890

Thr Leu Pro Asp Gln Cys His Thr Val Thr Cys Gln Pro Asp Gly
        1895                1900                1905

Gln Thr Leu Leu Lys Ser His Arg Val Asn Cys Asp Arg Gly Leu
        1910                1915                1920

Arg Pro Ser Cys Pro Asn Ser Gln Ser Pro Val Lys Val Glu Glu
        1925                1930                1935

Thr Cys Gly Cys Arg Trp Thr Cys Pro Cys Val Cys Thr Gly Ser
        1940                1945                1950

Ser Thr Arg His Ile Val Thr Phe Asp Gly Gln Asn Phe Lys Leu
        1955                1960                1965

Thr Gly Ser Cys Ser Tyr Val Leu Phe Gln Asn Lys Glu Gln Asp
        1970                1975                1980

Leu Glu Val Ile Leu His Asn Gly Ala Cys Ser Pro Gly Ala Arg
        1985                1990                1995

Gln Gly Cys Met Lys Ser Ile Glu Val Lys His Ser Ala Leu Ser
        2000                2005                2010

Val Glu Leu His Ser Asp Met Glu Val Thr Val Asn Gly Arg Leu
        2015                2020                2025
```

-continued

Val Ser Val Pro Tyr Val Gly Gly Asn Met Glu Val Asn Val Tyr
2030              2035              2040

Gly Ala Ile Met His Glu Val Arg Phe Asn His Leu Gly His Ile
2045              2050              2055

Phe Thr Phe Thr Pro Gln Asn Asn Glu Phe Gln Leu Gln Leu Ser
2060              2065              2070

Pro Lys Thr Phe Ala Ser Lys Thr Tyr Gly Leu Cys Gly Ile Cys
2075              2080              2085

Asp Glu Asn Gly Ala Asn Asp Phe Met Leu Arg Asp Gly Thr Val
2090              2095              2100

Thr Thr Asp Trp Lys Thr Leu Val Gln Glu Trp Thr Val Gln Arg
2105              2110              2115

Pro Gly Gln Thr Cys Gln Pro Ile Leu Glu Glu Gln Cys Leu Val
2120              2125              2130

Pro Asp Ser Ser His Cys Gln Val Leu Leu Leu Pro Leu Phe Ala
2135              2140              2145

Glu Cys His Lys Val Leu Ala Pro Ala Thr Phe Tyr Ala Ile Cys
2150              2155              2160

Gln Gln Asp Ser Cys His Gln Glu Gln Val Cys Glu Val Ile Ala
2165              2170              2175

Ser Tyr Ala His Leu Cys Arg Thr Asn Gly Val Cys Val Asp Trp
2180              2185              2190

Arg Thr Pro Asp Phe Cys Ala Met Ser Cys Pro Pro Ser Leu Val
2195              2200              2205

Tyr Asn His Cys Glu His Gly Cys Pro Arg His Cys Asp Gly Asn
2210              2215              2220

Val Ser Ser Cys Gly Asp His Pro Ser Glu Gly Cys Phe Cys Pro
2225              2230              2235

Pro Asp Lys Val Met Leu Glu Gly Ser Cys Val Pro Glu Glu Ala
2240              2245              2250

Cys Thr Gln Cys Ile Gly Glu Asp Gly Val Gln His Gln Phe Leu
2255              2260              2265

Glu Ala Trp Val Pro Asp His Gln Pro Cys Gln Ile Cys Thr Cys
2270              2275              2280

Leu Ser Gly Arg Lys Val Asn Cys Thr Thr Gln Pro Cys Pro Thr
2285              2290              2295

Ala Lys Ala Pro Thr Cys Gly Leu Cys Glu Val Ala Arg Leu Arg
2300              2305              2310

Gln Asn Ala Asp Gln Cys Cys Pro Glu Tyr Glu Cys Val Cys Asp
2315              2320              2325

Pro Val Ser Cys Asp Leu Pro Pro Val Pro His Cys Glu Arg Gly
2330              2335              2340

Leu Gln Pro Thr Leu Thr Asn Pro Gly Glu Cys Arg Pro Asn Phe
2345              2350              2355

Thr Cys Ala Cys Arg Lys Glu Glu Cys Lys Arg Val Ser Pro Pro
2360              2365              2370

Ser Cys Pro Pro His Arg Leu Pro Thr Leu Arg Lys Thr Gln Cys
2375              2380              2385

Cys Asp Glu Tyr Glu Cys Ala Cys Asn Cys Val Asn Ser Thr Val
2390              2395              2400

Ser Cys Pro Leu Gly Tyr Leu Ala Ser Thr Ala Thr Asn Asp Cys
2405              2410              2415

```
Gly Cys Thr Thr Thr Thr Cys Leu Pro Asp Lys Val Cys Val His
2420                2425            2430

Arg Ser Thr Ile Tyr Pro Val Gly Gln Phe Trp Glu Glu Gly Cys
2435                2440            2445

Asp Val Cys Thr Cys Thr Asp Met Glu Asp Ala Val Met Gly Leu
2450                2455            2460

Arg Val Ala Gln Cys Ser Gln Lys Pro Cys Glu Asp Ser Cys Arg
2465                2470            2475

Ser Gly Phe Thr Tyr Val Leu His Glu Gly Glu Cys Cys Gly Arg
2480                2485            2490

Cys Leu Pro Ser Ala Cys Glu Val Val Thr Gly Ser Pro Arg Gly
2495                2500            2505

Asp Ser Gln Ser Ser Trp Lys Ser Val Gly Ser Gln Trp Ala Ser
2510                2515            2520

Pro Glu Asn Pro Cys Leu Ile Asn Glu Cys Val Arg Val Lys Glu
2525                2530            2535

Glu Val Phe Ile Gln Gln Arg Asn Val Ser Cys Pro Gln Leu Glu
2540                2545            2550

Val Pro Val Cys Pro Ser Gly Phe Gln Leu Ser Cys Lys Thr Ser
2555                2560            2565

Ala Cys Cys Pro Ser Cys Arg Cys Glu Arg Met Glu Ala Cys Met
2570                2575            2580

Leu Asn Gly Thr Val Ile Gly Pro Gly Lys Thr Val Met Ile Asp
2585                2590            2595

Val Cys Thr Thr Cys Arg Cys Met Val Gln Val Gly Val Ile Ser
2600                2605            2610

Gly Phe Lys Leu Glu Cys Arg Lys Thr Thr Cys Asn Pro Cys Pro
2615                2620            2625

Leu Gly Tyr Lys Glu Glu Asn Asn Thr Gly Glu Cys Cys Gly Arg
2630                2635            2640

Cys Leu Pro Thr Ala Cys Thr Ile Gln Leu Arg Gly Gly Gln Ile
2645                2650            2655

Met Thr Leu Lys Arg Asp Glu Thr Leu Gln Asp Gly Cys Asp Thr
2660                2665            2670

His Phe Cys Lys Val Asn Glu Arg Gly Glu Tyr Phe Trp Glu Lys
2675                2680            2685

Arg Val Thr Gly Cys Pro Pro Phe Asp Glu His Lys Cys Leu Ala
2690                2695            2700

Glu Gly Gly Lys Ile Met Lys Ile Pro Gly Thr Cys Cys Asp Thr
2705                2710            2715

Cys Glu Glu Pro Glu Cys Asn Asp Ile Thr Ala Arg Leu Gln Tyr
2720                2725            2730

Val Lys Val Gly Ser Cys Lys Ser Glu Val Glu Val Asp Ile His
2735                2740            2745

Tyr Cys Gln Gly Lys Cys Ala Ser Lys Ala Met Tyr Ser Ile Asp
2750                2755            2760

Ile Asn Asp Val Gln Asp Gln Cys Ser Cys Cys Ser Pro Thr Arg
2765                2770            2775

Thr Glu Pro Met Gln Val Ala Leu His Cys Thr Asn Gly Ser Val
2780                2785            2790

Val Tyr His Glu Val Leu Asn Ala Met Glu Cys Lys Cys Ser Pro
2795                2800            2805

Arg Lys Cys Ser Lys
```

-continued

2810

<210> SEQ ID NO 14
<211> LENGTH: 6
<212> TYPE: PRT
<213> ORGANISM: Homo sapiens

<400> SEQUENCE: 14

Thr Lys Lys Leu Arg Thr
1               5

<210> SEQ ID NO 15
<211> LENGTH: 343
<212> TYPE: PRT
<213> ORGANISM: Homo sapiens

<400> SEQUENCE: 15

Gly Pro Phe Gln Gln Arg Gly Leu Phe Asp Phe Met Leu Glu Asp Glu
1               5                   10                  15

Ala Ser Gly Ile Gly Pro Glu Val Pro Asp Asp Arg Asp Phe Glu Pro
            20                  25                  30

Ser Leu Gly Pro Val Cys Pro Phe Arg Cys Gln Cys His Leu Arg Val
        35                  40                  45

Val Gln Cys Ser Asp Leu Gly Leu Asp Lys Val Pro Lys Asp Leu Pro
    50                  55                  60

Pro Asp Thr Thr Leu Leu Asp Leu Gln Asn Asn Lys Ile Thr Glu Ile
65                  70                  75                  80

Lys Asp Gly Asp Phe Lys Asn Leu Lys Asn Leu His Ala Leu Ile Leu
                85                  90                  95

Val Asn Asn Lys Ile Ser Lys Val Ser Pro Gly Ala Phe Thr Pro Leu
            100                 105                 110

Val Lys Leu Glu Arg Leu Tyr Leu Ser Lys Asn Gln Leu Lys Glu Leu
        115                 120                 125

Pro Glu Lys Met Pro Lys Thr Leu Gln Glu Leu Arg Ala His Glu Asn
    130                 135                 140

Glu Ile Thr Lys Val Arg Lys Val Thr Phe Asn Gly Leu Asn Gln Met
145                 150                 155                 160

Ile Val Ile Glu Leu Gly Thr Asn Pro Leu Lys Ser Ser Gly Ile Glu
                165                 170                 175

Asn Gly Ala Phe Gln Gly Met Lys Lys Leu Ser Tyr Ile Arg Ile Ala
            180                 185                 190

Asp Thr Asn Ile Thr Ser Ile Pro Gln Gly Leu Pro Pro Ser Leu Thr
        195                 200                 205

Glu Leu His Leu Asp Gly Asn Lys Ile Ser Arg Val Asp Ala Ala Ser
    210                 215                 220

Leu Lys Gly Leu Asn Asn Leu Ala Lys Leu Gly Leu Ser Phe Asn Ser
225                 230                 235                 240

Ile Ser Ala Val Asp Asn Gly Ser Leu Ala Asn Thr Pro His Leu Arg
                245                 250                 255

Glu Leu His Leu Asp Asn Asn Lys Leu Thr Arg Val Pro Gly Gly Leu
            260                 265                 270

Ala Glu His Lys Tyr Ile Gln Val Val Tyr Leu His Asn Asn Asn Ile
        275                 280                 285

Ser Val Val Gly Ser Ser Asp Phe Cys Pro Pro Gly His Asn Thr Lys
    290                 295                 300

Lys Ala Ser Tyr Ser Gly Val Ser Leu Phe Ser Asn Pro Val Gln Tyr 305              310              315              320
Trp Glu Ile Gln Pro Ser Thr Phe Arg Cys Val Tyr Val Arg Ser Ala
                325                  330                  335

Ile Gln Leu Gly Asn Tyr Lys
        340

<210> SEQ ID NO 16
<211> LENGTH: 115
<212> TYPE: PRT
<213> ORGANISM: Homo sapiens

<400> SEQUENCE: 16

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 17
<211> LENGTH: 115
<212> TYPE: PRT
<213> ORGANISM: Mus musculus

<400> SEQUENCE: 17

Met Asn Trp Ile Asp Val Arg Tyr Asp Leu Glu Lys Ile Glu Ser Leu
1               5                   10                  15

Ile Gln Ser Ile His Ile Asp Thr Thr Leu Tyr Thr Asp Ser Asp Phe
            20                  25                  30

His Pro Ser Cys Lys Val Thr Ala Met Asn Cys Phe Leu Leu Glu Leu
        35                  40                  45

Gln Val Ile Leu His Glu Tyr Ser Asn Met Thr Leu Asn Glu Thr Val
    50                  55                  60

Arg Asn Val Leu Tyr Leu Ala Asn Ser Thr Leu Ser Ser Asn Lys Asn
65                  70                  75                  80

Val Ala Glu Ser Gly Cys Lys Glu Cys Glu Glu Leu Glu Glu Lys Thr
                85                  90                  95

Phe Thr Glu Phe Leu Gln Ser Phe Ile Arg Ile Val Gln Met Phe Ile
            100                 105                 110

Asn Thr Ser
        115

<210> SEQ ID NO 18
<211> LENGTH: 132
<212> TYPE: PRT
<213> ORGANISM: Homo sapiens

<400> SEQUENCE: 18

-continued

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
                20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
        50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130

<210> SEQ ID NO 19
<211> LENGTH: 130
<212> TYPE: PRT
<213> ORGANISM: Mus musculus

<400> SEQUENCE: 19

Met His Lys Ser Ser Pro Gln Gly Pro Asp Arg Leu Leu Ile Arg Leu
1               5                   10                  15

Arg His Leu Ile Asp Ile Val Glu Gln Leu Lys Ile Tyr Glu Asn Asp
                20                  25                  30

Leu Asp Pro Glu Leu Leu Ser Ala Pro Gln Asp Val Lys Gly His Cys
            35                  40                  45

Glu His Ala Ala Phe Ala Cys Phe Gln Lys Ala Lys Leu Lys Pro Ser
        50                  55                  60

Asn Pro Gly Asn Asn Lys Thr Phe Ile Ile Asp Leu Val Ala Gln Leu
65                  70                  75                  80

Arg Arg Arg Leu Pro Ala Arg Arg Gly Gly Lys Lys Gln Lys His Ile
                85                  90                  95

Ala Lys Cys Pro Ser Cys Asp Ser Tyr Glu Lys Arg Thr Pro Lys Glu
            100                 105                 110

Phe Leu Glu Arg Leu Lys Trp Leu Leu Gln Lys Met Ile His Gln His
        115                 120                 125

Leu Ser
    130

<210> SEQ ID NO 20
<211> LENGTH: 197
<212> TYPE: PRT
<213> ORGANISM: Homo sapiens

<400> SEQUENCE: 20

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

```
His Glu Asp Ile Thr Lys Asp Lys Thr Ser Thr Val Glu Ala Cys Leu
         50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
                100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
        130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
                180                 185                 190

Tyr Leu Asn Ala Ser
            195

<210> SEQ ID NO 21
<211> LENGTH: 306
<212> TYPE: PRT
<213> ORGANISM: Homo sapiens

<400> SEQUENCE: 21

Ile Trp Glu Leu Lys Lys Asp Val Tyr Val Val Glu Leu Asp Trp Tyr
 1               5                  10                  15

Pro Asp Ala Pro Gly Glu Met Val Val Leu Thr Cys Asp Thr Pro Glu
                 20                  25                  30

Glu Asp Gly Ile Thr Trp Thr Leu Asp Gln Ser Ser Glu Val Leu Gly
             35                  40                  45

Ser Gly Lys Thr Leu Thr Ile Gln Val Lys Glu Phe Gly Asp Ala Gly
 50                  55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
```

```
            210                 215                 220
Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
            290                 295                 300

Cys Ser
305

<210> SEQ ID NO 22
<211> LENGTH: 193
<212> TYPE: PRT
<213> ORGANISM: Mus musculus

<400> SEQUENCE: 22

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
            35                  40                  45

Thr Arg Asp Gln Thr Ser Thr Leu Lys Thr Cys Leu Pro Leu Glu Leu
50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
            115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala

<210> SEQ ID NO 23
<211> LENGTH: 313
<212> TYPE: PRT
<213> ORGANISM: Mus musculus

<400> SEQUENCE: 23

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30
```

```
Glu Asp Asp Ile Thr Trp Thr Ser Asp Gln Arg His Gly Val Ile Gly
         35                  40                  45

Ser Gly Lys Thr Leu Thr Ile Thr Val Lys Glu Phe Leu Asp Ala Gly
     50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                 85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310

<210> SEQ ID NO 24
<211> LENGTH: 69
<212> TYPE: PRT
<213> ORGANISM: Homo sapiens

<400> SEQUENCE: 24

Ala Pro Met Gly Ser Asp Pro Pro Thr Ala Cys Cys Phe Ser Tyr Thr
1               5                   10                  15

Ala Arg Lys Leu Pro His Asn Phe Val Val Asp Tyr Tyr Glu Thr Ser
            20                  25                  30

Ser Leu Cys Ser Gln Pro Ala Val Val Phe Gln Thr Lys Arg Gly Lys
        35                  40                  45

Gln Val Cys Ala Asp Pro Ser Glu Ser Trp Val Gln Glu Tyr Val Tyr
    50                  55                  60

Asp Leu Glu Leu Asn
65
```

-continued

```
<210> SEQ ID NO 25
<211> LENGTH: 69
<212> TYPE: PRT
<213> ORGANISM: Mus musculus

<400> SEQUENCE: 25

Ala Pro Met Gly Ser Asp Pro Pro Thr Ser Cys Cys Phe Ser Tyr Thr
1               5                   10                  15

Ser Arg Gln Leu His Arg Ser Phe Val Met Asp Tyr Tyr Glu Thr Ser
            20                  25                  30

Ser Leu Cys Ser Lys Pro Ala Val Val Phe Leu Thr Lys Arg Gly Arg
        35                  40                  45

Gln Ile Cys Ala Asn Pro Ser Glu Pro Trp Val Thr Glu Tyr Met Ser
    50                  55                  60

Asp Leu Glu Leu Asn
65

<210> SEQ ID NO 26
<211> LENGTH: 111
<212> TYPE: PRT
<213> ORGANISM: Homo sapiens

<400> SEQUENCE: 26

Ser Asp Gly Gly Ala Gln Asp Cys Cys Leu Lys Tyr Ser Gln Arg Lys
1               5                   10                  15

Ile Pro Ala Lys Val Val Arg Ser Tyr Arg Lys Gln Glu Pro Ser Leu
            20                  25                  30

Gly Cys Ser Ile Pro Ala Ile Leu Phe Leu Pro Arg Lys Arg Ser Gln
        35                  40                  45

Ala Glu Leu Cys Ala Asp Pro Lys Glu Leu Trp Val Gln Gln Leu Met
    50                  55                  60

Gln His Leu Asp Lys Thr Pro Ser Pro Gln Lys Pro Ala Gln Gly Cys
65                  70                  75                  80

Arg Lys Asp Arg Gly Ala Ser Lys Thr Gly Lys Lys Gly Lys Gly Ser
                85                  90                  95

Lys Gly Cys Lys Arg Thr Glu Arg Ser Gln Thr Pro Lys Gly Pro
            100                 105                 110

<210> SEQ ID NO 27
<211> LENGTH: 110
<212> TYPE: PRT
<213> ORGANISM: Mus musculus

<400> SEQUENCE: 27

Ser Asp Gly Gly Gly Gln Asp Cys Cys Leu Lys Tyr Ser Gln Lys Lys
1               5                   10                  15

Ile Pro Tyr Ser Ile Val Arg Gly Tyr Arg Lys Gln Glu Pro Ser Leu
            20                  25                  30

Gly Cys Pro Ile Pro Ala Ile Leu Phe Leu Pro Arg Lys His Ser Lys
        35                  40                  45

Pro Glu Leu Cys Ala Asn Pro Glu Glu Gly Trp Val Gln Asn Leu Met
    50                  55                  60

Arg Arg Leu Asp Gln Pro Pro Ala Pro Gly Lys Gln Ser Pro Gly Cys
65                  70                  75                  80

Arg Lys Asn Arg Gly Thr Ser Lys Ser Gly Lys Lys Gly Lys Gly Ser
                85                  90                  95

Lys Gly Cys Lys Arg Thr Glu Gln Thr Gln Pro Ser Arg Gly
            100                 105                 110
```

-continued

```
<210> SEQ ID NO 28
<211> LENGTH: 103
<212> TYPE: PRT
<213> ORGANISM: Homo sapiens

<400> SEQUENCE: 28

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
                20                  25                  30

Ser Pro Ser Cys Glu Lys Ile Glu Ile Ile Ala Thr Leu Lys Asn Gly
            35                  40                  45

Val Gln Thr Cys Leu Asn Pro Asp Ser Ala Asp Val Lys Glu Leu Ile
50                  55                  60

Lys Lys Trp Glu Lys Gln Val Ser Gln Lys Lys Lys Gln Asn Gly
65                  70                  75                  80

Lys Lys His Gln Lys Lys Val Leu Lys Val Arg Lys Ser Gln Arg
                85                  90                  95

Ser Arg Gln Lys Lys Thr Thr
            100

<210> SEQ ID NO 29
<211> LENGTH: 105
<212> TYPE: PRT
<213> ORGANISM: Mus musculus

<400> SEQUENCE: 29

Thr Leu Val Ile Arg Asn Ala Arg Cys Ser Cys Ile Ser Thr Ser Arg
1               5                   10                  15

Gly Thr Ile His Tyr Lys Ser Leu Lys Asp Leu Lys Gln Phe Ala Pro
                20                  25                  30

Ser Pro Asn Cys Asn Lys Thr Glu Ile Ile Ala Thr Leu Lys Asn Gly
            35                  40                  45

Asp Gln Thr Cys Leu Asp Pro Asp Ser Ala Asn Val Lys Lys Leu Met
50                  55                  60

Lys Glu Trp Glu Lys Lys Ile Asn Gln Lys Lys Lys Gln Lys Arg Gly
65                  70                  75                  80

Lys Lys His Gln Lys Asn Met Lys Asn Arg Lys Pro Lys Thr Pro Gln
                85                  90                  95

Ser Arg Arg Arg Ser Arg Lys Thr Thr
            100                 105

<210> SEQ ID NO 30
<211> LENGTH: 77
<212> TYPE: PRT
<213> ORGANISM: Homo sapiens

<400> SEQUENCE: 30

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
50                  55                  60
```

-continued

Leu Lys Ala Val Ser Lys Glu Arg Ser Lys Arg Ser Pro
65                  70                  75

<210> SEQ ID NO 31
<211> LENGTH: 77
<212> TYPE: PRT
<213> ORGANISM: Mus musculus

<400> SEQUENCE: 31

Ile Pro Leu Ala Arg Thr Val Arg Cys Asn Cys Ile His Ile Asp Asp
1               5                   10                  15

Gly Pro Val Arg Met Arg Ala Ile Gly Lys Leu Glu Ile Ile Pro Ala
                20                  25                  30

Ser Leu Ser Cys Pro Arg Val Glu Ile Ile Ala Thr Met Lys Lys Asn
            35                  40                  45

Asp Glu Gln Arg Cys Leu Asn Pro Glu Ser Lys Thr Ile Lys Asn Leu
        50                  55                  60

Met Lys Ala Phe Ser Gln Lys Arg Ser Lys Arg Ala Pro
65                  70                  75

<210> SEQ ID NO 32
<211> LENGTH: 116
<212> TYPE: PRT
<213> ORGANISM: Homo sapiens

<400> SEQUENCE: 32

Ala His Tyr Asn Thr Glu Ile Leu Lys Ser Ile Asp Asn Glu Trp Arg
1               5                   10                  15

Lys Thr Gln Cys Met Pro Arg Glu Val Cys Ile Asp Val Gly Lys Glu
                20                  25                  30

Phe Gly Val Ala Thr Asn Thr Phe Phe Lys Pro Pro Cys Val Ser Val
            35                  40                  45

Tyr Arg Cys Gly Gly Cys Cys Asn Ser Glu Gly Leu Gln Cys Met Asn
        50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Ala Asn His Thr
                85                  90                  95

Ser Cys Arg Cys Met Ser Lys Leu Asp Val Tyr Arg Gln Val His Ser
            100                 105                 110

Ile Ile Arg Arg
        115

<210> SEQ ID NO 33
<211> LENGTH: 125
<212> TYPE: PRT
<213> ORGANISM: Mus musculus

<400> SEQUENCE: 33

Thr Glu Glu Thr Ile Lys Phe Ala Ala Ala His Tyr Asn Thr Glu Ile
1               5                   10                  15

Leu Lys Ser Ile Asp Asn Glu Trp Arg Lys Thr Gln Cys Met Pro Arg
                20                  25                  30

Glu Val Cys Ile Asp Val Gly Lys Glu Phe Gly Val Ala Thr Asn Thr
            35                  40                  45

Phe Phe Lys Pro Pro Cys Val Ser Val Tyr Arg Cys Gly Gly Cys Cys
        50                  55                  60

Asn Ser Glu Gly Leu Gln Cys Met Asn Thr Ser Thr Ser Tyr Leu Ser

```
                65                  70                  75                  80
Lys Thr Leu Phe Glu Ile Thr Val Pro Leu Ser Gln Gly Pro Lys Pro
                    85                  90                  95

Val Thr Ile Ser Phe Ala Asn His Thr Ser Cys Arg Cys Met Ser Lys
                    100                 105                 110

Leu Asp Val Tyr Arg Gln Val His Ser Ile Ile Arg Arg
                    115                 120                 125

<210> SEQ ID NO 34
<211> LENGTH: 196
<212> TYPE: PRT
<213> ORGANISM: Homo sapiens

<400> SEQUENCE: 34

Cys Ser Gln Pro Leu Asp Val Ile Leu Leu Asp Gly Ser Ser Ser
1               5                   10                  15

Phe Pro Ala Ser Tyr Phe Asp Glu Met Lys Ser Phe Ala Lys Ala Phe
                20                  25                  30

Ile Ser Lys Ala Asn Ile Gly Pro Arg Leu Thr Gln Val Ser Val Leu
                35                  40                  45

Gln Tyr Gly Ser Ile Thr Thr Ile Asp Val Pro Trp Asn Val Val Pro
50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
                100                 105                 110

Ile Leu Val Thr Asp Val Ser Val Asp Ser Val Asp Ala Ala Ala Asp
                115                 120                 125

Ala Ala Arg Ser Asn Arg Val Thr Val Phe Pro Ile Gly Ile Gly Asp
                130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
                180                 185                 190

Ile Cys Thr Gly
            195

<210> SEQ ID NO 35
<211> LENGTH: 148
<212> TYPE: PRT
<213> ORGANISM: Mus musculus

<400> SEQUENCE: 35

Pro Thr Ser Ser Ser Thr Ser Ser Thr Ala Glu Ala Gln Gln Gln
1               5                   10                  15

Gln Gln Gln Gln Gln Gln Gln Gln His Leu Glu Gln Leu Leu Met
                20                  25                  30

Asp Leu Gln Glu Leu Leu Ser Arg Met Glu Asn Tyr Arg Asn Leu Lys
                35                  40                  45

Leu Pro Arg Met Leu Thr Phe Lys Phe Tyr Leu Pro Lys Gln Ala Thr
50                  55                  60

Glu Leu Lys Asp Leu Gln Cys Leu Glu Asp Glu Leu Gly Pro Leu Arg
```

```
                65                  70                  75                  80
His Val Leu Asp Leu Thr Gln Ser Lys Ser Phe Gln Leu Glu Asp Ala
                    85                  90                  95

Glu Asn Phe Ile Ser Asn Ile Arg Val Thr Val Lys Leu Lys Gly
                100                 105                 110

Ser Asp Asn Thr Phe Glu Cys Gln Phe Asp Glu Ser Ala Thr Val
                115                 120                 125

Val Asp Phe Leu Arg Arg Trp Ile Ala Phe Cys Gln Ser Ile Ile Ser
                130                 135                 140

Thr Ser Pro Gln
145

<210> SEQ ID NO 36
<211> LENGTH: 349
<212> TYPE: PRT
<213> ORGANISM: Artificial Sequence
<220> FEATURE:
<223> OTHER INFORMATION: Synthetic peptide

<400> SEQUENCE: 36

Cys Ser Gln Pro Leu Asp Val Ile Leu Leu Asp Gly Ser Ser Ser
1               5                   10                  15

Phe Pro Ala Ser Tyr Phe Asp Glu Met Lys Ser Phe Ala Lys Ala Phe
                20                  25                  30

Ile Ser Lys Ala Asn Ile Gly Pro Arg Leu Thr Gln Val Ser Val Leu
                35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
                100                 105                 110

Ile Leu Val Thr Asp Val Ser Val Asp Ser Val Asp Ala Ala Ala Asp
                115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
                180                 185                 190

Ile Gly Gly Gly Ser Gly Gly Gly Ser Pro Thr Ser Ser Ser Thr Ser
                195                 200                 205

Ser Ser Thr Ala Glu Ala Gln Gln Gln Gln Gln Gln Gln Gln Gln Gln
    210                 215                 220

Gln Gln His Leu Glu Gln Leu Leu Met Asp Leu Gln Glu Leu Leu Ser
225                 230                 235                 240

Arg Met Glu Asn Tyr Arg Asn Leu Lys Leu Pro Arg Met Leu Thr Phe
                245                 250                 255

Lys Phe Tyr Leu Pro Lys Gln Ala Thr Glu Leu Lys Asp Leu Gln Cys
                260                 265                 270

Leu Glu Asp Glu Leu Gly Pro Leu Arg His Val Leu Asp Leu Thr Gln
```

```
                     275                 280                 285
Ser Lys Ser Phe Gln Leu Glu Asp Ala Glu Asn Phe Ile Ser Asn Ile
290                 295                 300

Arg Val Thr Val Val Lys Leu Lys Gly Ser Asp Asn Thr Phe Glu Cys
305                 310                 315                 320

Gln Phe Asp Asp Glu Ser Ala Thr Val Val Asp Phe Leu Arg Arg Trp
                325                 330                 335

Ile Ala Phe Cys Gln Ser Ile Ile Ser Thr Ser Pro Gln
                340                 345

<210> SEQ ID NO 37
<211> LENGTH: 153
<212> TYPE: PRT
<213> ORGANISM: Homo sapiens

<400> SEQUENCE: 37

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 38
<211> LENGTH: 346
<212> TYPE: PRT
<213> ORGANISM: Artificial Sequence
<220> FEATURE:
<223> OTHER INFORMATION: synthetic peptide

<400> SEQUENCE: 38

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
                20                  25                  30

Ile Ser Lys Ala Asn Ile Gly Pro Arg Leu Thr Gln Val Ser Val Leu
            35                  40                  45

Gln Tyr Gly Ser Ile Thr Thr Ile Asp Val Pro Trp Asn Val Val Pro
50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95
```

```
Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
            115                 120                 125

Ala Ala Arg Ser Asn Arg Val Thr Val Phe Pro Ile Gly Ile Gly Asp
130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Met Tyr Arg Met Gln Leu Leu Ser Cys Ile Ala Leu Ser Leu Ala
            195                 200                 205

Leu Val Thr Asn Ser Ala Pro Thr Ser Ser Thr Lys Lys Thr Gln
210                 215                 220

Leu Gln Leu Glu His Leu Leu Leu Asp Leu Gln Met Ile Leu Asn Gly
225                 230                 235                 240

Ile Asn Asn Tyr Lys Asn Pro Lys Leu Thr Arg Met Leu Thr Phe Lys
                245                 250                 255

Phe Tyr Met Pro Lys Lys Ala Thr Glu Leu Lys His Leu Gln Cys Leu
            260                 265                 270

Glu Glu Glu Leu Lys Pro Leu Glu Glu Val Leu Asn Leu Ala Gln Ser
            275                 280                 285

Lys Asn Phe His Leu Arg Pro Arg Asp Leu Ile Ser Asn Ile Asn Val
            290                 295                 300

Ile Val Leu Glu Leu Lys Gly Ser Glu Thr Thr Phe Met Cys Glu Tyr
305                 310                 315                 320

Ala Asp Glu Thr Ala Thr Ile Val Glu Phe Leu Asn Arg Trp Ile Thr
                325                 330                 335

Phe Cys Gln Ser Ile Ile Ser Thr Leu Thr
            340                 345

<210> SEQ ID NO 39
<211> LENGTH: 182
<212> TYPE: PRT
<213> ORGANISM: Mus musculus

<400> SEQUENCE: 39

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
```

115                 120                 125
Trp Glu Met Ser Ser Thr Ala Leu His Leu Lys Ser Tyr Tyr Trp Arg
            130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn
            180

<210> SEQ ID NO 40
<211> LENGTH: 166
<212> TYPE: PRT
<213> ORGANISM: Homo sapiens

<400> SEQUENCE: 40

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 41
<211> LENGTH: 167
<212> TYPE: PRT
<213> ORGANISM: Mus musculus

<400> SEQUENCE: 41

Cys Asp Leu Pro His Thr Tyr Asn Leu Arg Asn Lys Arg Ala Leu Lys
1               5                   10                  15

Val Leu Ala Gln Met Arg Arg Leu Pro Phe Leu Ser Cys Leu Lys Asp
            20                  25                  30

Arg Gln Asp Phe Gly Phe Pro Leu Glu Lys Val Asp Asn Gln Gln Ile
        35                  40                  45

Gln Lys Ala Gln Ala Ile Pro Val Leu Arg Asp Leu Thr Gln Gln Thr
        50                  55                  60

Leu Asn Leu Phe Thr Ser Lys Ala Ser Ser Ala Ala Trp Asn Thr Thr
65                  70                  75                  80

Leu Leu Asp Ser Phe Cys Asn Asp Leu His Gln Gln Leu Asn Asp Leu

```
                    85                  90                  95

Gln Thr Cys Leu Met Gln Gln Val Gly Val Gln Glu Pro Pro Leu Thr
            100                 105                 110

Gln Glu Asp Ala Leu Leu Ala Val Arg Lys Tyr Phe His Arg Ile Thr
        115                 120                 125

Val Tyr Leu Arg Glu Lys Lys His Ser Pro Cys Ala Trp Glu Val Val
    130                 135                 140

Arg Ala Glu Val Trp Arg Ala Leu Ser Ser Val Asn Leu Leu Pro
145                 150                 155                 160

Arg Leu Ser Glu Glu Lys Glu
                165

<210> SEQ ID NO 42
<211> LENGTH: 72
<212> TYPE: PRT
<213> ORGANISM: Homo sapiens

<400> SEQUENCE: 42

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys
65                  70

<210> SEQ ID NO 43
<211> LENGTH: 93
<212> TYPE: PRT
<213> ORGANISM: Mus musculus

<400> SEQUENCE: 43

Val Gly Thr Glu Val Leu Glu Glu Ser Ser Cys Val Asn Leu Gln Thr
1               5                   10                  15

Gln Arg Leu Pro Val Gln Lys Ile Lys Thr Tyr Ile Ile Trp Glu Gly
            20                  25                  30

Ala Met Arg Ala Val Ile Phe Val Thr Lys Arg Gly Leu Lys Ile Cys
        35                  40                  45

Ala Asp Pro Glu Ala Lys Trp Val Lys Ala Ala Ile Lys Thr Val Asp
    50                  55                  60

Gly Arg Ala Ser Thr Arg Lys Asn Met Ala Glu Thr Val Pro Thr Gly
65                  70                  75                  80

Ala Gln Arg Ser Thr Ser Thr Ala Ile Thr Leu Thr Gly
            85                  90

<210> SEQ ID NO 44
<211> LENGTH: 92
<212> TYPE: PRT
<213> ORGANISM: Homo sapiens

<400> SEQUENCE: 44

Gly Ser Glu Val Ser Asp Lys Arg Thr Cys Val Ser Leu Thr Thr Gln
1               5                   10                  15

Arg Leu Pro Val Ser Arg Ile Lys Thr Tyr Thr Ile Thr Glu Gly Ser
            20                  25                  30
```

```
Leu Arg Ala Val Ile Phe Ile Thr Lys Arg Gly Leu Lys Val Cys Ala
            35                  40                  45

Asp Pro Gln Ala Thr Trp Val Arg Asp Val Val Ser Met Asp Arg
    50                  55                  60

Lys Ser Asn Thr Arg Asn Asn Met Ile Gln Thr Lys Pro Thr Gly Thr
65                  70                  75                  80

Gln Gln Ser Thr Asn Thr Ala Val Thr Leu Thr Gly
            85                  90

<210> SEQ ID NO 45
<211> LENGTH: 234
<212> TYPE: PRT
<213> ORGANISM: Mus musculus

<400> SEQUENCE: 45

Gly Thr Thr Cys Pro Pro Val Ser Ile Glu His Ala Asp Ile Arg
1               5                   10                  15

Val Lys Asn Tyr Ser Val Asn Ser Arg Glu Arg Tyr Val Cys Asn Ser
            20                  25                  30

Gly Phe Lys Arg Lys Ala Gly Thr Ser Thr Leu Ile Glu Cys Val Ile
            35                  40                  45

Asn Lys Asn Thr Asn Val Ala His Trp Thr Thr Pro Ser Leu Lys Cys
50                  55                  60

Ile Arg Asp Pro Ser Leu Ala His Tyr Ser Pro Val Pro Thr Val Val
65                  70                  75                  80

Thr Pro Lys Val Thr Ser Gln Pro Glu Ser Pro Ser Pro Ser Ala Lys
            85                  90                  95

Glu Pro Glu Ala Ser Gly Gly Ser Gly Gly Gly Ser Gly Gly Gly
            100                 105                 110

Ser Gly Gly Gly Gly Ser Leu Gln Asn Trp Ile Asp Val Arg Tyr Asp
            115                 120                 125

Leu Glu Lys Ile Glu Ser Leu Ile Gln Ser Ile His Ile Asp Thr Thr
            130                 135                 140

Leu Tyr Thr Asp Ser Asp Phe His Pro Ser Cys Lys Val Thr Ala Met
145                 150                 155                 160

Asn Cys Phe Leu Leu Glu Leu Gln Val Ile Leu His Glu Tyr Ser Asn
                165                 170                 175

Met Thr Leu Asn Glu Thr Val Arg Asn Val Leu Tyr Leu Ala Asn Ser
            180                 185                 190

Thr Leu Ser Ser Asn Lys Asn Val Ala Glu Ser Gly Cys Lys Glu Cys
            195                 200                 205

Glu Glu Leu Glu Glu Lys Thr Phe Thr Glu Phe Leu Gln Ser Phe Ile
            210                 215                 220

Arg Ile Val Gln Met Phe Ile Asn Thr Ser
225                 230

<210> SEQ ID NO 46
<211> LENGTH: 424
<212> TYPE: PRT
<213> ORGANISM: Homo sapiens

<400> SEQUENCE: 46

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30
```

```
Phe Lys Arg Lys Ala Gly Thr Ser Ser Leu Thr Glu Cys Val Leu Asn
    35                  40                  45

Lys Ala Thr Asn Val Ala His Trp Thr Thr Pro Ser Leu Lys Cys Ile
50                  55                  60

Arg Asp Val Asp Asp Lys Thr His Thr Cys Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
            115                 120                 125

Gly Val Glu Val His Asn Ala Lys Thr Lys Pro Arg Glu Glu Gln Tyr
        130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
            195                 200                 205

Asn Gln Val Ser Leu Thr Cys Leu Val Lys Gly Phe Tyr Pro Ser Asp
        210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
            275                 280                 285

Leu Ser Leu Ser Pro Gly Lys Gly Gly Gly Ser Gly Gly Gly Gly
        290                 295                 300

Ser Gly Gly Gly Ser Asn Trp Val Asn Val Ile Ser Asp Leu Lys
305                 310                 315                 320

Lys Ile Glu Asp Leu Ile Gln Ser Met His Ile Asp Ala Thr Leu Tyr
            325                 330                 335

Thr Glu Ser Asp Val His Pro Ser Cys Lys Val Thr Ala Met Lys Cys
            340                 345                 350

Phe Leu Leu Glu Leu Gln Val Ile Ser Leu Glu Ser Gly Asp Ala Ser
        355                 360                 365

Ile His Asp Thr Val Glu Asn Leu Ile Ile Leu Ala Asn Asp Ser Leu
370                 375                 380

Ser Ser Asn Gly Asn Val Thr Glu Ser Gly Cys Lys Glu Cys Glu Glu
385                 390                 395                 400

Leu Glu Glu Lys Asn Ile Lys Glu Phe Leu Gln Ser Phe Val His Ile
                405                 410                 415

Val Gln Met Phe Ile Asn Thr Ser
            420

<210> SEQ ID NO 47
<211> LENGTH: 278
```

```
<212> TYPE: PRT
<213> ORGANISM: Artificial Sequence
<220> FEATURE:
<223> OTHER INFORMATION: Synthetic polypeptide

<400> SEQUENCE: 47

Cys Ser Gln Pro Leu Asp Val Ile Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
            35                  40                  45

Gln Tyr Gly Ser Ile Thr Thr Ile Asp Val Pro Trp Asn Val Val Pro
50                  55                          60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
            115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile Gly Gly Gly Gly Ser Gly Gly Gly Gly Ser Ala Pro Met Gly Ser
            195                 200                 205

Asp Pro Pro Thr Ser Cys Cys Phe Ser Tyr Thr Ser Arg Gln Leu His
    210                 215                 220

Arg Ser Phe Val Met Asp Tyr Tyr Glu Thr Ser Ser Leu Cys Ser Lys
225                 230                 235                 240

Pro Ala Val Val Phe Leu Thr Lys Arg Gly Arg Gln Ile Cys Ala Asn
                245                 250                 255

Pro Ser Glu Pro Trp Val Thr Glu Tyr Met Ser Asp Leu Glu Leu Asn
            260                 265                 270

His His His His His His
            275
```

METHODS AND COMPOSITIONS FOR TREATING CANCER WITH ECM-AFFINITY PEPTIDES LINKED TO CYTOKINES

CROSS-REFERENCE TO RELATED APPLICATIONS

This application is a national phase application under 35 U.S.C. § 371 of International Application No. PCT/US2019/020685 filed Mar. 5, 2019, which claims the benefit of priority to U.S. Provisional Patent Application Nos. 62/638,520 filed Mar. 5, 2018 and 62/727,156 filed Sep. 5, 2018, all of which are incorporated herein by reference in their entireties.

BACKGROUND

I. Field of the Invention

The invention generally relates to the field of medicine. More particularly, it concerns compositions and methods involving nucleotide constructs and proteins—including engineered cytokines for targeting areas associated with vascular permeability, such as tumors.

II. Background

The immune system plays a critical role in the pathogenesis of a wide variety of cancers. When cancers progress, it is widely believed that the immune system either fails to respond sufficiently or fails to respond appropriately, allowing cancer cells to grow. Currently, standard medical treatments for cancer including chemotherapy, surgery, radiation therapy and cellular therapy have clear limitations with regard to both efficacy and toxicity. To date, these approaches have met with varying degrees of success dependent upon the type of cancer, general health of the patient, stage of disease at the time of diagnosis, etc. Improved strategies that combine specific manipulation of the immune response to cancer in combination with standard medical treatments may provide a means for enhanced efficacy and decreased toxicity of cancer therapies.

Numerous cytokines have been shown to play a role in regulation of the immune response to tumors. However, direct administration of cytokines for cancer therapy may not be practical, as they are often toxic when administered systemically. (See, for example, Asher et al., *J. Immunol.* 146: 3227-3234, 1991; Havell et al., *J. Exp. Med.* 167: 1067-1085, 1988.) There remains a need for additional compositions and methods to provide more effective and less toxic cytokine therapies for cancer.

SUMMARY OF INVENTION

The methods and compositions described herein provide needed compositions and methods for targeting or localizing a therapy in areas having vascular leak or permeability by providing a cytokine that is specifically targeted to and/or retained by collagen limiting systemic exposure and reducing side-effects associated with the cytokine. Certain embodiments are directed to the administration of a cancer therapy that localizes in a tumor due to vascular permeability of the tumor. Accordingly, aspects of the disclosure relate to a composition comprising a cytokine operatively linked to an extracellular matrix (ECM)-affinity peptide, e.g., a collagen binding domain (CBD). An ECM-affinity peptide is one that has affinity for and binds to an extracellular matrix protein, such as collagen.

In one embodiment, the ECM-affinity peptide comprises a peptide from von Willebrand Factor (vWF) or decorin. In one embodiment, the ECM-affinity peptide comprises, consist essentially of, or consist of at least, at most, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 210, 220, 230, 240, 250, 300, 400, 500, 600, 700, 800, 900, 1000, 1500, 2000, to 2800, including all values and ranges there between, contiguous amino acids of vWF A3 domain (SEQ ID NO:3); vWF A1 domain (SEQ ID NO:11); vWF (SEQ ID NO:13); decorin (SEQ ID NO:15), or vWF A3 domain (SEQ ID NO:34). In certain aspects an ECM-affinity peptide can comprise amino acids 1 to 193 of vWF A3 domain (SEQ ID NO:34).

ECM-affinity peptides can include a peptide or protein fragment having at least, or about 70, 75, 80, 85, 90, 91, 92, 93, 94, 95, 96, 97, 98, 99, 100% identity to vWF A3 domain (SEQ ID NO:3); vWF A1 domain (SEQ ID NO:11); vWF (SEQ ID NO:13); decorin (SEQ ID NO:15), or vWF A3 domain (SEQ ID NO:34), fragments including: (A) a fragment of SEQ ID NO:3 includes a fragment of segment starting at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 and ending at amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, or 205; (B) a fragment of SEQ ID NO:11 includes a fragment of segment starting at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, or 212 and ending at amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, or 222; (C) a fragment of SEQ ID NO:13 a fragment of segment starting at amino acid 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, or 2800, including all values and ranges there between, and ending at amino acid 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, 2800 281 or 2813, including all values and ranges there between; (D) a fragment of SEQ ID NO:15 starting at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, or 333 and ending at amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, or 343; (E) a fragment of SEQ ID NO:34 starting at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, or 186 and ending at amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, or 196.

In certain aspect any polypetide, peptide, or fragment thereof need not contain all amino acids of the referenced sequence identifier and may have 1, 2, 3, 4, 5, 6, 7, 8, 9, 10, 11, 12, 13, 14, 15, 16, 17, 18, 19, 20, 30, 40, 50 or so amino acids removed or deleted while maintaining at least one activity of the polypeptide or peptide, e.g., ECM or collagen binding. In further aspects any polypetide or peptide may contain additional amino acids at the terminus or inserted internally in the amino acid sequence of the referenced sequence identifier and may have 1, 2, 3, 4, 5, 6, 7, 8, 9, 10, 11, 12, 13, 14, 15, 16, 17, 18, 19, 20, 30, 40, 50 or so amino acids fused to the amino terminus, carboxy terminus, inserted in the amino acid sequence or a combination thereof while maintaining at least one activity of the polypeptide or peptide e.g., ECM or collagen binding. It is specifically contemplated that any of the ECM-affinity peptides disclosed herein may be excluded from some embodiments (e.g., P1GF-2 and CXCL-12γ peptides). In one embodiment, the ECM-affinity peptide comprises a peptide that has at least or at most 70, 72, 74, 76, 78, 80, 82, 84, 86, 88, 90, 92, 94, 96, 98, 99, or 100% identity (or any range derivable therein) to one of SEQ ID NO:3; SEQ ID NO:11; SEQ ID NO:13; SEQ ID NO:15, or SEQ ID NO:34 or to a peptide segment or fragment from SEQ ID NO:3; SEQ ID NO:11; SEQ ID NO:13; SEQ ID NO:15, or SEQ ID NO:34. A peptide segment or fragment can include 10, 20, 30, 40, 50, 60, 70, 80, 90, 100, 110, 120, 130, 140, 150, 160, 170, 180, 190, 200, 210, 220, or more consecutive amino acids of SEQ ID NO:3; SEQ ID NO:11; SEQ ID NO:13; SEQ ID NO:15, or SEQ ID NO:34. In some embodiments, the peptide is at least 85% identical to SEQ ID NO:3; SEQ ID NO:11; SEQ ID NO:13; SEQ ID NO:15, or SEQ ID NO:34. In some embodiments, the peptide comprises or consists of or consist essentially of SEQ ID NO:3; SEQ ID NO:11; SEQ ID NO:13; SEQ ID NO:15, or SEQ ID NO:34 or a fragment thereof. In one embodiment, the ECM-affinity peptide comprises a von Willebrand factor (vWF) peptide. In some embodiments, the VWF peptide is a vWF A1 or A3 peptide. In some embodiments, the VWF peptide comprises a peptide that is at least 85% identical to all or part of SEQ ID NO:3, SEQ ID NO:11, or SEQ ID NO:34. In some embodiments, the VWF peptide comprises SEQ ID NO:3 or SEQ ID NO:11 or SEQ ID NO:34 or is a fragment thereof.

In some embodiments, the ECM-affinity peptide comprises a decorin peptide. In some embodiments, the peptide is at least 85% identical to all or part of SEQ ID NO:15. comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 15, 175, 200, 225, 250, 275, 300, 325, to 343 contiguous amino acids (including all values and ranges there between) of SEQ ID NO:15. In one embodiment, the ECM-affinity peptide comprises a peptide that has at least or at most 70, 72, 74, 76, 78, 80, 82, 84, 86, 88, 90, 92, 94, 96, 98, 99, or 100% identity (or any range derivable therein) to SEQ ID NO:15 or to a peptide segment of SEQ ID NO:15. In some embodiments, the peptide is at least 85% identical to SEQ ID NO:15. In some embodiments, the peptide comprises or consists of or consist essentially of SEQ ID NO:15 or a fragment thereof.

In some embodiments, the peptide is covalently linked to the cytokine. In certain aspects the peptide is an amino terminal or carboxy terminal fusion with a cytokine polypeptide. In some embodiments, the peptide is crosslinked to the cytokine through a bifunctional crosslinker.

In other embodiments the cytokine peptide can be selected from hIL-2 (SEQ ID NO:37); mIL-2 (SEQ ID NO:37); hIL-15 (SEQ ID NO:16), mIL-15 (SEQ ID NO:17), hIL-21 (SEQ ID NO:18), mIL-21 (SEQ ID NO:19), hIL-12 p35 (SEQ ID NO:20), hIL-12 p40 (SEQ ID NO:21), mIL-12 p35 (SEQ ID NO:22), mIL-12 p35 (SEQ ID NO:23), hCCL4 (SEQ ID NO:24), mCCL4 (SEQ ID NO:25), hCCL21 (SEQ ID NO:26), mCCL21 (SEQ ID NO:27), hCXCL9 (SEQ ID NO:28), mCXCL9 (SEQ ID NO:29), hCXCL10 (SEQ ID NO:30), mCXCL10 (SEQ ID NO:31), hVEGF-C(SEQ ID NO:32), mVEGF-C(SEQ ID NO:33), mIFNβ (SEQ ID NO:39), hIFNβ (SEQ ID NO:40), mIFNα2 (SEQ ID NO:41), hIFNα2 (SEQ ID NO:42), mXCL1 (SEQ ID NO:43), hXCL1 (SEQ ID NO:44), mIL-15 super agonist (SEQ ID NO:45), or hIL-15 super agonist (SEQ ID NO:46). The cytokine portion of the ECM-affinity peptide cytokine conjugate can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150 contiguous amino acids of hIL-15 (SEQ ID NO:16), mIL-15 (SEQ ID NO:17), hIL-21 (SEQ ID NO:18), mIL-21 (SEQ ID NO:19), hIL-12 p35 (SEQ ID NO:20), hIL-12 p40 (SEQ ID NO:21), mIL-12 p35 (SEQ ID NO:22), mIL-12 p35 (SEQ ID NO:23), hCCL4 (SEQ ID NO:24), mCCL4 (SEQ ID NO:25), hCCL21 (SEQ ID NO:26), mCCL21 (SEQ ID NO:27), hCXCL9 (SEQ ID NO:28), mCXCL9 (SEQ ID NO:29), hCXCL10 (SEQ ID NO:30), mCXCL10 (SEQ ID NO:31), hVEGF-C(SEQ ID NO:32), mVEGF-C(SEQ ID NO:33), mIFNβ (SEQ ID NO:39), hIFNβ (SEQ ID NO:40), mIFNα2 (SEQ ID NO:41), hIFNα2 (SEQ ID NO:42), mXCL1 (SEQ ID NO:43), hXCL1 (SEQ ID NO:44), mIL-15 super agonist (SEQ ID NO:45), or hIL-15 super agonist (SEQ ID NO:46). In one embodiment, the cytokinie peptide comprises a peptide that has at least or at most 70, 72, 74, 76, 78, 80, 82, 84, 86, 88, 90, 92, 94, 96, 98, 99, or 100% identity (or any range derivable therein) to hIL-15 (SEQ ID NO:16), mIL-15 (SEQ ID NO:17), hIL-21 (SEQ ID NO:18), mIL-21 (SEQ ID NO:19), hIL-12 p35 (SEQ ID NO:20), hIL-12 p40 (SEQ ID NO:21), mIL-12 p35 (SEQ ID NO:22), mIL-12 p35 (SEQ ID NO:23), hCCL4 (SEQ ID NO:24), mCCL4 (SEQ ID NO:25), hCCL21 (SEQ ID NO:26), mCCL21 (SEQ ID NO:27), hCXCL9 (SEQ ID NO:28), mCXCL9 (SEQ ID NO:29), hCXCL10 (SEQ ID NO:30), mCXCL10 (SEQ ID NO:31), hVEGF-C(SEQ ID NO:32), mVEGF-C(SEQ ID NO:33), mIFNβ (SEQ ID NO:39), hIFNβ (SEQ ID NO:40), mIFNα2 (SEQ ID NO:41), hIFNα2 (SEQ ID NO:42), mXCL1 (SEQ ID NO:43), hXCL1 (SEQ ID NO:44), mIL-15 super agonist (SEQ ID NO:45), or hIL-15 super agonist (SEQ ID NO:46) or to a peptide segment of hIL-15 (SEQ ID NO:16), mIL-15 (SEQ ID NO:17), hIL-21 (SEQ ID NO:18), mIL-21 (SEQ ID NO:19), hIL-12 p35 (SEQ ID NO:20), hIL-12 p40 (SEQ ID NO:21), mIL-12 p35 (SEQ ID NO:22), mIL-12 p35 (SEQ ID NO:23), hCCL4 (SEQ ID NO:24), mCCL4 (SEQ ID NO:25), hCCL21 (SEQ ID NO:26), mCCL21 (SEQ ID NO:27), hCXCL9 (SEQ ID NO:28), mCXCL9 (SEQ ID NO:29), hCXCL10 (SEQ ID NO:30), mCXCL10 (SEQ ID NO:31), hVEGF-C(SEQ ID NO:32), mVEGF-C(SEQ ID NO:33), mIFNβ (SEQ ID NO:39), hIFNβ (SEQ ID NO:40), mIFNα2 (SEQ ID NO:41), hIFNα2 (SEQ ID NO:42), mXCL1 (SEQ ID NO:43), hXCL1 (SEQ ID NO:44), mIL-15 super agonist (SEQ ID NO:45), or hIL-15 super agonist (SEQ ID NO:46) that retains cytokine activity. In some embodiments, the peptide is at least 85% identical to hIL-15 (SEQ ID NO:16), mIL-15 (SEQ ID NO:17), hIL-21 (SEQ ID NO:18), mIL-21 (SEQ ID NO:19), hIL-12 p35 (SEQ ID NO:20), hIL-12 p40 (SEQ ID NO:21), mIL-12 p35 (SEQ ID NO:22), mIL-12 p35 (SEQ ID NO:23), hCCL4 (SEQ ID NO:24), mCCL4 (SEQ ID NO:25), hCCL21 (SEQ ID NO:26), mCCL21 (SEQ ID NO:27), hCXCL9 (SEQ ID NO:28), mCXCL9 (SEQ ID NO:29), hCXCL10 (SEQ ID NO:30), mCXCL10 (SEQ ID NO:31), hVEGF-C(SEQ ID NO:32), mVEGF-C(SEQ ID NO:33), mIFNβ (SEQ ID NO:39), hIFNβ (SEQ ID NO:40), mIFNα2 (SEQ ID NO:41), hIFNα2 (SEQ ID NO:42), mXCL1 (SEQ ID NO:43), hXCL1 (SEQ ID NO:44), mIL-15 super agonist (SEQ ID NO:45), or hIL-15 super agonist (SEQ ID NO:46). In some embodiments, the peptide comprises or consists of or consist essentially of hIL-15 (SEQ ID NO:16), mIL-15 (SEQ ID NO:17), hIL-21 (SEQ ID NO:18), mIL-21 (SEQ ID NO:19), hIL-12 p35 (SEQ ID NO:20), hIL-12 p40 (SEQ ID NO:21), mIL-12 p35 (SEQ ID NO:22), mIL-12 p35 (SEQ ID NO:23), hCCL4 (SEQ ID NO:24), mCCL4 (SEQ ID NO:25), hCCL21 (SEQ ID NO:26), mCCL21 (SEQ ID NO:27), hCXCL9 (SEQ ID NO:28), mCXCL9 (SEQ ID NO:29), hCXCL10 (SEQ ID NO:30), mCXCL10 (SEQ ID NO:31), hVEGF-C(SEQ ID NO:32), mVEGF-C(SEQ ID NO:33), mIFNβ (SEQ ID NO:39), hIFNβ (SEQ ID NO:40), mIFNα2 (SEQ ID NO:41), hIFNα2 (SEQ ID NO:42), mXCL1 (SEQ ID NO:43), hXCL1 (SEQ ID NO:44), mIL-15 super agonist (SEQ ID NO:45), or hIL-15 super agonist (SEQ ID NO:46), or a fragment thereof.

In certain embodiments the IL-2 portion of the ECM-affinity peptide cytokine conjugate comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150 contiguous amino acids of SEQ ID NO:35 or SEQ ID NO:37. In one embodiment, the IL-2 peptide comprises a peptide that has at least or at most 70, 72, 74, 76, 78, 80, 82, 84, 86, 88, 90, 92, 94, 96, 98, 99, or 100% identity (or any range derivable therein) to SEQ ID NO:35 or SEQ ID NO:37 or to a peptide segment SEQ ID NO:35 or SEQ ID NO:37 that retains an IL-2 activity. In some embodiments, the peptide is at least 85% identical to SEQ ID NO:35 or SEQ ID NO:37. In some embodiments, the peptide comprises or consists of or consist essentially of SEQ ID NO:35 or SEQ ID NO:37 or a fragment thereof. His-tagged mouse IL-2 having the following sequence—PTSSSTSSSTAEA-QQQQQQQQQQQQHLEQLLMDLQELLSRME-NYRNLKLPRMLT FKFYLPKQATELKDLQCLEDELG-PLRHVLDLTQSKSFQLEDAENFISNIRVTVVKLKG SDNTFECQFDDESATVVDFLRRWIAFCQSIIST-SPQHHHHHH (SEQ ID NO:35). Human IL-2 having the following sequence—MYRMQLLSCIALSLALVTN-SAPTSSSTKKTQLQLEH LLLDLQMILNGIN-NYKNPKLTRMLTFKFYMPK-KATELKHLQCLEEELKPLEEVLNLA QSKNFHLRPRDLISNINVIVLELKGSETTFMCEYADE-TATIVEFLNRWITFCQSIISTLT (SEQ ID NO:37).

Linkers, such as amino acid or peptidimimetic sequences may be inserted between the peptide and cytokine sequence. Linkers may have one or more properties that include a flexible conformation, an inability to form an ordered secondary structure or a hydrophobic or charged character which could promote or interact with either domain. Examples of amino acids typically found in flexible protein regions may include Gly, Asn, and Ser. Other near neutral amino acids, such as Thr and Ala, may also be used in the linker sequence. The length of the linker sequence may vary without significantly affecting the function or activity of the fusion protein (see, U.S. Pat. No. 6,087,329). In a particular aspect, a peptide and cytokine are joined by a peptide sequence having from about 1, 2, 3, 4, 5, 6, 7, 8, 9, 10, 11, 12, 13, 14, 15, 16, 17, 18, 19, 20, 21, 22, 23, 24, to 25 amino acid residues. Examples of linkers may also include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST). Linkers further include a linear carbon chain, such as $C_N$ (where N=1-100 carbon atoms, e.g., $C_1$, $C_2$, $C_3$, $C_4$, $C_5$, $C_6$, $C_7$, $C_8$). In some embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker. In some embodiments, the linker is sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Further, the linker may be maleimidocaproyl (mc).

In some embodiments, the ratio of peptide to cytokine is about 1:1 to 10:1. In some embodiments, the ratio of peptide to cytokine is at least, at most, or about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 30:1, 35:1, 40:1, 45:1, 50:1, or 100:1 (or any range there between).

Further aspects relate to methods for treating cancer in a subject comprising administering a composition including a ECM-affinity peptide coupled to a cytokine to a subject. In some embodiments, the composition is administered intravenously, or by intratumoral, peri-tumoral, intraarterial, or transcatheter injection. In some embodiments, the vWF or decorin containing polypeptides described herein (i.e., those having one or more peptides having all or part of a sequence of SEQ ID NO:3, SEQ ID NO:11, SEQ ID NO:13, SEQ ID NO:15, SEQ ID NO:34) are administered systemically. The systemic administration may be parenteral or intravenous, for example.

In some embodiments, the administered dose of a cytokine operatively linked to the ECM-affinity peptide is less than the minimum effective dose of the cytokine administered without the ECM-affinity peptide. In some embodiments, the administered dose of the cytokine operatively linked to the ECM-affinity peptide is at least 10% less than the minimum effective dose of the cytokine administered without the ECM-affinity peptide. In some embodiments, the administered dose of the cytokine operatively linked to the ECM-affinity peptide is at least 5, 10, 15, 20, 25, 30, 35, 40, 45, 50, 55, 60, 65, 70, 75, or 80% less (or any derivable range therein) than the minimum effective dose of the cytokine administered without the ECM-affinity peptide.

In some embodiments, the subject has been diagnosed with a cancer. In some embodiments, the cancer is melanoma, colon cancer, lung cancer, prostate cancer, ovarian cancer, testicular cancer, brain cancer, glioblastoma, pediatric tumors, germ cell tumors, rectal cancer, gastric cancer, esophageal cancer, tracheal cancer, head and neck cancer, pancreatic cancer, liver cancer, breast cancer, cervical cancer, and vulvar cancer. In certain embodiments, the cancer is melanoma or colon cancer. In some embodiments, the cancer is non-hematological. In some embodiments, the cancer includes a solid tumor. In some embodiments, the cancer is distant metastasis. In some embodiments, the patient has been previously treated for the cancer. In some embodiments, the subject was resistant to the previous cancer treatment. In some embodiments, the subject was determined to be a poor responder to the cancer treatment.

The methods can further include administering an additional cancer therapy. In some embodiments, the additional cancer therapy comprises radiation, vaccination, chemotherapy, adoptive T-cell therapy, cytokine therapy, anti-CD47 antibodies, anti-GD2 antibodies, or immunologic adjuvants.

In some embodiments, the method further comprises administration of a second cytokine operatively linked to the same or different ECM-affinity peptide.

The term "cytokine polypeptide" as used herein refers to a polypeptide, which is cytokine or a receptor binding domain thereof and retains at a portion of cytokine activity.

The term "cytokine activity" as used herein refers to the activities which cytokines possess or are able to exert in vivo, including but not limited to the promotion of proliferation, immunoglobulin class switching and antibody secretion of B cells; differentiation of memory B cells, or prevention of their apoptosis; promoting macrophages' secretion of interleukin-12 to activate type I helper T cells or secrete chemokines; promoting macrophages to produce nitric oxide to enhance the defense capability against microorganisms; promoting the maturation and activation of dendritic cells; regulation of the maturation and differentiation of T cells; promoting the cytotoxicity and the production of a variety of different cytokines of natural killer cells; activation of monocytes and macrophages; and stimulation of T cells and B cells to continuously express MHC, etc.

The term "chemokine polypeptide" as used herein refers to a cytokine polypeptide that is a chemokine or a receptor binding domain thereof, wherein the chemokine includes but is not limited to CXC chemokines, CC chemokines, C chemokines and CX3C chemokines.

The term "chemokine activity" as used herein refers to the activities which chemokines possess or are able to exert in vivo, including but not limited to, chemotaxis of a variety of immune cells (including monocytes, macrophages, T cells, B cells, natural killer cells, dendritic cells and neutrophils, etc.).

The terms "protein", "polypeptide" and "peptide" are used interchangeably herein when referring to a gene product comprising a polymer of amino acids.

The terms "subject," "mammal," and "patient" are used interchangeably. In some embodiments, the subject is a mammal. In some embodiments, the subject is a human. In some embodiments, the subject is a mouse, rat, rabbit, dog, donkey, or a laboratory test animal such as fruit fly, zebrafish, etc.

It is contemplated that the methods and compositions include exclusion of any of the embodiments described herein.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

The feature or features of one embodiment may be applied to other embodiments, even though not described or illustrated, unless expressly prohibited by this disclosure or the nature of the embodiments.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb. A composition "consisting essentially of" the recited elements excludes any further active ingredients but does not exclude pharmaceutical excipients, buffers, structural components, etc.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-E. Collagen binding domain (CBD) protein-fused IL-2 bind to collagen I and III with high affinity. (1A) Schematic of fusion of the vWF A3 recombinant protein to IL-2. (1B) IL-2 and CBD-IL-2 were analyzed by SDS-PAGE under reducing conditions with coomassie blue staining. (1C) Affinities ($K_D$ values are shown) of IL-2 and CBD-IL-2 against collagen type I and collagen type III, recombinant mouse (rm) IL-2Rα were measured by ELISA. N.D.=not determined because of low signals. (1D) Graph with [concentrations] vs [signals] is shown (n=4). (1E) CTLL-2 cells are cultured in the presence of IL-2 or CBD-IL-2. After 48 hrs of culture, cell proliferation was analyzed. Two experimental repeats. Statistical analyses were done using ANOVA with Tukey's test. **$p<0.01$.

FIGS. 2A-B. CBD fusion reduces potential treatment-related toxicity of IL-2. (2A) $8\times10^5$ MMTV-PyMT cells were inoculated on day 0. Fifty µg of DyLight 800-labeled CBD was injected i.v. when tumor volume reached 500 mm³. Fluorescence analysis of each organ revealed the bio-distribution of CBD protein after 48 hrs of injection. (2B) $5\times10^5$ B16F10 cells were inoculated on day 0. CBD-IL-2 (12 µg) or IL-2 (6 µg) was injected i.v. on day 4. Blood serum was collected on day 5 and serum concentrations of IFNγ was measured (mean±SEM). Statistical analyses were done using ANOVA with Tukey's test. Two experimental repeats. *$p<0.05$; N.S.=not significant.

FIGS. 3A-B. CBD-IL-2 treatment reduces growth rate of B16F10 melanoma and CT26 colon carcinoma. (3A) $5\times10^5$ B16F10 cells (3B) $5\times10^5$ CT26 cells were inoculated on day 0. CBD-IL-2 (12 µg), IL-2 (6 µg) or PBS was administered i.v. on (3A) day 4 or (3B) day 5. Graphs depict tumor volume until the first mouse died. Tumor volumes are presented as mean±SEM. (3A) n=6 (3B) n=6. Two experimental repeats. Statistical analyses were done using ANOVA with Tukey's test for tumor size using the values of each day. *$p<0.05$; **$p<0.01$.

FIGS. 4A-4B. CBD fusion to IL-12 improves α-PD-L1 therapy. $5\times10^5$ B16F10 cells were inoculated intradermally on day 0. 25 µg IL-12, 25 µg (IL-12 molar eq.) CBD-IL-12 or PBS was administered on days 7, 17 and 27 intravenously. 100 µg of α-PD-L1 or PBS was administered on days 8, 18 and 28 intraperitoneally. (A) Tumor growth rates and (B) survival rates are shown. PBS and α-PD-L1, n=7. α-PD-L1+IL-12 and α-PD-L1+CBD-IL-12, n=12. Tumor volumes are represented as mean±SEM. Statistical analysis for tumor growth curves was done using unpaired Mann-Whitney test (between α-PD-L1+IL-12 and α-PD-L1+CBD-IL-12). Statistical analysis for survival curve was done using Log-rank test. *$p<0.05$, **$p<0.01$.

FIGS. 5A-5B. CBD-IL-12 results in synergistic antitumor immunity with checkpoint inhibitors. $5\times10^5$ B16F10 cells were inoculated intradermally on day 0. 25 µg (IL-12 molar eq.) CBD-IL-12 or PBS was administered on days 8, 13 and 18 intravenously. α-PD-L1 or α-PD-1+α-CTLA-4 (100 µg per antibody per dose) were administered on days 9, 14 and 19 intraperitoneally. (A) Tumor growth rates and (B) survival rates are shown. PBS, α-PD-L1, α-PD-1+α-CTLA-4, n=5. CBD-IL-12, α-PD-L1+CBD-IL-12, n=10. α-PD-1+α-CTLA-4+CBD-IL-12, n=11. Tumor volumes are represented as mean±SEM. Statistical analysis for survival curve was done using Log-rank test. *$p<0.05$, **$p<0.01$.

FIGS. 6A-6D. CBD-CCL4 fusion protein binds to collagen I and collagen III and maintains its activity. (A) WT CCL4 and CBD-CCL4 were analyzed by SDS-PAGE followed by Coomassie blue staining. (B,C) Affinity of CBD-CCL4 against (B) collagen I and (C) collagen III was measured by SPR. SPR chips were functionalized with collagen I (~500 RU) and collagen III (~700 RU), and the CBD-CCL4 was flowed over the chips at indicated concentrations. Curves represent the obtained specific responses (in resonance units (RU)) to CBD-CCL4. Experimental curves were fitted with 1:1 Langmuir fit model. Binding kinetics values [dissociation constants ($K_D$) and rate constants ($k_{on}$ and $k_{off}$)] determined from the fitted curves are shown. (D) GPCR activation assay comparing signaling of WT CCL4 and CBD-CCL4 in ThP1 monocytes. $EC_{50}$ values were calculated using a non-linear dose-response curve fit model. Each point represents mean±SEM, n=3.

FIGS. 7A-7B. CBD-CCL4 fusion enhances blood plasma circulation time and improves tumor localization relative to WT CCL4. (A) Blood plasma pharmacokinetics was analyzed using DyLlight 800-labeled WT CCL4 or CBD-CCL4 in B16F10 melanoma. 4 d after intradermal inoculation with $5\times10^5$ cells, mice were administered 25 µg WT CCL4 or molar equivalent CBD-CCL4 (25 µg CCL4 basis, or 93 µg CBD-CCL4) via i.v. injection. Blood was collected at the indicated time points, and plasma was separated and analyzed for CCL4 concentration. Each point represents mean±SEM, n=4. (B) Biodistribution was analyzed using DyLlight 647-labeled WT CCL4 or CBD-CCL4 in EMT6 breast cancer. $5\times10^5$ EMT6 cells were inoculated in the mammary fat pad. When the tumor volume reached 500 mm³, 25 g WT CCL4 or molar equivalent CBD-CCL4 (25 µg CCL4 basis, or 93 µg CBD-CCL4) was given via i.v. injection. Florescent intensity in each tumor was measured using an IVIS imaging system, converted to percent injected dose using a known standard series, and normalized to the weight of the tumor. Each bar represents mean±SEM, n=3. **$p<0.01$.

FIGS. 8A-8H. CBD-CCL4 fusion recruits T cells, DCs, and improves efficacy of CPI therapy in B16F10 melanoma. Mice were intradermally injected with $5\times10^5$ cells; 4 d later, mice were treated with WT CCL4 (25 µg given via i.v. injection) or molar equivalent CBD-CCL4 (25 µg CCL4 basis, or 93 µg CBD-CCL4, given via i.v. injection) in combination with CPI antibody therapy consisting of 100 g each αPD-L1 and αCTLA4 given via i.p. injection. CPI therapy alone was administered as control. (A) Tumor growth was monitored over time until 10 d post tumor inoculation, at which point tumors were harvested and processed for flow cytometry analysis. (B-H) Immune cell composition was evaluated, where graphs depict the number of (B) $CD45^+$ leukocytes, (C) $CD103^+$ $CD11c^+$ $MHCII^{Hi}$ DCs, (D) $CD8^+$ T cells, (E) $NK1.1^+$ $CD3^-$ NK cells, (F) total $CD11c^+$ DCs, (G) $CD4+$ T cells, and (H) $FoxP3^+$ $CD25^+$ Tregs (of total $CD4^+$ T cells). Bars represent mean±SEM, n=11-13. *$p<0.05$; $p<0.01$; *$p<0.001$; ****$p<0.0001$.

FIGS. 9A-9F. CBD-CCL4 combination therapy exhibits strong correlation between tumor growth and infiltration of $CD103^+$ DCs and $CD8^+$ T cells. (A-F) Regression analysis comparing the number of tumor-infiltrating cells with tumor volume was performed using the results obtained in FIG. 3. Correlations between (A) tumor volume and $CD103^+$ $CD11^{c+}$ $MHCII^{Hi}$ DCs, (B) tumor volume and $CD8^+$ T cells, (C) $CD103^+$ $CD11^{c+}$ $MHCII^{Hi}$ DCs and $CD8^+$ T cells, (D) tumor volume and $NK1.1^+$ $CD3^-$ NK cells (E) tumor volume and total $CD11^{c+}$ DCs, and (F) tumor volume and total $CD45^+$ leukocytes.

FIGS. 10A-10H. CBD-CCL4 combination treatment recruits T cells, DCs, and improves efficacy of CPI therapy in EMT6 breast cancer. Mice were subcutaneously injected with $5\times10^5$ cells; 6 d and 9 d after inoculation, mice were treated with WT CCL4 (25 µg given via i.v. injection) or molar equivalent CBD-CCL4 (25 µg CCL4 basis, or 93 µg CBD-CCL4, given via i.v. injection) in combination with CPI antibody therapy consisting of 100 g each αPD-L1 and αCTLA4 given via i.p. injection. CPI therapy alone was administered as control. (A) Tumor growth was monitored over time until 10 d post tumor inoculation, at which point tumors were harvested and processed for flow cytometry analysis. (B-H) Immune cell composition was evaluated, where graphs depict the number of (B) CD45$^+$ leukocytes, (C) CD103$^+$ CD11$^{c+}$ MHCII$^{Hi}$ DCs, (D) CD8$\alpha^+$ CD11$^{c+}$ MHCII$^{Hi}$ DCs (E) CD8$^+$ T cells, (F) total CD11$^{c+}$ DCs, (G) CD4+ T cells, and (H) FoxP3+CD25+ Tregs (of total CD4+ T cells). Bars represent mean±SEM, n=7-9. *p<0.05; **p<0.01.

FIGS. 11A-11D. CBD-CCL4 combination treatment slows growth of established B16F10 melanoma and significantly prolongs survival. Mice were intradermally injected with 5×10$^5$ cells; 7 d later, once tumor volume exceeded 50 mm$^3$, mice were treated with CBD-CCL4 (25 μg CCL4 basis, or 93 μg CBD-CCL4, given via i.v. injection) in combination with CPI antibody therapy consisting of 100 μg each αPD-L1 and αCTLA4 given via i.p. injection. CPI therapy alone was administered as comparison. (A) Tumor growth curves until the first mouse died, (B) survival curves, and individual growth curves for (C) CPI therapy alone or (D) CBD-CCL4 combination therapy are shown. Graphs depict mean±SEM, n=5. p<0.01; *p<0.001; ****p<0.0001.

FIGS. 12A-12B. CBD-CCL4 therapy synergizes with αPD-1 immunotherapy to slow growth of CT26 and MC38 colon carcinoma. Mice were intradermally injected with 5×10$^5$ CT26 or MC38 cells; 5 d after inoculation, mice were treated with WT CCL4 (25 g given via i.v. injection) or molar equivalent CBD-CCL4 (25 μg CCL4 basis, or 93 μg CBD-CCL4 given via i.v. injection) in combination with 100 μg αPD-1 given via i.p. injection. 100 μg αPD-1 alone was administered as control. Graphs depict growth curves of (A) CT26 and (B) MC38 tumor models until the first mouse died. Bars represent mean±SEM, n=5. *p<0.05; p<0.01; **p<0.0001.

FIG. 13A-13D. CBD-CCL4 in combination with CPI therapy slows growth of spontaneous MMTV-PyMT breast cancer. MMTV-PyMT mice were monitored until total tumor burden reached 100 mm$^3$. At this point, mice were treated with CBD-CCL4 (25 g CCL4 basis, or 93 μg CBD-CCL4, given via i.v. injection) in combination with CPI antibody therapy consisting of 100 g each αPD-L1 and αCTLA4 given via i.p. injection. CPI therapy alone was administered as comparison. Identical dosing was given 7 d and 14 d after the initial treatment. (A) Tumor growth curves until first two mice died, (B) survival curves, and individual growth curves for (C) CPI therapy alone or (D) CBD-CCL4 combination therapy are shown. Graphs depict mean±SEM, n=6. *p<0.05; **p<0.01.

DETAILED DESCRIPTION

Figure 1E:
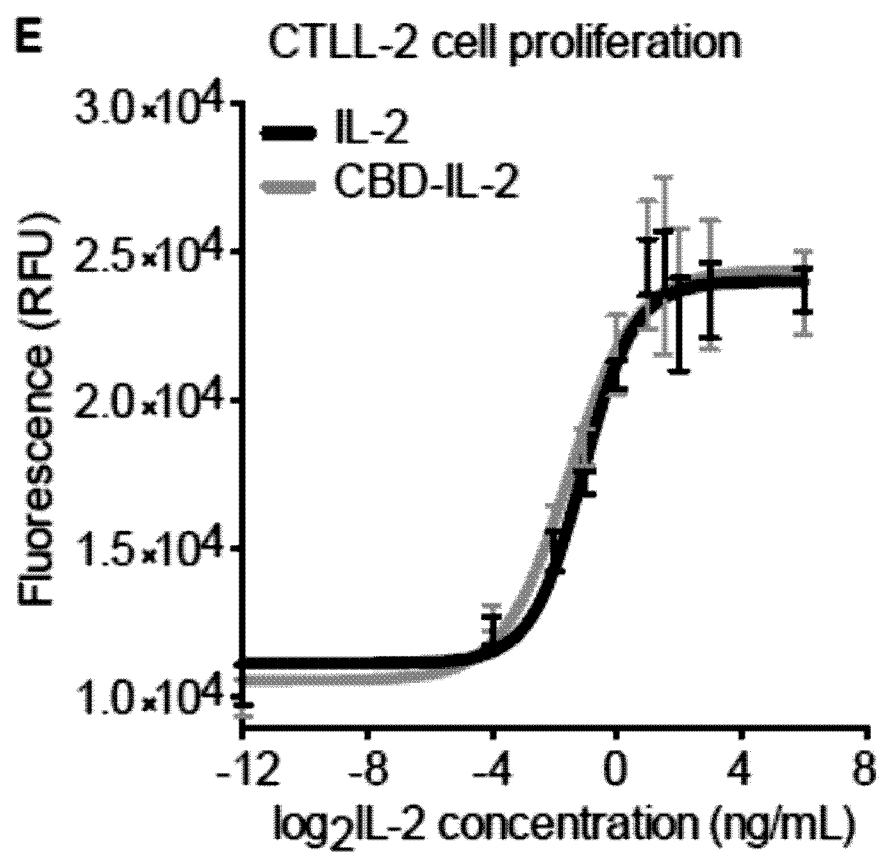

Cytokines and chemokines, referred to herein generally as cytokines, have been shown to exhibit considerable antitumor activity, but previous studies have reported instances of narrow therapeutic windows and/or treatment-related adverse events. The methods and compositions described herein provide for localized therapy with a cytokine that is retained intra- or peri-tumorally, limiting systemic exposure and reducing side-effects that, in some cases, can be so severe that either the therapy has to be discontinued or an effective dose is not achievable. The examples provided herein demonstrate enhanced tumor tissue retention and lower concentrations in blood plasma following ECM-affinity peptide conjugation, reducing systemic side effects. Intravenous (iv) injections of the compositions described herein significantly delayed tumor growth, prolonging survival compared to controls in mouse models for melanoma and colon cancer. This simple and translatable approach of engineered ECM-binding cytokines represent a novel approach in cancer therapy.

IL-2 was used as a representative cytokine to demonstrate the concept of localizing cytokines to the tumor vasculature via an ECM affinity peptides, e.g., collagen binding domains (CBDs). Cytokine immunotherapy with interleukin-2 (IL-2) exhibits considerable antitumor activity in animal models and the clinic. The inventors have tested the use of CBDs to target leaky vasculature by engineered a fusion protein of IL-2 to a CBD from the von Willebrand Factor (vWF) A3 domain; the fusion protein can be administered intravenously and target the tumor microenvironment via its leaky vasculature. This demonstrates the use of such fusions/conjugates to access the tumor stroma. Below in the examples it is shown that CBD protein localizes to tumor tissue; CBD-IL-2 showed a lower serum concentrations after injection; and CBD-IL-2 significantly delayed tumor growth compared to wild-type IL-2 in murine melanoma and colon cancer models. This simple and translatable approach of an engineered collagen-binding cytokine presents a novel approach to cancer immunotherapeutics.

Blood vessels are normally lined with tightly linked cells, called endothelial cells, that form an impermeable barrier. Vascular leak occurs when small blood vessels, generally a capillary or venule, become leaky and release fluid. Vascular leak can occur under a variety of conditions, including tumor microenvironment or chronic inflammation, and can affect almost all the organ beds. Methods and compositions for treatment of or targeting of areas of vacular permeability in chronic inflammation associated disorders such as insulin resistance, diabetes, cardiovascular disease, metabolic disorders, and cancer are contemplated In the treatment of a disease associated with an increase of vascular permeability a collagen binding domain described herein may be effectively used as a pharmaceutical composition for preventing and/or treating such a disease. In this aspect, the pharmaceutical composition for preventing and/or treating a disease associated with vascular permeability can include the localization of a therapeutic to an area of vascular leakage or permeability. The therapeutic can be a peptide, polypeptide, compound, antibody, genes (for example, antisense oligonucleotide, siRNA, shRNA, microRNA, and the like), aptamers, therapeutic cells, radiopharmaceutical drugs.

I. Cytokines and Chemokines

Cytokines are a group of proteins that cells release upon excitation (only very few cytokines are expressed on cell membranes). Cytokines produced by cells can affect target cells nearby or through blood circulation at very low concentration. They have broad functions on promoting growth, differentiation, and activation of target cells. Many cytokines can target immune cells and play a role in immune response. Based on structural and functional differences, cytokines may be broadly divided into chemokines, interleukins, growth factors, transforming growth factors, colony stimulating factors, tumor necrosis factors, and interferons.

Interleukins are a group of cytokines first identified to be expressed by white blood cells (leukocytes). The function of the immune system depends in a large part on interleukins. The majority of interleukins are synthesized by helper CD4 T lymphocytes, as well as monocytes, macrophages, and endothelial cells. Generally interleukins promote the development and differentiation of T and B lymphocytes, and hematopoietic cells. Interleukin 2 (IL-2) is classified into the hematopoietin family, the family including a number of cell growth-related hormones or other cytokines. Functions of IL-2 include: regulating the maturation and differentiation of T cells, stimulating proliferation and antibody secretion of B cells, promoting cytotoxicity of natural killer cells, and activating monocytes and macrophages. IL-2 can also stimulate T cells and B cells to continue expressing MHC, and also stimulate natural killer cells to produce several different cytokines, including TNF-α, IFN-γ and granulocyte/macrophage colony stimulating factor (GM-CSF). Studies have shown that IL-2 has anti-tumor and vaccine-enhancing effects.

Chemokines are a group of cytokines able to attract leukocytes. Chemokines are typically positively charged, secreted proteins having small molecular weights. Their main function is to attract immune cells to a region having tissue injuries or pathogen infection, allowing leukocytes to subsequently perform phagocytosis or elicit inflammation against pathogens at this specific site. Leukocytes attracted by chemokines may include neutrophils, monocytes/macrophages, natural killer cells, dendritic cells and other leukocytes, which are of innate immunity; and T lymphocytes (T cells) or B lymphocytes (B cells) of adaptive immunity. Typically chemokines have four highly conserved cysteine (C) forming disulfide bonds to stabilize their structure. Based on different numbers of amino acids between the first two cysteines and the procession of the first cysteine or not, they may be classified into four subfamilies of CXC (or α), CC (or β), C (or γ) and CX3C. Stromal cell-derived factor-1 (SDF-1) is classified into the CXC subfamily of chemokines, and is also known as CXC ligand 12 (CXCL12).

In certain embodiments the cytokine is IL-2. Cancer immunotherapy has shown considerable therapeutic effects in the clinic. As a cytokine drug, interleukin-2 (IL-2: aldesleukin) has been approved by the US Food and Drug Administration (FDA) (Jiang et al., *Oncoimmunology* 5:e1163462, 2016) for treatment of advanced melanoma and renal cell cancer. Aldesleukin shows high response rates, prolonging survival, whereas it has a narrow therapeutic window due to induction of severe adverse events (Rosenberg et al., *N Engl J Med* 313:1485-1492, 1985). IL-2 is mainly secreted from CD4$^+$ T cells and, to lesser extent, CD8$^+$ T cells and natural killer (NK) cells (Boyman and Sprent, *Nature reviews. Immunology* 12:180-190, 2012). IL-2 induces proliferation and activation of T cells, B cells, and NK cells (Boyman and Sprent, *Nature reviews. Immunology* 12:180-190). Although IL-2 activates the immune system at high concentrations, IL-2 reverses its effect at low concentration to induce and maintain regulatory T cells (Tregs), which are immunosuppressive cells (Jiang et al., *Oncoimmunology* 5:e1163462, 2016). Because of its fast half-life in the blood, engineering of IL-2 fusion protein to increase its half-life has been proposed and shows higher efficacy compared to its wild-type form (Zhu et al., *Cancer Cell* 27:489-501, 2015).

In another embodiment the cytokine can be selected from IL-12, IL-15, IL-21, CC14, CCL21, CXCL9, CXCL10, VEGF-C, or other cytokine having anti-tumor properties.

Human IL-15 has an amino acid sequence of-
(SEQ ID NO: 16)
MNWVNVISDLKKIEDLIQSMHIDATLYTESDVHPSCKVTAMKCFLLELQV

ISLESGDASIHDTVENLIILANNSLSSNGNVTESGCKECEELEEKNIKEF

LQSFVHIVQMFINTS.

Mouse IL-15 has an amino acid sequence of-
(SEQ ID NO: 17)
MNWIDVRYDLEKIESLIQSIHIDTTLYTDSDFHPSCKVTAMNCFLLELQV

ILHEYSNMTLNETVRNVLYLANSTLSSNKNVAESGCKECEELEEKTFTEF

LQSFIRIVQMFINTS.

Human IL-21 has an amino acid sequence of
(SEQ ID NO: 18)
MQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEK

KPPKEFLERFKSLLQKMIHQHLSSRTHGSEDS.

Mouse IL-21 has an amino acid sequence of-
(SEQ ID NO: 19)
MHKSSPQGPDRLLIRLRHLIDIVEQLKIYENDLDPELLSAPQDVKGHCEH

AAFACFQKAKLKPSNPGNNKTFIIDLVAQLRRRLPARRGGKKQKHIAKCP

SCDSYEKRTPKEFLERLKWLLQKMIHQHLS.

Human IL-12 p35 Subunit has an amino acid sequence of-
(SEQ ID NO: 20)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS.

Human IL-12 p40 Subunit has an amino acid sequence of-
(SEQ ID NO: 21)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTESVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS.

Mouse IL-12 p35 Subunit has an amino acid sequence of-
(SEQ ID NO: 22)
RVIPVSGPARCLSQSRNLLKTTDDMVKTAREKLKHYSCTAEDIDHEDITR

DQTSTLKTCLPLELHKNESCLATRETSSTTRGSCLPPQKTSLMMTLCLGS

IYEDLKMYQTEFQAINAALQNHNHQQIILDKGMLVAIDELMQSLNHNGET

LRQKPPVGEADPYRVKMKLCILLHAFSTRVVTINRVMGYLSSA.

Mouse IL-12 p40 Subunit has an amino acid sequence of-
(SEQ ID NO: 23)
MWELEKDVYVVEVDWTPDAPGETVNLTCDTPEEDDITWTSDQRHGVIGSG

KTLTITVKEFLDAGQYTCHKGGETLSHSHLLLHKKENGIWSTEILKNEKN

KTFLKCEAPNYSGRFTCSWLVQRNMDLKFNIKSSSSSPDSRAVTCGMASL

SAEKVTLDQRDYEKYSVSCQEDVTCPTAEETLPIELALEARQQNKYENYS

-continued

TSFFIRDIIKPDPPKNLQMKPLKNSQVEVSWEYPDSWSTPHSYFSLKFFV
RIQRKKEKMKETEEGCNQKGAFLVEKTSTEVQCKGGNVCVQAQDRYYNSS
CSKWACVPCRVRS.

Human CCL4 has an amino acid sequence of-
(SEQ ID NO: 24)
APMGSDPPTACCFSYTARKLPHNFVVDYYETSSLCSQPAVVFQTKRGKQV
CADPSESWVQ EYVYDLELN.

Mouse CCL4 has an amino acid sequence of-
(SEQ ID NO: 25)
APMGSDPPTSCCFSYTSRQLHRSFVMDYYETSSLCSKPAVVFLTKRGRQI
CANPSEPWVTEYMSDLELN.

Human CCL21 has an amino acid sequence of-
(SEQ ID NO: 26)
SDGGAQDCCLKYSQRKIPAKVVRSYRKQEPSLGCSIPAILFLPRKRSQAE
LCADPKELWVQQLMQHLDKTPSPQKPAQGCRKDRGASKTGKKGKGSKGCR
KTERSQTPKGP.

Mouse CCL21 has an amino acid sequence of-
(SEQ ID NO: 27)
SDGGGQDCCLKYSQKKIPYSIVRGYRKQEPSLGCPIPAILFLPRKHSKPE
LCANPEEGWVQNLMRRLDQPPAPGKQSPGCRKNRGTSKSGKKGKGSKGCK
RTEQTQPSRG.

Human CXCL9 has an amino acid sequence of-
(SEQ ID NO: 28)
TPVVRKGRCSCISTNQGTIHLQSLKDLKQFAPSPSCEKIEIIATLKNGVQ
TCLNPDSADVKELIKKWEKQVSQKKKQKNGKKHQKKKVLKVRKSQRSRQK
KTT.

Mouse CXCL9 has an amino acid sequence of-
(SEQ ID NO: 29)
TLVIRNARCSCISTSRGTIHYKSLKDLKQFAPSPNCNKTEIIATLKNGDQ
TCLDPDSANVKKLMKEWEKKINQKKKQKRGKKHQKNMKNRKPKTPQSRRR
SRKTT.

Human CXCL10 has an amino acid sequence of-
(SEQ ID NO: 30)
VPLSRTVRCTCISISNQPVNPRSLEKLEIIPASQFCPRVEIIATMKKKGE
KRCLNPESKAIKNLLKAVSKERSKRSP.

Mouse CXCL10 has an amino acid sequence of-
(SEQ ID NO: 31)
IPLARTVRCNCIHIDDGPVRMRAIGKLEIIPASLSCPRVEIIATMKKNDE
QRCLNPESKTIKNLMKAFSQKRSKRAP.

Human VEGF-C has an amino acid sequence of-
(SEQ ID NO: 32)
AHYNTEILKSIDNEWRKTQCMPREVCIDVGKEFGVATNTFFKPPCVSVYR
CGGCCNSEGLQCMNTSTSYLSKTLFEITVPLSQGPKPVTISFANHTSCRC
MSKLDVYRQVHSIIRR.

Mouse VEGF-C has an amino acid sequence of-
(SEQ ID NO: 33)
TEETIKFAAAHYNTEILKSIDNEWRKTQCMPREVCIDVGKEFGVATNTFF
KPPCVSVYRCGGCCNSEGLQCMNTSTSYLSKTLFEITVPLSQGPKPVTIS
FANHTSCRCMSKLDVYRQVHSIIRR.

Mouse IFNβ has an amino acid sequence of-
(SEQ ID NO: 39)
MNNRWILHAAFLLCFSTTALSINYKQLQLQERTNIRKCQELLEQLNGKIN
LTYRADFKIPMEMTEKMQKSYTAFAIQEMLQNVFLVFRNNFSSTGWNETI
VVRLLDELHQQTVFLKTVLEEKQEERLTWEMSSTALHLKSYYWRVQRYLK
LMKYNSYAWMVVRAEIFRNFLIIRRLTRNFQN.

Human IFNβ has an amino acid sequence of-
(SEQ ID NO: 40)
MSYNLLGFLQRSSNFQCQKLLWQLNGRLEYCLKDRMNFDIPEEIKQLQQF
QKEDAALTIYEMLQNIFAIFRQDSSSTGWNETIVENLLANVYHQINHLKT
VLEEKLEKEDFTRGKLMSSLHLKRYYGRILHYLKAKEYSHCAWTIVRVEI
LRNFYFINRLTGYLRN.

Mouse IFNα2 has an amino acid sequence of-
(SEQ ID NO: 41)
CDLPHTYNLRNKRALKVLAQMRRLPFLSCLKDRQDFGFPLEKVDNQQIQK
AQAIPVLRDLTQQTLNLFTSKASSAAWNTTLLDSFCNDLHQQLNDLQTCL
MQQVGVQEPPLTQEDALLAVRKYFHRITVYLREKKHSPCAWEVVRAEVWR
ALSSSVNLLPRLSEEKE.

Human IFNα2 has an amino acid sequence of-
(SEQ ID NO: 42)
MALTFALLVALLVLSCKSSCSVGCDLPQTHSLGSRRTLMLLAQMRKISLF
SCLKDRHDFGFPQEEFGNQFQK.

Mouse XCL1 has an amino acid sequence of-
(SEQ ID NO: 43)
VGTEVLEESSCVNLQTQRLPVQKIKTYIIWEGAMRAVIFVTKRGLKICAD
PEAKWVKAAIKTVDGRASTRKNMAETVPTGAQRSTSTAITLTG.

Human XCL1 has an amino acid sequence of-
(SEQ ID NO: 44)
GSEVSDKRTCVSLTTQRLPVSRIKTYTITEGSLRAVIFITKRGLKVCADP
QATWVRDVVRSMDRKSNTRN NMIQTKPTGTQQSTNTAVTLTG.

Mouse IL-15 super agonist has an amino acid sequence of-
(SEQ ID NO: 45)
GTTCPPPVSIEHADIRVKNYSVNSRERYVCNSGFKRKAGTSTLIECVINK
NTNVAHWTTPSLKCIRDPSLAHYSPVPTVVTPKVTSQPESPSPSAKEPEA
SGGSGGGSGGGSGGGGSLQNWIDVRYDLEKIESLIQSIHIDTTLYTDSD
FHPSCKVTAMNCFLLELQVILHEYSNMTLNETVRNVLYLANSTLSSNKNV
AESGCKECEELEEKTFTEFLQSFIRIVQMFINTS.

Human IL-15 super agonist has an amino acid sequence of-
(SEQ ID NO: 46)
ITCPPPMSVEHADIWVKSYSLYSRERYICNSGFKRKAGTSSLTECVLNKA
TNVAHWTTPSLKCIRDVDDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGKGGGGS -continued

GGGGSGGGGSNWVNVISDLKKIEDLIQSMHIDATLYTESDVHPSCKVTAM

KCFLLELQVISLESGDASIHDTVENLIILANDSLSSNGNVTESGCKECEE

LEEKNIKEFLQSFVHIVQMFINTS.

II. ECM-Affinity Peptides

Collagen is an extracellular matrix (ECM)-protein that regulates a variety of cellular biological functions, such as proliferation, differentiation, and adhesion in both normal and tumor tissue (Ricard-Blum, *Cold Spring Harb Perspect Biol* 3:a004978, 2011). Collagen is the most abundant protein in the mammalian body and exists in almost all tissues in one or more of 28 isoforms (Ricard-Blum, *Cold Spring Harb Perspect Biol* 3:a004978, 2011). The blood vessel sub-endothelial space is rich in collagen. Because of its insolubility under physiological conditions, collagen barely exists within the blood (Dubois et al., *Blood* 107:3902-06, 2006; Bergmeier and Hynes, *Cold Spring Harb Perspect Biol* 4:a005132, 2012). Tumor vasculature is reported to be permeable due to an abnormal structure (Nagy et al., *British journal of cancer* 100:865, 2009). Thus, with its leaky vasculature, collagen is exposed in the tumor (Liang et al., *Journal of controlled release* 209:101-109, 2015; Liang et al., *Sci Rep* 6:18205, 2016; Yasunaga et al., *Bioconjugate chemistry* 22:1776-83, 2011; Xu et al. *The Journal of cell biology* 154:1069-80, 2001; Swartz and Lund, *Nat Rev Cancer* 12:210-19). Also, tumor tissue contains increased amounts of collagen compared to normal tissues (Zhou et al. *J Cancer* 8:1466-76, 2017; Provenzano et al. *BMC Med* 6:11, 2008).

von Willebrand factor (vWF) is a blood coagulation factor and binds to both type I and type III collagen, and the adhesion receptor GPIbα on blood platelets (Lenting et al., *Journal of thrombosis and haemostasis:JTH* 10:2428-37, 2012; Shahidi *Advances in experimental medicine and biology* 906:285-306, 2017). When injured, collagen beneath endothelial cells is exposed to blood plasma, and vWF-collagen binding initiates the thrombosis cascade (Shahidi *Advances in experimental medicine and biology* 906:285-306, 2017; Wu et al. *Blood* 99:3623-28, 2002). The vWF A domain has the highest affinity against collagen among reported non-bacterial origin proteins/peptides (Addi et al., *Tissue Engineering Part B: Reviews*, 2016). Particularly within the A domain, the A3 domain of vWF has been reported as a collagen binding domain (CBD) (Ribba et al. *Thrombosis and haemostasis* 86:848-54, 2001). As described above, the inventors contemplated that a fusion protein with the vWF A3 CBD may achieve targeted cytokine immunotherapy even when injected systemically due to exposure of collagen via the leaky tumor vasculature.

Embodiments of the disclosure relate to ECM-affinity peptides. In some embodiments, the ECM-affinity peptide is a peptide from von Willebrand factor (vWF). The sequence of human vWF comprises the following:

(SEQ ID NO: 13)
MIPARFAGVLLALALILPGTLCAEGTRGRSSTARCSLFGSDFVNTFDGSM

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNFNIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHFKSFD

NRYFTFSGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDFG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGFMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CRDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNFD

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHDFYCSRLLDLVFLLDGSSRLSEAEFEVLKAFV

VDMMERLRISQKWVRVAVVEYHDGSHAYIGLKDRKRPSELRRIASQVKYA

GSQVASTSEVLKYTLFQIFSKIDRPEASRITLLLMASQEPQRMSRNFVRY

VQGLKKKKVIVIPVGIGPHANLKQIRLIEKQAPENKAFVLSSVDELEQQR

DEIVSYLCDLAPEAPPPTLPPDMAQVTVGPGLLGVSTLGPKRNSMVLDVA

FVLEGSDKIGEADFNRSKEFMEEVIQRMDVGQDSIHVTVLQYSYMVTVEY

PFSEAQSKGDILQRVREIRYQGGNRTNTGLALRYLSDHSFLVSQGDREQA

PNLVYMVTGNPASDEIKRLPGDIQVVPIGVGPNANVQELERIGWPNAPIL

IQDFETLPREAPDLVLQRCCSGEGLQIPTLSPAPDCSQPLDVILLLDGSS

SFPASYFDEMKSFAKAFISKANIGPRLTQVSVLQYGSITTIDVPWNVVPE

KAHLLSLVDVMQREGGPSQIGDALGFAVRYLTSEMHGARPGASKAVVILV

TDVSVDSVDAAADAARSNRVTVFPIGIGDRYDAAQLRILAGPAGDSNVVK

LQRIEDLPTMVTLGNSFLHKLCSGFVRICMDEDGNEKRPGDVWTLPDQCH

TVTCQPDGQTLLKSHRVNCDRGLRPSCPNSQSPVKVEETCGCRWTCPCVC

TGSSTRHIVTFDGQNFKLTGSCSYVLFQNKEQDLEVILHNGACSPGARQG

CMKSIEVKHSALSVELHSDMEVTVNGRLVSVPYVGGNMEVNVYGAIMHEV

RFNHLGHIFTFTPQNNEFQLQLSPKTFASKTYGLCGICDENGANDFMLRD

GTVTTDWKTLVQEWTVQRPGQTCQPILEEQCLVPDSSHCQVLLLPLFAEC

HKVLAPATFYAICQQDSCHQEQVCEVIASYAHLCRTNGVCVDWRTPDFCA

-continued

MSCPPSLVYNHCEHGCPRHCDGNVSSCGDHPSEGCFCPPDKVMLEGSCVP

EEACTQCIGEDGVQHQFLEAWVPDHQPCQICTCLSGRKVNCTTQPCPTAK

APTCGLCEVARLRQNADQCCPEYECVCDPVSCDLPPVPHCERGLQPTLTN

PGECRPNFTCACRKEECKRVSPPSCPPHRLPTLRKTQCCDEYECACNCVN

STVSCPLGYLASTATNDCGCTTTTCLPDKVCVHRSTIYPVGQFWEEGCDV

CTCTDMEDAVMGLRVAQCSQKPCEDSCRSGFTYVLHEGECCGRCLPSACE

VVTGSPRGDSQSSWKSVGSQWASPENPCLINECVRVKEEVFIQQRNVSCP

QLEVPVCPSGFQLSCKTSACCPSCRCERMEACMLNGTVIGPGKTVMIDVC

TTCRCMVQVGVISGFKLECRKTTCNPCPLGYKEENNTGECCGRCLPTACT

IQLRGGQIMTLKRDETLQDGCDTHFCKVNERGEYFWEKRVTGCPPFDEHK

CLAEGGKIMKIPGTCCDTCEEPECNDITARLQYVKVGSCKSEVEVDIHYC

QGKCASKAMYSIDINDVQDQCSCCSPTRTEPMQVALHCTNGSVVYHEVLN

AMECKCSPRKCSK.

In some embodiments, the peptide is from the vWF A3 domain. The vWF A3 domain is derived from the human sequence, residues 1670-1874 (907-1111 of mature vWF) and has the following sequence: CSGEGLQIPTLSPAP-DCSQPLDVILLLDGSSSFPASYFDEMKSFAKAFIS-KANIGPRLTQ VSVLQYGSITTIDVPWNVVPEKAHL-LSLVDVMQREGGPSQIGDALGFAVRYLTSEMH GARPGASKAVVILVTDVSVDSVDAAADAARS-NRVTVFPIGIGDRYDAAQLRILAGPA GDSNVVKLQRIEDLPTMVTLGNSFLHKLCSG (SEQ ID NO:3). Examples of peptides include all or part (i.e., a segment) of SEQ ID NO:13 or all or part of SEQ ID NO:3. In some embodiments, the peptide is from the vWF A1 domain. The vWF A1 domain is derived from the human sequence, residues 1237-1458 (474-695 of mature vWF) and has the following sequence:

(SEQ ID NO: 11)
CQEPGGLVVPPTDAPVSPTTLYVEDISEPPLHDFYCSRLLDLVFLLDGSS

RLSEAEFEVLKAFVVDMMERLRISQKWVRVAVVEYHDGSHAYIGLKDRKR

PSELRRIASQVKYAGSQVASTSEVLKYTLFQIFSKIDRPEASRITLLLMA

SQEPQRMSRNFVRYVQGLKKKKVIVIPVGIGPHANLKQIRLIEKQAPENK

AFVLSSVDELEQQRDEIVSYLC.

In certain embodiments the ECM-affinity peptide comprises all or part of decorin amino acid sequence. Decorin collagen binding domain has the following amino acid sequence: Human decorin GPFQQRGLFDFMLEDEAS-GIGPEVPDDRDFEPSLGPVCP-FRCQCHLRVVQCSDLGLD KVPKDLPPDTTLLD-LQNNKITEIKDGDFKNLKNLHALILVNNK ISKVSPGAFTPLVKL ERLYLSKNQLKEL-PEKMPKTLQELRAHE-NEITKVRKVTFNGLNQMIVIELGTNPLKSS GIEN-GAFQGMKKLSYIRIADTNITSIPQGLP PSLTELHLDGNKISRVDAASLKGLNNLA KLGLSFNSI-SAVDNGSLANTPHLRELHLDNNKLTRVPGG-LAEHKYIQVVYLHNNNIS VVGSSDFCPPGHNTKKA-SYSGVSLFSNPVQYWEIQPSTFRCVYVRSAIQLGNYK (SEQ ID NO:15)

In some embodiments, the ECM-affinity peptide comprises a peptide from PlGF-2. PlGF-2 has the following sequence:

(SEQ ID NO: 4)
MPVMRLFPCFLQLLAGLALPAVPPQQWALSAGNGSSEVEVVPFQEVWGRS

YCRALERLVDVVSEYPSEVEHMFSPSCVSLLRCTGCCGDENLHCVPVETA

NVTMQLLKIRSGDRPSYVELTFSQHVRCECRPLREKMKPERRRPKGRGKR

RREKQRPTDCHLCGDAVPRR.

Exemplary PlGF-2 ECM affinity peptides include:

| | |
|---|---|
| RRRPKGRGKRRREKQRPTDCHLCGDAVPRR; | (SEQ ID NO: 5) |
| RRRPKGRGKRRREKQRPTDCHL; | (SEQ ID NO: 1) |
| RRPKGRGKRRREKQRPTD; | (SEQ ID NO: 6) |
| RRRPKGRGKRRREKQ; | (SEQ ID NO: 7) |
| GKRRREKQ; | (SEQ ID NO: 8) |
| RRRPKGRG; | (SEQ ID NO: 9) |
| and | |
| RRKTKGKRKRSRNSQTEEPHP. | (SEQ ID NO: 10) |

In some embodiments, the ECM-affinity peptide is a peptide from CXCL-12γ. The sequence of CXCL-12γ is the following: CXCL-12γ: KPVSLSYRCPCRFFESH-VARANVKHLKILNTPNCALQIVARLKNNNRQV-CIDPKLKW IQEYLEKALNKGR-REEKVGKKEKIGKKKRQKKRKAAQKRKN (SEQ ID NO:12). An exemplary peptide includes all or part of SEQ ID NO:12 and the following peptide: GRREEKVGKKEKIGKKKRQKKRKAAQKRKN (SEQ ID NO:2).

The ECM-affinity peptide may be a peptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to an ECM or CBD peptide or fragment of the peptides described above. The peptide or polypeptide may have one or more conservative or non-conservative substitutions. Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The polypeptides described herein may include 1, 2, 3, 4, 5, 6, 7, 8, 9, 10, 11, 12, 13, 14, 15, or more (or any derivable range therein) variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of a peptide or polypeptide of the disclosure.

A polypeptide segment or fragment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein of a peptide or polypeptide of the disclosure.

The polypeptides described herein may be of a fixed length of at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more amino acids (or any derivable range therein).

A linker sequence may be included in the cytokine-peptide construction. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate that antibody and the peptide.

The ECM-affinity peptides of the disclosure may have affinity to one or more components of the extracellular matrix such as fibronectin, collagen, (collagen type I, collagen type III, and/or collagen type IV) tenascin C, fibrinogen, and fibrin. In certain aspects the ECM-affinity peptide has an affinity for collagen. And in other aspects the ECM-affinity peptide does not bind fibronectin.

III. Nucleic Acids

In certain embodiments, the current disclosure concerns recombinant polynucleotides encoding the proteins, polypeptides, and peptides of the invention, such as ECM-affinity peptide operatively linked to cytokines or chemokines. Therefore, certain embodiments relate to nucleotides encoding for an ECM-affinity polypeptide and/or an ECM-affinity polypeptide or fragment thereof fused to a cytokine or fragment thereof.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode a polypeptide or peptide of the disclosure. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a polypeptide or peptide of the disclosure.

The nucleic acid segments used in the current disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, the current disclosure provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this disclosure using the methods described herein (e.g., BLAST analysis using standard parameters).

The disclosure also contemplates the use of polynucleotides which are complementary to all the above described polynucleotides.

1. Vectors

Polypeptides of the disclosure may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a polypeptide of the disclosure, the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

2. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK)

(Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon—poly(rI)x/poly(rc) (Tavernier et al., 1983); Adenovirus 5 E2-E1A (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MHC Class I Gene H-2κb—Interferon (Blanar et al., 1989); HSP70-E1A/SV40 Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone α Gene—Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

3. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. RES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

4. Selectable and Screenable Markers

In certain embodiments of the invention, cells containing a nucleic acid construct of the current disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

5. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

6. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Combination Therapy

The compositions and related methods of the present disclosure, particularly administration of and ECM-affinity peptide operatively linked to a cytokine may also be used in combination with the administration of additional therapies such as the additional therapeutics described herein or in combination with other traditional therapeutics known in the art.

The therapeutic compositions and treatments disclosed herein may precede, be co-current with and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a composition disclosed herein is "A" and a second agent, such as an additional agent, chemotherapeutic, or checkpoint inhibitor described herein or known in the art is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In some embodiments, more than one course of therapy may be employed. It is contemplated that multiple courses may be implemented.

1. Chemotherapeutics

The term "chemotherapeutic agent," refers to a therapeutic compound and/or drug which may be used to, among other things, treat cancer. For example, a chemotherapeutic agent may include, but is not limited to, any agent that interferes with cell division, disrupts normal functionality of microtubules, inhibits utilization of a metabolite, substitutes nucleotide analogs into cellular DNA, or inhibits enzymes necessary for DNA replication.

Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some embodiments, cisplatin is a particularly suitable chemotherapeutic agent.

Other suitable chemotherapeutic agents include antimicrotubule agents, e.g., Paclitaxel ("Taxol") and doxorubicin hydrochloride ("doxorubicin").

Nitrogen mustards are another suitable chemotherapeutic agent useful in the methods of the disclosure. A nitrogen mustard may include, but is not limited to, mechlorethamine ($HN_2$), cyclophosphamide and/or ifosfamide, melphalan (L-sarcolysin), and chlorambucil. Cyclophosphamide (CYTOXAN) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

Actual dosage levels of the active ingredients in the methods of this disclosure may be varied so as to obtain an amount of the active ingredient which is effective to achieve the desired therapeutic response for a particular patient, composition and mode of administration, without being toxic to the patient. The selected dosage level will depend upon a variety of factors, including the activity of the chemotherapeutic agent selected, the route of administration, the time of administration, the rate of excretion of the chemotherapeutic agent, the duration of the treatment, other drugs, compounds and/or materials used in combination with the particular chemotherapeutic agent, the age, sex, weight, condition, general health and prior medical history of the patient being treated, and like factors well known in the medical arts.

It is envisioned that combining the effects of chemotherapy and the expression of the therapeutic polypeptide may enhance the antitumor effect of each of these agents if used alone (i.e., if the therapeutic polypeptide is administered directly, and not induced by the presence of the chemotherapeutic agent). A physician having ordinary skill in the art can readily determine and prescribe the effective amount of the construct and the chemotherapeutic agent required. For example, the physician could start doses of the construct and/or chemotherapy at levels lower than that required in order to achieve the desired therapeutic effect and gradually increase the dosage until the desired effect is achieved.

2. Ionizing Radiation

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some embodiments, the amount of ionizing radiation is greater than 20 Gray and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein). In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

In some embodiments, an IR regimen and/or total IR dose is prescribed by a doctor or attending medical professional.

The medical professional may monitor and/or access the progress of the patient throughout the administration of the IR and/or the medical professional may access the patient at the completion of the administration of the prescribed IR dose and prescribe a new dose/regimen of IR based on the assessment.

3. Additional Agents

In some embodiments, the method further comprises administration of an additional agent. In some embodiments, the additional agent is an immunostimulator. The term "immunostimulator" as used herein refers to a compound that can stimulate an immune response in a subject, and may include an adjuvant. In some embodiments, an immunostimulator is an agent that does not constitute a specific antigen, but can boost the strength and longevity of an immune response to an antigen. Such immunostimulators may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherichia coli, Salmonella minnesota, Salmonella typhimurium*, or *Shigella flexneri* or specifically with MPL.® (ASO4), MPL A of above-mentioned bacteria separately, saponins, such as QS-21, Quil-A, ISCOMs, ISCOMATRIX, emulsions such as MF59, Montanide, ISA 51 and ISA 720, AS02 (QS21+squalene+MPL.), liposomes and liposomal formulations such as ASO1, synthesized or specifically prepared microparticles and microcarriers such as bacteria-derived outer membrane vesicles (OMV) of *N. gonorrhea, Chlamydia trachomatis* and others, or chitosan particles, depot-forming agents, such as Pluronic block co-polymers, specifically modified or prepared peptides, such as muramyl dipeptide, aminoalkyl glucosaminide 4-phosphates, such as RC529, or proteins, such as bacterial toxoids or toxin fragments.

In some embodiments, the additional agent comprises an agonist for pattern recognition receptors (PRR), including, but not limited to Toll-Like Receptors (TLRs), specifically TLRs 2, 3, 4, 5, 7, 8, 9 and/or combinations thereof. In some embodiments, additional agents comprise agonists for Toll-Like Receptors 3, agonists for Toll-Like Receptors 7 and 8, or agonists for Toll-Like Receptor 9; preferably the recited immunostimulators comprise imidazoquinolines; such as R848; adenine derivatives, such as those disclosed in U.S. Pat. No. 6,329,381, U.S. Published Patent Application 2010/0075995, or WO 2010/018132; immunostimulatory DNA; or immunostimulatory RNA. In some embodiments, the additional agents also may comprise immunostimulatory RNA molecules, such as but not limited to dsRNA, poly I:C or poly I:poly C12U (available as Ampligen®, both poly I:C and poly I:polyC12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an additional agent may be a TLR-4 agonist, such as bacterial lipopolysaccharide (LPS), VSV-G, and/or HMGB-1. In some embodiments, additional agents may comprise TLR-5 agonists, such as flagellin, or portions or derivatives thereof, including but not limited to those disclosed in U.S. Pat. Nos. 6,130,082, 6,585,980, and 7,192,725.

In some embodiments, additional agents may be proinflammatory stimuli released from necrotic cells (e.g., urate crystals). In some embodiments, additional agents may be activated components of the complement cascade (e.g., CD21, CD35, etc.). In some embodiments, additional agents may be activated components of immune complexes. Additional agents also include complement receptor agonists, such as a molecule that binds to CD21 or CD35. In some embodiments, the complement receptor agonist induces endogenous complement opsonization of the synthetic nanocarrier. In some embodiments, immunostimulators are cytokines, which are small proteins or biological factors (in the range of 5 kDa-20 kDa) that are released by cells and have specific effects on cell-cell interaction, communication and behavior of other cells. In some embodiments, the cytokine receptor agonist is a small molecule, antibody, fusion protein, or aptamer.

In some embodiments, the additional agent is an antibody-drug conjugate. In some embodiments, the antibody-drug conjugate is selected from gemtuzumab ozogamicin, brentuximab vedotin, and trastuzumab emtansine.

In some embodiments, the additional agent is a chimeric antigen receptor (CAR). CARs are artificial T cell receptors which graft a specificity onto an immune effector cell. The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal.

V. Therapeutic Methods

The current methods and compositions relate to methods for treating cancer. In some embodiments, the cancer comprises a solid tumor. In some embodiments, the cancer is non-lymphatic. In some embodiments, the cancer is melanoma or colon cancer.

The compositions of the disclosure may be used for in vivo, in vitro, or ex vivo administration. The route of administration of the composition may be, for example, intratumoral, intracutaneous, subcutaneous, intravenous, intralymphatic, and intraperitoneal administrations. In some embodiments, the administration is intravenous or intratumoral or intralymphatic or peri-tumoral. In some embodiments, the compositions are administered directly into a cancer tissue or a lymph node.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The cancers amenable for treatment include, but are not limited to, tumors of all types, locations, sizes, and characteristics. The methods and compositions of the disclosure are suitable for treating, for example, melanoma, colon cancer, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, specific breast cancers such as ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, male breast cancer, paget's disease of the nipple, phyllodes tumors of the breast, recurrent and/or metastatic breast, cancer, luminal A or B breast cancer, triple-negative/basal-like breast cancer, and HER2-enriched breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

VI. Pharmaceutical Compositions and Methods

In some embodiments, pharmaceutical compositions are administered to a subject. Different aspects involve administering an effective amount of a composition to a subject. In some embodiments, a composition comprising an anti-cancer agent may be administered to the subject or patient to treat cancer or reduce the size of a tumor. Additionally, such compounds can be administered in combination with an additional cancer therapy.

Compositions can be formulated for parenteral administration, e.g., formulated for injection via the intravenous, transcatheter injection, intraarterial injection, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. The preparation of such formulations will be known to those of skill in the art in light of the present disclosure. Other routes of administration include intratumoral, peri-tumoral, intralymphatic, injection into cancer tissue, and injection into lymph nodes. In some embodiments, the administration is systemic.

Other routes of administration are also contemplated. For example, the constructs and agents may be administered in association with a carrier. In some embodiments, the carrier is a nanoparticle or microparticle. In some embodiments, the nanoparticle or microparticle is a tumor directed nanoparticle or microparticle. For example, the carrier may further comprise a targeting moiety that directs the carrier to the tumor. The targeting moiety may be a binding agent (e.g., antibody, including scFv, etc. or other antigen binding agent) that specifically recognizes tumor cells. In some embodiments, the construct is enclosed within the carrier. In some embodiments, the construct is covalently or non-covalently attached to the surface of the carrier. In some embodiments, the carrier is a liposome.

Particles can have a structure of variable dimension and known variously as a microsphere, microparticle, nanoparticle, nanosphere, or liposome. Such particulate formulations can be formed by covalent or non-covalent coupling of the construct to the particle.

By "particle," "microparticle," "bead," "microsphere," and grammatical equivalents herein is meant small discrete particles that are administrable to a subject. In certain embodiments, the particles are substantially spherical in shape. The term "substantially spherical," as used herein, means that the shape of the particles does not deviate from a sphere by more than about 10%.

The particles typically consist of a substantially spherical core and optionally one or more layers. The core may vary in size and composition. In addition to the core, the particle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired particle diameter), these layers typically being applied on the outer surface of the particle.

The compositions of the core and layers may vary. Suitable materials for the particles or the core include, but are not limited to polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference in its entirety.

As previously stated, the particle may, in addition to the core, include one or more layers. The purposes for including layers in the microparticle may vary. Alternatively, the surface of the particle may be functionalized directly. A layer may provide suitable surfaces for attaching chemical functionalities for chemical binding or coupling sites.

Layers can be produced on the microparticles in a variety of ways known to those skilled in the art. Examples include sol-gel chemistry techniques such as described in Iler (1979); Brinker and Scherer (1990). Additional approaches to producing layers on particles include surface chemistry and encapsulation techniques such as described in Partch and Brown (1998); Pekarek et al. (1994); Hanprasopwattana (1996); Davies (1998); and references therein. Vapor deposition techniques may also be used; see for example Golman and Shinohara (2000); and U.S. Pat. No. 6,387,498. Still other approaches include layer-by-layer self-assembly techniques such as described in Sukhorukov et al. (1998); Caruso et al. (1998); Caruso et al. (1999); U.S. Pat. No. 6,103,379 and references cited therein.

Particles may be formed by contacting an aqueous phase containing the construct and a polymer and a nonaqueous phase followed by evaporation of the nonaqueous phase to cause the coalescence of particles from the aqueous phase as taught in U.S. Pat. No. 4,589,330 or 4,818,542. Preferred polymers for such preparations are natural or synthetic copolymers or polymers selected from the group consisting of gleatin agar, starch, arabinogalactan, albumin, collagen, polyglycolic acid, polylactic acid, glycolide-L(−) lactide poly(episilon-caprolactone, poly(epsilon-caprolactone-CO-lactic acid), poly(epsilon-caprolactone-CO-glycolic acid), poly($\beta$-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(esterurea), poly(L-phenylalanine/ethylene glycol/1,6-diisocyanatohexane) and poly(methyl methacrylate). Particularly preferred polymers are polyesters, such as polyglycolic acid, polylactic acid, glycolide-L(−) lactide poly(episilon-caprolactone, poly(epsilon-caprolactone-CO-lactic acid), and poly(epsilon-caprolactone-CO-glycolic acid. Solvents useful for dissolving the polymer include: water, hexafluoroisopropanol, methylenechloride, tetrahydrofuran, hexane, benzene, or hexafluoroacetone sesquihydrate.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or g/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms of an infection have disappeared or been reduced.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments Example 1

Engineered Collagen-Binding Interleukin-2 Shows Enhanced Antitumor Efficacy and Reduced Adverse Events Cytokine immunotherapy with interleukin-2 (IL-2) exhibits considerable antitumor activity in animal models and the clinic. Here, the inventors engineered a fusion protein of IL-2 to a collagen-binding domain (CBD) from the von Willebrand Factor (vWF) A3 domain; the fusion protein can be administered intravenously and targets the tumor microenvironment via its leaky vasculature, which allows access of proteins in the blood to the tumor stroma. Here, the inventors show tumor tissue localization of CBD protein. CBD-IL-2 showed decreased serum inflammatory cytokine concentrations in blood serum after injection. CBD-IL-2 significantly delayed tumor growth compared to wild-type IL-2 in murine melanoma and colon cancer models. This simple and translatable approach of an engineered collagen-binding cytokine presents a novel approach to cancer immunotherapeutics.

A. Results

CBD-fused IL-2 bind to collagen and its receptor. The inventors first examined the capacities of CBD-fused IL-2 recombinant protein (CBD-IL-2), to bind collagen in vitro. CBD-fused IL-2 was designed and expressed recombinantly (FIG. 1A). SDS-PAGE revealed that the molecular weight of IL-2 was increased by CBD fusion (FIG. 1). CBD-IL-2 bound to types I and III collagens with strong binding affinities (nM range dissociation constant ($K_D$) values) (FIG. 1C-1D). In comparison, wild-type IL-2 did not bind to these collagens. Importantly, CBD-IL-2 bound to IL-2Rα with similar $K_D$ values as wild-type IL-2. Also, CBD-IL-2 induced cell proliferation of CTLL-2 cell line, which is a IL-2 dependent NK cell line, with similar effect as its wild-type form (FIG. 1E). Taken together, these data showed that CBD-IL-2 binds to collagens without impairment of the target binding capacities of either the CBD or the IL-2 domains.

CBD protein localized in the tumor. The inventors performed an in vivo bio-distribution analysis to determine if CBD localizes in the tumor microenvironment after intravenous (i.v.) injection through binding to endogenous collagen. MMTV-PyMT breast cancer was inoculated in the FVB mouse. When the tumor volume reached 500 mm³, DyLight 800 labeled CBD protein was injected. Two days after injection, the tumor and organs including heart, lung, kidney, liver, spleen, and stomach were harvested. Fluorescent detection revealed that CBD protein preferentially localized in the tumor (FIG. 2A).

CBD fusion decreases treatment-related adverse events. Since CBD protein localized within the tumor, it was hypothesized that the side-effects of CBD-IL-2 after injection would be lower compared to IL-2, due to competition by the tumor and corresponding lowering of systemic exposure. CBD-IL-2 and IL-2 were administrated 4 days after B16F10 melanoma inoculation, then cytokine concentrations in the serum were examined 24 hr following injection. Wild-type IL-2 administration increased IFNγ concentrations in serum, whereas CBD-IL-2 did not (FIG. 2B). This result indicates that the CBD fusion may decrease the systemic toxicity of IL-2.

CBD-IL-2 significantly suppresses growth of B16F10 and CT-26 tumors compared to IL-2. The inventors examined the antitumor efficacy of CBD-IL-2 using B16F10 melanoma and CT26 colon carcinoma. Four days after B16F10 cell inoculation, 6 g IL-2 or 12 µg (equivalent molar) CBD-IL-2 were injected. At this dose, wild-type IL-2 treatment did not show a clear antitumor effect, while CBD-IL-2 treatment induced smaller tumor sizes (FIG. 3A). Five days after CT26 cell inoculation, 6 µg IL-2 or 12 µg (equivalent molar) CBD-IL-2 were injected. CBD-IL-2 again slowed the tumor growth of CT26, whereas IL-2 did not (FIG. 3B). These set of data indicated that CBD-IL-2 therapy has superior antitumor effects compared to its wild-type form.

The strategy of localized cancer therapy can be classified as active targeting and passive targeting (Danhier et al., *J Control Release* 148:135-46, 2010). Antibody-drug conjugates are an example of active targeting. Targeting is based on the attachment of drugs to specific ligands (e.g., antibodies) that are tumor or tumor cell-specific (Chari et al., *Angew Chem Int Ed Engl* 53:3796-827, 2014), facilitating delivery of cancer drugs specifically to tumor cell surfaces. An example of passive targeting is a drug embedded in a nanoparticle carrier. Nanoparticles are expected to have a prolonged half-life in the blood, leading to accumulation in tumor where the vasculature is leaky via the enhanced permeability and retention (EPR) effect (Maeda et al., *J Control Release* 65:271-84, 2000; Swartz and Fleury, *Annu Rev Biomed Eng* 9:229-56, 2007). Therefore, passive targeting is based on the longevity of the pharmaceutical carrier in the blood and its accumulation in pathological sites with irregular vasculature and thus enhanced accumulation.

The collagen binding domain (CBD)-based drug targeting approach proposed in this application is similar to active targeting, but also exploits the leaky structure of tumor vessels (Nagy et al., *British journal of cancer* 100:865, 2009; in the normal tissue, very little collagen is exposed (Dubois et al., *Blood* 107:3902-06, 2006; Bergmeier and Hynes, *Cold Spring Harb Perspect Biol* 4:a005132, 2012), but in the tumor, with its leaky vasculature, collagen is indeed exposed (Liang et al., *Journal of controlled release* 209:101-09, 2015; Liang et al., *Sci Rep* 6:18205, 2016; Yasunaga et al., *Bioconjugate chemistry* 22:1776-83, 2011; Xu et al., *The Journal of cell biology* 154:1069-80, 2001; Swartz and Lund, *Nat Rev Cancer* 12:210-19, 2012). Thus, the CBD-fusions are tumor microenvironment-specific, yet not via targeting a molecule that is specifically located in the tumor (indeed, collagen is nearly everywhere), but rather that is only exposed via the tumor's leaky vasculature. Also, this can be a hybrid approach utilizing both advantages.

The vWF A3 domain and collagen association is an initiator of the thrombosis cascade, thus this binding commonly occurs in human body (Shahidi, *Advances in experimental medicine and biology* 906:285-306, 2017). In this study, the inventors have developed cancer immunotherapy, targeting cancer microenvironment using the vWF A3 domain as CBD.

Previously, a tumor matrix targeting approach that fuses a single chain antibody fragment against a tumor-specific fibronectin domain and cytokines has been tested in animal models and clinical trials (Carnemolla et al., *Blood* 99:1659-65, 2002; Eigentler et al., *Clinical cancer research* 17:7732-42, 2011; Ferrari et al., *Drug Discov Today* 21:172-79, 2016). The fibronectin extra-domain A (EDA) and EDB domains are expressed in tumor but not in the normal tissue (Rybak et al., *Cancer Res* 67:10948-957, 2007; Villa et al., *Int J Cancer* 122:2405-13, 2008). Single chain antibodies against the fibronectin EDA and EDB domains localize within tumor after systemic injection through this tumor-specific location of the EDA and EDB targets (Carnemolla et al., *Blood* 99:1659-65, 2002; Rybak et al., *Cancer Res*

67:10948-957, 2007). A fusion protein of the single chain antibody and IL-2 showed enhanced antitumor efficacy compared to normal IL-2 in a mouse model (Carnemolla et al., *Blood* 99:1659-65, 2002).

Collagen is the most abundant protein in the human body (Addi et al., *Tissue Engineering Part B: Reviews*, 2016; Di Lullo et al., *Journal of Biological Chemistry* 277:4223-31, 2002, especially tumors contain more collagen than normal tissue (Zhou et al., *J Cancer* 8:1466-76, 2017; Provenzano et al., *BMC Med* 6:11, 2008). Thus, in the CBD approach, the target protein should be more abundant compared to the EDA and EDB domains of fibronectin. Liang et al. have reported that fusing a collagen-binding short peptide (TKKLRT (SEQ ID NO:14)) with an anti-epithelial growth factor receptor (EGFR) Fab or single-chain antibody improves tumor tissue localization of the antibody compared to naive anti-EGFR Fab or single-chain antibody when injected i.p. (Liang et al., *Journal of controlled release* 209:101-09, 2015; Liang et al., *Sci Rep* 6:18205, 2016). This TKKLRT peptide was discovered by phage display, with reported $K_D$ values or the half-maximal effective concentration (EC50) toward collagen type I being 0.5-6 μM (Addi et al., *Tissue Engineering Part B: Reviews*, 2016). Also, TKKLRT-anti-EGFR Fab exhibited enhanced anti-tumor efficacy compared to naive anti-EGFR antibody. With EGFR, this mechanism is mediated by direct inhibition of proliferation of cancer cells, but not immuno-modulation (Martinelli et al., *Clin Exp Immunol* 158:1-9, 2009). The inventors' approach uses CBD proteins that are naturally existing in the body and are thus not immunogenic. CBD protein such as the vWF A3 protein binds to multiple collagen types unlike more specific ligand such as peptides, antibodies or antibody fragments. Also, the vWF A3 domain protein has high affinity (nM range $K_D$) towards multiple types of collagens (Addi et al., *Tissue Engineering Part B: Reviews*, 2016). Thus, the approach is novel both in the methodology (high affinity protein domains derived from protein that naturally exist in the body, versus low affinity peptide domains) and in the biological approach (targeting the protein that is abundant in the body but that is only exposed in the tumors via its leaky vasculature).

The inventors have shown that the CBD-IL-2 fusion did not increase IFNγ concentrations in blood serum whereas the wild-type IL-2 did. Considering CBD-mediated tumor targeting, this could be because of the sequestration of IL-2 within the tumor by competition. CBD-IL-2 localizes within the tumor and thus reduces the concentration in the blood circulation, thus potentially maintaining systemic immune homeostasis by avoiding systemic immune cell activation. CBD-fusion may even allow decreases in the administered dose, because the inventors observed tumor growth delay at low dosages where the unmodified IL-2 had no effect. These data are encouraging with regard to treatment of patients who have discontinued cancer immunotherapy due to adverse events.

CBD-fused IL-2 demonstrated higher antitumor effects compared to the wild-type form in two tumor models. These data suggest that the collagen targeting approach by the vWF A3 domain is generally applicable to multiple tumors. IL-2 is known to have an antitumor effect through amplifying $CD8^+$ T cells and NK cells. Thus, with tumor targeting, CBD-IL-2 might more efficiently increase the numbers of tumor-infiltrating T cells and NK cells compared to its unmodified form.

Since checkpoint inhibitors are approved for melanoma patients, and B16F10 melanoma is checkpoint-unresponsive model, the inventors were interested in whether CBD-IL-12 can increase the antitumor efficacy of α-PD-L1 antibody. Mice were treated in three cycles, every 10 days starting on day 7. IL-12 and α-PD-L1 injections were performed on consecutive days with IL-12 being administered first. α-PD-L1 alone had little effect on tumor growth (FIG. 4A). Although both IL-12 and CBD-IL-12 significantly reduced tumor growth in combination with α-PD-L1 compared to either PBS-treated or antibody-treated groups, CBD-IL-12 did so more effectively. CBD-IL-12-treated mice had significantly prolonged overall survival (FIG. 4B), with 1 out of 12 mice completely curing the disease.

To investigate whether CBD-IL-12 synergizes with checkpoint-blocking antibodies, CBD-IL-12 monotherapy was compared to CBD-IL-12 in combination with α-PD-L1 alone or α-PD-1+α-CTLA-4. Mice failed to respond to either α-PD-L1 or α-PD-1+α-CTLA-4, whereas robust regressions in tumor sizes were observed for CBD-IL-12 alone and for CBD-IL-12 in combination with checkpoint-blocking antibodies in the early time points (FIG. 5A). However, overall survival was significantly improved when mice received CBD-IL-12 in combination with α-PD-1+α-CTLA-4, yielding 6 out of 11 complete responders (FIG. 5B). 4 out of 10 mice completely cured the disease when CBD-IL-12 was combined with α-PD-L1, whereas only 1 out of 10 mice was cured in CBD-IL-12 monotherapy group.

In conclusion, the inventors found that the antitumor effect of IL-2 was enhanced when a collagen-binding property was installed. Fusion of the vWF A3 CBD enhanced IL-2. CBD-IL-2 significantly delayed tumor growth in multiple tumor models. This simple approach of an engineered collagen-binding cytokine immunotherapy may hold potential for clinical translation as a targeted cancer therapeutic.

B. Materials and Methods

Production and purification of recombinant vWF A3 domain and mouse IL-2 protein. Protein production and purification were performed as described previously (Martino et al., *Science* 343:885-88, 2014). The sequence encoding for the human vWF A3 domain residues Cys1670-Gly1874 (907-1111 of mature vWF), mouse IL-2, the human vWF A3 domain and mouse IL-2 fusion protein was synthesized and subcloned into the mammalian expression vector pcDNA3.1(+) by Genscript. A sequence encoding for 6 His was added at the N-terminus for further purification of the recombinant protein. Suspension-adapted HEK-293F cells were routinely maintained in serum-free FreeStyle 293 Expression Medium (Gibco). On the day of transfection, cells were inoculated into fresh medium at a density of $1 \times 10^6$ cells/ml. Two μg/ml plasmid DNA, 2 μg/ml linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% $CO_2$. Six days after transfection, the cell culture medium was collected by centrifugation and filtered through a 0.22 μm filter. Culture media was loaded into a HisTrap HP 5 ml column (GE Healthcare), using an ÄKTA pure 25 (GE Healthcare). After washing of the column with wash buffer (20 mM imidazole, 20 mM $NaH_2PO_4$, 0.5 M NaCl, pH 7.4), protein was eluted with a gradient of 500 mM imidazole (in 20 mM $NaH_2PO_4$, 0.5 M NaCl, pH 7.4). The elution solution was further purified with size exclusion chromatography using a HiLoad Superdex 200PG column (GE healthcare). All purification steps were carried out at 4° C. The expression of laminin LG domain was determined by western blotting using anti-His tag antibody (BioLegend) and the proteins were verified as >90% pure b SDS-PAGE.

vWF A3 domain protein-
(SEQ ID NO: 34)
CSQPLDVILLLDGSSSFPASYFDEMKSFAKAFISKANIGPRLTQVSVLQY

GSITTIDVPWNVVPEKAHLLSLVDVMQREGGPSQIGDALGFAVRYLTSEM

HGARPGASKAVVILVTDVSVDSVDAAADAARSNRVTVFPIGIGDRYDAAQ

LRILAGPAGDSNVVKLQRIEDLPTMVTLGNSFLHKLCSGFVRICTGHHHH

HH

Mouse IL-2-
(SEQ ID NO: 35)
PTSSSTSSSTAEAQQQQQQQQQQQQHLEQLLMDLQELLSRMENYRNLKLP

RMLTFKFYLPKQATELKDLQCLEDELGPLRHVLDLTQSKSFQLEDAENFI

SNIRVTVVKLKGSDNTFECQFDDESATVVDFLRRWIAFCQSIISTSPQHH

HHHH

The vWF A3 domain and mouse IL-2 fusion protein-
(SEQ ID NO: 36)
CSQPLDVILLLDGSSSFPASYFDEMKSFAKAFISKANIGPRLTQVSVLQY

GSITTIDVPWNVVPEKAHLLSLVDVMQREGGPSQIGDALGFAVRYLTSEM

HGARPGASKAVVILVTDVSVDSVDAAADAARSNRVTVFPIGIGDRYDAAQ

LRILAGPAGDSNVVKLQRIEDLPTMVTLGNSFLHKLCSGFVRIGGGSGGG

SPTSSSTSSSTAEAQQQQQQQQQQQQHLEQLLMDLQELLSRMENYRNLKL

PRMLTFKFYLPKQATELKDLQCLEDELGPLRHVLDLTQSKSFQLEDAENF

ISNIRVTVVKLKGSDNTFECQFDDESATVVDFLRRWIAFCQSIISTSPQH

HHHHH

Sodium dodecyl sulfate acrylamide gel electrophoresis (SDS-PAGE). The measurement is performed as described previously (Ishihara et al., Sci Transl Med 9:doi:10.1126/scitranslmed.aan401, 2017). SDS-PAGE was performed on 4-20% gradient gels (Bio-Rad). After electrophoresis, gels were stained with SimplyBlue SafeStain (Thermo Fisher Scientific) according to manufacturer's instruction. Gel images were acquired with the ChemiDoc XRS+ system (Bio-Rad).

Detection of CBD-IL-2 binding to collagen proteins. The measurement is performed as described previously (Ishihara et al., Sci Transl Med 9:doi:10.1126/scitranslmed.aan401, 2017). 96-well ELISA plates (Greiner Bio One) were coated with 10 µg/mL collagen I (EMD Millipore), collagen III (EMD Millipore), or 1 µg/mL recombinant mouse IL-2Rα (SinoBiological) in PBS for 1 h at 37° C., followed by blocking with 2% BSA in PBS with 0.05% Tween 20 (PBS-T) for 1 hr at RT. Then, wells were washed with PBS-T and further incubated with 10 µg/mL CBD- or unmodified-IL-2 for 1 hr at RT. After 3 washes with PBS-T, wells were incubated for 1 hr at RT with HRP-conjugated antibody against rat IgG (Jackson ImmunoResearch). After washes, bound CBD-TL2 and IL-2 were detected with tetramethylbenzidine substrate by measurement of the absorbance at 450 nm with subtraction of 570 nm. The apparent dissociation constant ($K_D$) values were obtained by nonlinear regression analysis in Prism software (v7, GraphPad Software) assuming one-site specific binding.

Proliferation assay. CTLL-2 cells (ATCC) were cultured in RPMI 1640 (ATCC), supplemented with heat inactivated fetal bovine serum, L-glutamine, sodium pyruvate, and penicillin-streptomycin, and recombinant mouse IL-2 (Peprotech). Cells were passaged twice a week to a density of 10,000 cells/mL. For proliferation assays, cells were seeded at 100,000 cells/mL, and mouse IL-2 and CBD-IL-2 were added at indicated concentrations on an IL-2 basis, in a final volume of 100 µL. Cells were grown for 48 hrs. Proliferation was conducted by using CyQUANT Cell Proliferation Assay Kit (Invitrogen) according to manufacturer's instructions. Fluorescence was measured using a BioTek Cytation 3 Cell Imaging Multi-Mode Reader (fisher scientific). A dose response curve was fit via nonlinear regression using GraphPad Prism 7 software (GraphPad).

Mice and cell lines. The mice and cell lines were prepared as described previously (Ishihara et al., Sci Transl Med 9:doi:10.1126/scitranslmed.aan0401, 2017). C57BL/6, FVB, and Balb/c mice, age 8 to 12 weeks, were obtained from the Jackson laboratories. Experiments were performed with approval from the Institutional Animal Care and Use Committee of the University of Chicago. B16F10 cells and CT26 cells were obtained from the American Type Culture Collection and cultured according to the instructions. All cell lines were checked for *mycoplasma* contamination by a pathogen test IMPACT I (IDEXX BioResearch).

In vivo bio-distribution study. The vWF A3 domain protein was fluorescently labeled using DyLight 800 NHS ester (Thermo Fisher) and unreacted dye was removed by a Zebaspin spin column (Thermo Fisher) according to the manufacture's instruction. A total of $8\times10^5$ MMTV-PyMT cells re-suspended in 50 µL of PBS were injected subcutaneously into the mammary fat pad on the right side of each FVB mouse. When tumor reached 500 mm$^3$, 50 µg of DyLight 800 labeled CBD was injected i.v. Mice organs were extracted and imaged 48 hours after injection with the Xenogen IVIS Imaging System 100 (Xenogen) under the following conditions: f/stop: 2; optical filter excitation 740 nm; excitation 800 nm; exposure time: 5 sec; small binning.

Serum cytokine concentration analysis. The measurement is performed as described previously (Ishihara et al., Sci Transl Med 9:doi:10.1126/scitranslmed.aan0401, 2017). $5\times10^5$ B16F10 melanoma cells were injected intradermally on left side of the back of each 12 week old C57BL/6 mouse (The Jackson Laboratory). After 4 days, mice received 6 µg of IL-2 and 12 µg of CBD-IL-2. On day 5, blood samples were collected in tubes, followed by overnight incubation at 4° C. Cytokine concentrations in serum were measured by Ready-SET-Go!ELISA kits (eBioscience) according to the manufacture's protocol.

Anti-tumor efficacy of CBD-IL-2 on B16F10 tumor. The measurement is performed as described previously (Ishihara et al., Sci Transl Med 9:doi:10.1126/scitranslmed.aan0401, 2017). A total of $5\times10^5$ B16F10 cells re-suspended in 50 µL of PBS were inoculated intradermally on the left side of the back of each C57BL/6 mouse. After 4 days, mice were injected with IL-2 (6 µg) or CBD-IL-2 (12 µg) i.v. Tumors were measured with a digital caliper starting 4 days after tumor inoculation, and volumes were calculated as ellipsoids, where V=4/3×3.14×depth/2×width/2×height/2. Mice were sacrificed at the point when either tumor volume had reached over 500 mm$^3$.

Antitumor efficacy of CBD-IL-2 on CT26 tumor. A total of $5\times10^5$ CT26 cells re-suspended in 50 µL of PBS were inoculated intradermally on the left side of the back of each Balb/c mouse. After 5 days, mice were injected i.v. with IL-2 (6 µg) or CBD-IL-2 (12 µg). Tumors were measured with a digital caliper starting 5 days after tumor inoculation as described above. Mice were sacrificed at the point when either tumor volume had reached over 500 mm$^3$.

Statistical analysis. All experiments are replicated at least twice. For the animal study, mice were randomized into treatment groups within a cage immediately before IL-2 and CBD-IL-2 injection and treated in the same way. The survival endpoint was reached when the tumor size became over 500 mm$^3$ for B16F10 and CT26 tumors. The n values used to calculate statistics are indicated in figure legends. Statistically significant differences between experimental groups were determined using Prism software (v7, GraphPad). Where one-way ANOVA followed by Tukey's HSD post hoc test was used, variance between groups was found to be similar by Brown-Forsythe test. For single comparisons, a two-tailed Student's t-test was used. Survival curves were analyzed by using the log-rank (Mantel-Cox) test. The n values used to calculate statistics are indicated in figure legends. The symbols * and ** indicate P values less than 0.05 and 0.01, respectively; N.S., not significant.

Additional cytokines to be tested. Other than IL-2, a number of cytokines including chemokines have been shown to have anti-tumor efficacy and are currently being tested in the clinical trials (Tokunaga et al., *Cancer treatment reviews* 63:40-47, 2017; Lin et al., *Cancers (Basel)* 6:1098-110, 2014; Akdis et al., *The Journal of allergy and clinical immunology* 127:701-21, 2011; Waldmann, *Nature reviews. Immunology* 6:595-601, 2006). The inventors expect that addition of CBD sequence in the N- or C-terminus of the cytokine enables efficient tumor targeting, as the inventors have shown with CBD-IL-2 in the previous part. The inventors will test cytokines that multiply T cells: IFNα, IFNβ, IL-15, IL-15 super agonist (fusion protein of IL-15 and IL-15Rα), and IL-21, or NK cells: IL-12 (Akdis et al., *The Journal of allergy and clinical immunology* 127:701-21, 2011; Waldmann, *Nature reviews. Immunology* 6:595-601, 2006). The inventors will also test VEGF-C, which is a cytokine that induces lymphangiogenesis, leading to increased immune cells infiltration (Fankhauser et al., *Sci Transl Med* 9:doi:10.1126/scitranslmed.aal4712, 2017; Lund et al., *Cell Rep* 1:191-99, 2012). Similarly, the inventors will test chemokines (e.g., XCL1, CCL4, CCL21, CXCL9, and CXCL10) that reportedly recruit anti-tumor immune cells into tumor microenvironment (Tokunaga et al., *Cancer treatment reviews* 63:40-47, 2017; Lin et al., *Cancers (Basel)* 6:1098-110, 2014).

Additional CBD to be tested. Other than the vWF A3 domain, protein (the vWF A1 domain (SEQ ID NO:11) and decorin (SEQ ID NO:15)), and a peptide (TKKLRT (SEQ ID NO:14)) have been shown to bind to collagen (Addi et al., *Tissue Engineering Part B: Reviews*, 2016). Because the vWF A1 domain and decorin are similar molecular weight proteins as the vWF A3 domain protein and show high binding affinity similar to the vWF A3 domain, it is expect that addition of these the vWF A1 domain and decorin sequence in the N- or C-terminus of the cytokines also target tumor microenvironment, similarly to that shown with CBD-IL-2. However, it is anticipated that addition of TKKLRT sequence in the N- or C-terminus of the cytokine would not show tumor microenvironment targeting capacity due to its small molecular weight and low collagen affinity (µM range of $K_D$)(Addi et al., *Tissue Engineering Part B: Reviews*, 2016). Thus, addition of TKKLRT sequence would not alter the antitumor activity of the cytokine.

Production and purification of CBD-fused cytokine. As described in the CBD-IL-2 part above, the sequence encoding for CBD will be cloned and subcloned into the mammalian expression vector pcDNA3.1(+). Histidine-tag will be added on the N- or C-terminus of the protein sequence. The CBD-fused cytokine recombinant protein will be expressed in suspension-adapted HEK-293F cells in serum-free FreeStyle 293 Expression Medium. The produced recombinant protein will be purified using a histidine-tagged protein purification column and size-exclusion.

Tumor inoculation and immunomodulatory antibody treatment through intravenous injection. Tumor cells (e.g., B16F10) will be inoculated intradermally (id). After tumors become visible, mice will receive intravenous injections of CBD- or wild-type-cytokines through the tail vein. Tumor size will be monitored until it reaches the euthanasian criteria. Here, the inventors expect that iv injection of CBD-cytokines will show enhanced tumor tissue localization and retention through binding to collagen in the tumor microenvironment. Through a similar mechanism to what is described above in IL-2 part, CBD-fusion will increase cytokine concentration within the tumor microenvironment, leading to reduced incidents of side-effects and enhance anti-tumor efficacy of cytokine/chemokine.

Example 2

Recruitment of CD103$^+$ DCS Via Tumor-Targeted Chemokine Delivery Enhances Efficacy of Checkpoint Inhibitor Immunotherapy A. Results CBD-CCL4 recombinant protein was produced using mammalian protein expression techniques similar to previous reports (Ishihara et al., *Sci Transl Med*, 2019). Following production and purification using affinity and size-exclusion chromatography, CBD-CCL4 was evaluated using SDS-polyacrylamide gel electrophoresis (SDS-PAGE). Fusion with CBD increased the molecular size of CCL4 by approximately 20 kDa compared to native (WT) CCL4, consistent with the size of the A3 domain of vWF (FIG. 6A). Using surface plasmon resonance (SPR), the affinity for collagen I and collagen III was calculated as 33.4 nM and 14.5 nM, respectively (FIG. 6B, 6C). These results agree with previous collagen affinity for CBD-modified immunotherapies (Ishihara et al., *Sci Transl Med*, 2019). Next, the activity of WT CCL4 and CBD-CCL4 was evaluated using a calcium flux assay, as CCL4 signals through the G protein-coupled receptor (GPCR) CCR5 (Alkhatib, *Curr Opin HIV AIDS* 4, 96-103, 2009), leading to calcium release upon activation (FIG. 6D). Both native CCL4 and CBD-CCL4 exhibited similar GPCR activation levels, highlighting that CBD-fusion did not alter its ability to signal through CCR5.

Next, the blood plasma pharmacokinetics of WT CCL4 and CBD-CCL4 were evaluated following intravenous administration in B16F10 tumor-bearing mice. Interestingly, CBD-CCL4 exhibited delayed clearance compared to WT CCL4 (FIG. 7A). The increase in molecular size of the molecule may slow its clearance from blood; this could have important implications for tumor-targeting, as enhanced blood circulation time is often attractive for enhancing delivery of macromolecules to tumors (Pisal et al., *J Pharm Sci* 99, 2557-75, 2010). Furthermore, enhanced circulation time may allow for additional opportunities to bind to exposed collagen in the leaky tumor microvasculature (Ruoslahti et al., *J Cell Biol* 188, 759-68, 2010). To confirm that CBD-fusion enhanced tumor delivery of CCL4, biodistribution studies were performed in EMT6 breast cancer-bearing mice following intravenous administration. Importantly, CBD-CCL4 fusion exhibited a 2.4-fold increase in tumor accumulation 30 min following administration (FIG. 7B). These data demonstrate the effective delivery of CBD-CCL4 to the tumor microenvironment.

Next, the inventors investigated whether it could enhance tumor immune infiltration, a key factor driving successful responses to CPI therapy. For all subsequent experiments CCL4 chemokine therapy was co-administered with CPI therapy comprising of αCTLA4+αPD-L1, a combination treatment strategy for advanced melanoma and non-small cell lung cancer in the clinic (Chae et al., *J Immunother Cancer* 6, 39, 2018; Gong et al., *J Immunother Cancer* 6, 8, 2018). CPI therapy alone was included for baseline comparison. Combination CCL4 and CPI therapy were evaluated in B16F10 melanoma, a tumor model shown to be a poor responder to CPI therapy alone (Lechner et al., *J Immunother* 36, 477-89, 2013). As shown in FIG. 8A, only the combination of CBD-CCL4 (administered via i.v. injection) and CPI therapy (administered via intraperatonieal (i.p.) injection) showed a significant reduction in tumor growth rate. WT CCL4, given in combination with CPI therapy, did not show any reduction in tumor growth rates. These results confirm that targeted chemokine delivery is required to elicit a therapeutic benefit from CCL4.

Because a significant slowing of tumor growth was observed, it was hypothesized that an increase in CD103$^+$ DC recruitment to the tumor may be contributing to the anti-tumor immune response. 6 days following administration of the treatment regime, mice were sacrificed, and tumors were harvested and processed for flow cytometry analysis of the immune cell infiltrates in the tumor. Compared to CPI therapy alone and CPI given in combination with WT CCL4, CPI therapy given with CBD-CCL4 significantly increased the number of CD45$^+$ immune cells (FIG. 8B) in the tumor, indicating a more inflamed microenvironment. Looking specifically at the immune cell composition, it was observed that the CPI therapy given with CBD-CCL4 led to the highest infiltration of key drivers of anti-tumor immune responses, including CD103$^+$ DCs (FIG. 8C), CD8$^+$ T cells (FIG. 8D), natural killer (NK) cells (FIG. 8E), as well as total CD11c$^+$ DCs (FIG. 8F). CD4$^+$ T cells was also significantly improved relative to combination of CPI therapy and WT CCL4 (FIG. 8G). Importantly, no increase in the regulatory T cell (Treg) fraction of CD4$^+$ T cells was observed (FIG. 8H), indicating that increases in tumor inflammation did not also significantly alter Treg recruitment.

Correlation analysis was performed between the immune cell infiltration and tumor growth to highlight the contribution of each cell population to driving anti-tumor immunity. Correlation between tumor volume and cell infiltration was strongest for CD103$^+$ DCs and CD8$^+$ T cells (FIG. 9A, 9B), with the greatest cell infiltrate numbers leading to the smallest tumor volumes. As expected, a significant positive correlation between CD103$^+$ DCs and CD8$^+$ T cells was observed (FIG. 9C), as it has previously been shown that CD103$^+$ DCs secrete chemokines necessary for T cell infiltration into the tumor (Spranger et al., *Cancer Cell* 31, 711-23 e714, 2017). Lesser trends were observed between NK cells and CD11c$^+$ DCs (FIG. 9D, 9E), highlighting that these cell types are important for tumor growth control, albeit less so than CD103$^+$ DCs and CD8$^+$ T cells. Furthermore, a less striking correlation was observed between total CD45$^+$ immune cells and tumor growth (FIG. 9F), indicating that total immune infiltration alone is not strong enough to drive anti-tumor immunity. Rather, the specific cell types driving anti-tumor immunity must be recruited to maximize therapeutic effect.

To follow up on the immune infiltrate responses observed in B16F10 melanoma, similar analysis were performed in the EMT6 breast cancer model. The EMT6 model, while moderately responsive to CPI therapy, is categorized as an immune excluded tumor model (Mariathasan et al., *Nature* 554, 544-48, 2018). Therefore, it was hypothesized that tumor-targeted CCL4 delivery may further enhance CD103$^+$ DC recruitment and further improve efficacy of CPI therapy. Similar to the results observed in B16F10 melanoma, only the combination of CPI therapy and CBD-CCL4 exhibited a significant reduction in tumor growth (FIG. 10A). WT CCL4 given in combination with CPI therapy showed no significant improvement relative to CPI therapy alone. Detailed analysis of the immune cell infiltrates using flow cytometry found that CBD-CCL4 in combination with CPI therapy exhibited a significant increase in the total number of CD45$^+$ immune cells (FIG. 10B). Specifically, CBD-CCL4 combination therapy mediated the highest recruitment of CD103$^+$ DCs, CD8α cross-presenting DCs, and CD8$^+$ T cells (FIG. 10C-10E). Significant increases in total CD11c$^+$ DCs was also observed (FIG. 10F). CBD-CCL4 therapy did not increase recruitment of CD4$^+$ T cells, nor did it enhance the fraction of Tregs in the CD4$^+$ T cell compartment (FIG. 10G, 10H). Taken together, these results once again highlight the importance of targeted CCL4 delivery in the recruitment of key cell populations to enhance the efficacy of CPI therapy.

Encouraged by the results seen with combination therapy in B16F10 melanoma when treating tumors at early time points, further investigation as to whether CPI therapy in combination with CBD-CCL4 could slow growth of established B16F10 tumors was performed. Tumors were allowed to progress until their volume was greater than 50 mm$^3$, after which tumors were treated with CPI therapy alone or CPI+CBD-CCL4. Importantly, combination therapy significantly slowed tumor growth following a single administration; furthermore, combination therapy prolonged mouse survival, with mice co-administered CPI therapy with CBD-CCL4 surviving for an average of 22 days, compared to 14 days for CPI therapy alone (FIG. 11). Extending from these results, the inventors investigated as to whether CBD-CCL4 could synergize with anti-programmed cell death protein 1 (αPD-1, CD279), another clinically approved immunotherapy for a number of indications, including melanoma, non-small cell lung cancer, bladder cancer, renal cell carcinoma, and hepatocellular carcinoma, among others (Gong et al., *J Immunother Cancer* 6, 8, 2018). Using two syngenic colon cancer models, CT26 and MC38, it was found that combination of αPD-1 therapy and CBD-CCL4 mediated the slowest tumor growth rates in both models, significantly enhancing therapeutic benefit relative to antibody therapy alone or combination with WT CCL4 (FIG. 12). These results highlight that CBD-CCL4 can be combined with multiple CPI antibody therapies to improve therapeutic effect. Furthermore, since the targeting approach used for CBD-CCL4 therapy utilizes the tumor extracellular matrix, as opposed to a specific protein on the surface of tumor cells, this therapy can be applied to a number of different tumor models to improve efficacy of CPI therapy.

Finally, the efficacy of combination therapy in a spontaneous breast cancer model was investigated. To this point, antitumor efficacy of CBD-CCL4 has been demonstrated in multiple implantable tumor models. While striking, these models develop rapidly, which may impact the leakiness and disordered nature of the tumor microvasculature (Nakamura et al., *Bioconjug Chem* 27, 2225-38, 2016), making it more amenable to targeted via our collagen-binding approach. Slow developing tumors, on the other hand, may not exhibit this same disordered vasculature (Golombek et al., *Adv Drug Deliv Rev* 130, 17-38, 2018), limiting the effectiveness of CBD-CCL4 therapy. For this study, female FVB/N-Tg (MMTV-PyVT)634Mu/J (MMTV-PyMT) mice were used, which develop invasive ductal carcinomas in their mammary fat pads around 6-7 weeks after birth (Fantozzi and Christofori, *Breast Cancer Res* 8, 212, 2006; Guy et al., *Mol Cell Biol* 12, 954-61, 1992). This model is also histologically similar to human breast cancers (Lin et al., *Am J Pathol* 163, 2113-26, 2003), making it a suitable model to demonstrate the translational potential of CBD-CCL4 combination therapy. Once again, CBD-CCL4 in combination with CPI therapy slowed tumor growth relative to CPI therapy alone (FIG. 13). While survival results were not significantly different, median survival time did increase to 29 days following initial therapy for the combination therapy, compared to 23 days for CPI therapy alone. These results demonstrate that CBD targeting can also be applied to spontaneously developing tumors in addition to implantable tumor models, highlighting the translational potential of this approach. Further optimization of dosing regimens may further improve the benefit afforded by CBD-CCL4 combination therapy.

The inventors have demonstrated a novel method for enhancing the efficacy of CPI immunotherapy (e.g., αPD-1, αPD-L1, and αCTLA-4) through the recruitment of CD103$^+$ DCs to the tumor microenvironment using the chemokine CCL4. CBD-CCL4 in combination with CPI therapy, but not WT CCL4 or CPI therapy alone, significantly enhanced the immune infiltrates in both B16F10 and EMT6 tumors and slowed tumor growth. Detailed characterization of the tumor immune cell composition confirmed that significant increases of CD103$^+$ DCs and CD8$^+$ T cells occurred following CBD-CCL4 combination therapy. This method is amenable to combination with multiple CPI antibody therapies and can be applied to multiple tumor types, highlighting its significant potential for clinical translation for improved cancer immunotherapies.

B. Materials and Methods

Production and purification of recombinant VWF A3 domain-CCL4 fusion protein. The sequences encoding for the fusion of human vWF A3 domain residues Cys1670-Gy1874 (907-1111 of mature vWF), a (GGGS)$_2$ linker and murine CCL4 was synthesized and cloned into the pcDNA3.1(+) CMV-driven mammalian expression vector by Genscript. A sequence encoding for the 6× His-tag was added at the N-terminus for downstream purification of the recombinant protein. Suspension-adapted HEK-293F cells were maintained in serum-free FreeStyle293 Expression Medium™ (Gibco). Protein production was performed according to previous protocols (Ishihara et al., *Sci Transl Med*, 2019; Ishihara et al., *Nat Commun* 9, 2163, 2018). Briefly, on the day of transfection, cells were transferred into fresh medium at a density of 1×10$^6$ cells/mL. 1 µg/mL plasmid DNA was mixed with 2 µg/ml linear 25 kDa polyethylenimine (Polysciences) diluted in OptiPRO™ SFM media (Thermo Fisher), incubated for 20 min, and added dropwise to the cells (4% v/v final concentration). The culture flask was agitated in a humidified orbital shaking incubator at 135 rpm at 37° C. in the presence of 5% CO$_2$. 6 days after transfection, the cell culture medium was collected, centrifuged, and filtered through a 0.22 m filter. Culture media was loaded into a HisTrap™ HP 5 mL column (GE Healthcare), using an ÄKTA pure 25 (GE Healthcare). After washing the column with wash buffer (20 mM imidazole, 20 mM NaH$_2$PO$_4$, 0.5 M NaCl, pH 7.4), protein was eluted with a gradient of 500 mM imidazole (in 20 mM NaH$_2$PO$_4$, 0.5 M NaCl, pH 7.4). The eluted protein was further purified with size exclusion chromatography using a HiLoad™ Superdex 200PG column (GE Healthcare). All purification steps were carried out at 4° C. The expression of CBD-CCL4 was determined by western blotting using anti-His tag antibody (BioLegend, Clone J099B12), and the proteins were verified as >90% pure by SDS-PAGE. Native form murine CCL4 protein was purchased commercially from Biolegend.

Murine CCL4-
(SEQ ID NO: 25)
APMGSDPPTSCCFSYTSRQLHRSFVMDYYETSSLCSKPAVVFLTKRGRQI

CANPSEPWVTEYMSDLELN

Human vWF A3 domain and murine CCL4 fusion protein-
(SEQ ID NO: 47)
CSQPLDVILLLDGSSSFPASYFDEMKSFAKAFISKANIGPRLTQVSVLQY

GSITTIDVPWNVVPEKAHLLSLVDVMQREGGPSQIGDALGFAVRYLTSEM

HGARPGASKAVVILVTDVSVDSVDAAADAARSNRVTVFPIGIGDRYDAAQ

LRILAGPAGDSNVVKLQRIEDLPTMVTLGNSFLHKLCSGFVRIGGGGSGG

GGSAPMGSDPPTSCCFSYTSRQLHRSFVMDYYETSSLCSKPAVVFLTKRG

RQICANPSEPWVTEYMSDLELNHHHHHH

SDS-PAGE analysis of protein molecular weight and purity. The measurement was performed as described previously (Ishihara et al., *Sci Transl Med* 9, 2017). SDS-PAGE was performed on 4-20% gradient gels (Bio-Rad) after CCL4 or CBD-CCL4 was reduced with β-mercaptoethanol. After electrophoresis, gels were stained with SimplyBlue SafeStain™ (Thermo Fisher Scientific) according to the manufacturer's recommendations. Gel images were acquired with the ChemiDoc XRS+ system™ (Bio-Rad).

CBD-CCL4 collagen binding measurements using SPR. SPR measurements were made with a Biacore X100 SPR system™ (GE Healthcare). Collagen I or collagen III was immobilized via amine coupling on a CM5 chip (GE Healthcare) for ~1000 resonance units (RU) according to the manufacturer's instructions. CBD-CCL4 was flowed for 90 s (for collagen I) and for 30 s (for collagen III) at increasing concentrations in the running buffer at L/min. The sensor chip was regenerated with 50 mM NaOH for each cycle. Specific binding of CBD-CCL4 to collagen was calculated automatically using the response to a non-functionalized channel as a reference. Binding curves were fitted using BIAevalution™ software (GE Healthcare). CBD-CCL4 binding results were fitted with Langmuir binding kinetics (1:1 binding).

GPCR calcium flux signaling assay. GPCR signaling following interaction with native form CCL4 or CBD-CCL4 was analyzed using a calcium flux assay (FLUOFORTE™ Calcium Assay Kit, Enzo Life Sciences). The assay was performed according to the manufacturer's protocol with slight modifications. Reagents were reconstituted, mixed as directed, and brought to room temperature before use. 24 h prior, 1.5×10$^5$ ThP1 human monocytes, known to express CCR5 (Gouwy et al., *Eur J Immunol* 41, 963-73, 2011), were plated in each well of a tissue-culture treated 96 well round bottom plate. On the day of the assay, cells were spun down at 2000 RPM for 2 min, media was removed, and cells were resuspended in 100 µL of assay buffer. Cells were subsequently incubated for 45 min at 37° C. and then for 15 min at room temperature prior to assay. Samples were then prepared separately in PBS in triplicate and then diluted 1:4 upon addition to the cells to give the indicated molar concentration of CCL4. After addition of the compound, samples were mixed several times with a multichannel pipette to ensure thorough mixing, after which they were transferred to a black-walled clear bottom 96 well plate.

Calcium signaling was then measured using a Cytation™ 3 multi-mode plate reader (BioTek) at an excitation wavelength of 490 nm and an emission wavelength of 525 nm, using bottom-read optics with the gain set at 100. $EC_{50}$ values were calculated using a non-linear dose-response curve fitting model comparing log (test compound) vs. response in GraphPad Prism™.

Tumor cell line culture and maintenance and animal sourcing. All cells were maintained in a humidified incubator at 37° C. and 5% $CO_2$. Cells were routinely passaged using TrypLE Express™ (Thermo Fisher) once they reached 80-90% confluence. B16F10 melanoma and MC38 colon carcinoma cells were maintained in Dulbecco's Modified Eagle Medium™ (DMEM) supplemented with 10% (v/v) fetal bovine serum (FBS, Certified, US Origin, Heat-Inactivated, Gibco) and 500 U/mL (1% v/v) penicillin-streptomycin (P/S, Gibco). EMT6 breast cancer, CT26 colon carcinoma, and ThP1 monocyte cells were maintained in RPMI1640 supplemented with 10% (v/v) FBS and 1% (v/v) P/S. All cells were confirmed to be mycoplasma free using a MycoAlert Plus™ mycoplasma assay (Lonza). Female C57BL/6 and Balb/C mice, age 8 wk to 12 wk, were obtained from the Jackson Laboratories. Female FVB/N-Tg (MMTV-PyVT)634Mu/J (MMTV-PyMT) mice, age 4 wk to 6 wk, were obtained from the Jackson Laboratories. MMTV-PyMT mice were inspected weekly until tumors were palpable in at least 4 mammary fat pads. All mice were acclimated in their cages for 72 h prior to use. Treatments were randomized within cages to minimize cage-specific treatment effects. All animal experiments were performed with approval and according to the policies of the Institutional Animal Care and Use Committee at The University of Chicago.

Blood plasma half-life characterization. $5 \times 10^5$ B16F10 melanoma cells were injected intradermally on the left side of the back of each mouse. WT CCL4 and CBD-CCL4 were fluorescently labeled using Dylight™ 800-NHS (Thermo Fisher), and unreacted dye was removed by a Zebaspin™ spin column (Thermo Fisher) according to the manufacturer's instruction. After 4 days, mice were injected with 25 µg WT CCL4-DyLight™ 800 or the molar equivalent (25 µg CCL4 basis, or 93 g total protein) of CBD-CCL4-DyLight™ 800 via i.v. injection. Blood samples were collected into EDTA-containing tubes via facial bleed at 1 min, 5 min, 10 min, and 30 min after administration. Samples were then centrifuged at 2000 rpm for 5 min to collect plasma. Concentrations of CCL4 in plasma were measured using a LI-COR™ Infrared Odyssey™ Imager, and concentrations ere calculated from a standard dilutions series of labeled WT CCL4 or CBD-CCL4. Blood plasma half-life was determined using a one-phase decay model using GraphPad Prism™ software (Version 7).

Biodistribution analysis in EMT6 tumor-bearing mice. WT CCL4 or CBD-CCL4 protein was fluorescently labeled using DyLight™ 647 NHS ester (Thermo Fisher), and unreacted dye was removed by a Zebaspin™ spin column (Thermo Fisher) according to the manufacturer's instruction. A total of $5 \times 10^5$ EMT6 cells re-suspended in 50 µL of PBS were injected subcutaneously into the mammary fat pad on the right side of each Balb/C mouse. When the tumor reached approximately 500 $mm^3$, 25 g DyLight™ 647 labeled CCL4 or 25 g (6.7 µg CCL4 basis) DyLight™ 647-labeled CBD-CCL4 was injected i.v. 30 min after injection, mice were sacrificed and tumors were extracted and imaged with the Xenogen IVIS Imaging System™ 100 (Xenogen) under the following conditions: f/stop: 2; optical filter excitation 640 nm; emission 670 nm; exposure time: 0.5 sec; small binning. CCL4 concentration in each tumor was calculated based on a standard dilution series of WT CCL4 or CBD-CCL4 labeled with DyLight™ 647 and normalized to the weight of the tumor.

Anti-tumor efficacy in B16F10 melanoma. A total of $5 \times 10^5$ B16F10 cells resuspended in 50 µL PBS were inoculated intradermally on the left side of the back of each C57BL/6 mouse. After 4 d (or 7 d for established tumor treatment study), mice were injected with WT CCL4 (25 µg given via i.v. injection) or molar equivalent CBD-CCL4 (25 µg CCL4 basis, or 93 g CBD-CCL4, given via i.v. injection) in combination with CPI antibody therapy consisting of 100 g each αPD-L1 and αCTLA4 given via i.p. injection. CPI therapy alone was administered as control. Tumors were measured with a digital caliper starting 4 days after tumor inoculation, and volumes were calculated as ellipsoids, where V=4/3×π×depth/2×width/2×height/2. Mice were sacrificed when tumor volume exceeded 500 $mm^3$ or when early removal criteria were met due to poor health of the mice. In the case of cell infiltrate analysis, mice were sacrificed 10 d after tumor inoculation.

Anti-tumor efficacy in EMT6 breast cancer. A total of $5 \times 10^5$ EMT6 cells re-suspended in 50 µL of PBS were injected subcutaneously into the mammary fat pad on the right side of each Balb/C mouse. 6 d and 9 d after tumor inoculation, tumors were administered with WT CCL4 (25 µg given via i.v. injection) or molar equivalent CBD-CCL4 (25 µg CCL4 basis, or 93 µg CBD-CCL4, given via i.v. injection) in combination with CPI antibody therapy consisting of 100 µg each αPD-L1 and αCTLA4 given via i.p. injection. CPI therapy alone was administered as control. Tumors were measured with a digital caliper starting 4 days after tumor inoculation as described above. Mice were sacrificed 10 d after tumor inoculation to evaluate immune cell infiltration.

Anti-tumor efficacy in CT26 and MC38 colon carcinoma. A total of $5 \times 10^5$ CT26 or MC38 cells re-suspended in 50 µL of PBS were inoculated intradermally on the left side of the back of each Balb/c (for CT26) or C57BL/6 (for MC38) mouse. After 5 days, mice were injected with unmodified CCL4 (25 µg given via i.v. injection) or molar equivalent CBD-CCL4 (25 µg CCL4 basis, or 93 µg CBD-CCL4, given via i.v. injection) in combination with 100 µg αPD-1 antibody therapy given via i.p. injection. Tumors were measured with a digital caliper starting 5 days after tumor inoculation as described above. Mice were sacrificed when tumor volume exceeded 500 $mm^3$.

Anti-tumor efficacy in MMTV-PyMT breast cancer. Once total tumor volume reached approximately 100 $mm^3$, mice were treated with CBD-CCL4 (25 µg CCL4 basis, or 93 µg CBD-CCL4, given via i.v. injection) in combination with CPI antibody therapy consisting of 100 µg each αPD-L1 and αCTLA4 given via i.p. injection. Identical treatments were given 7 d and 14 d after initial therapy. Tumors were measured bi-weekly with a digital caliper as described above, and mice were sacrificed once tumor volume exceeded 1000 $mm^3$ or mice experienced adverse effects due to tumor burden.

Tissue and single-cell preparation for immune cell analysis. Both B16F10 and EMT6 tumors were harvested 10 d after initial tumor inoculation. All cell isolation procedures were adapted from previously reported methods (Ishihara et al., *Sci Transl Med* 9, 2017; Ishihara et al., *Sci Transl Med*, 2019). Tumors were minced into small pieces, after which enzymatic digestion consisting of 2 mg/mL collagenase D and 40 µg/mL DNase I (Roche) in DMEM containing 2% FBS was performed for 30 min at 37° C. under gentle agitation. Single-cell suspensions were obtained by gently disrupting the enzyme-treated tumor through a 70-μm cell strainer. Red blood cells were lysed with ACK lysing buffer (Quality Biological), after which cells were centrifuged and resuspended in flow cytometry staining buffer consisting of PBS containing 2% FBS for downstream analysis.

Flow cytometry analysis and antibodies used. Single cell suspensions from tumors were prepared as described above. Antibodies against the following molecules were used in all experiments: anti-mouse CD3 (145-2C11, BD Biosciences), anti-mouse CD4 (RM4-5, BD Biosciences), anti-mouse CD8α (53-6.7, BD Biosciences), anti-mouse CD25 (PC61, BD Biosciences), anti-mouse CD45 (30-F11, Biolegend) anti-mouse CD44 (IM7, Biolegend), anti-mouse CD62L (MEL-14, BD Biosciences), anti-mouse PD-1 (29F.1A12, Biolegend), anti-mouse NK1.1 (PK136, Biolegend), anti-mouse Foxp3 (MF23, BD Biosciences), anti-mouse F4/80 (BM8, Biolegend), anti-mouse MHCII (M5/114.15.2, BioLegend), anti-mouse CD11b (M1/70, BioLegend), anti-mouse CD11c (N418, Biolegend), anti-mouse CD19 (1D3, BD Biosciences), anti-mouse Gr-1 (RB6-8C5, Biolegend) and anti-mouse CD103 (M290, BD Biosciences) Live/dead cell discrimination was performed using Fixable Viability Dye eFluor 455 (eBioscience) according to the manufacturer's instructions; an Fc receptor blocking step (anti-mouse CD16/32, clone 93, Biolegend) was also included to minimize non-specific antibody binding. Surface staining was carried out on ice for 20 min, and intracellular staining was performed using the FoxP3-transcription factor staining kit according to manufacturer's instructions (eBioscience). Otherwise, samples were fixed in 2% paraformaldehyde in PBS. All flow cytometric analyses were done using a Fortessa™ (BD Biosciences) flow cytometer and analyzed using FlowJo™ software (Tree Star).

Statistical Analysis. The statistical significance between treatment groups was assessed using Prism™ software (v7, GraphPad). For multiple comparisons, ANOVA followed by Tukey's HSD post hoc test was used when between groups was found to be similar by Brown-Forsythe test. For non-parametric data, Kruskal-Wallis test followed by Dunn's multiple comparison test was used. For comparisons between two groups, a two-tailed Student's t-test was used. Survival curves were analyzed using the log-rank (Mantel-Cox) test. $*p<0.05$; $p<0.01$; $*p<0.001$; $****p<0.0001$.

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

The invention claimed is:

1. A method for treating cancer in a subject comprising administering a polypeptide comprising IL-12 conjugated to the collagen binding domain of SEQ ID NO:3 or 34 to the subject; wherein the cancer comprises colon, breast, prostate, pancreatic, glioblastoma, ovarian, or head and neck cancer.

2. The method of claim 1, wherein the polypeptide comprising IL-12 is at least 85% identical to SEQ ID NO:37 or SEQ ID NO:35.

3. The method of claim 1, wherein the subject is being treated with a checkpoint inhibitor.

4. The method of claim 3, wherein the checkpoint inhibitor comprises and anti-PD-1, an anti-PD-L1, an anti-CTLA-4 antibody, or combinations thereof.

5. The method of claim 4, wherein the checkpoint inhibitor comprises an i) an anti-PD-1 or anti-PD-L1 and ii) an anti-CTLA-4 antibody.

* * * * *